US007205311B2

(12) United States Patent
Neidle et al.

(10) Patent No.: US 7,205,311 B2
(45) Date of Patent: Apr. 17, 2007

(54) THERAPEUTIC ACRIDONE AND ACRIDINE COMPOUNDS

(75) Inventors: Stephen Neidle, Bushey (GB); Richard John Harrison, Saffron Walden (GB); Lloyd Royston Kelland, Reigate (GB); Sharon Michele Gowan, Tolworth (GB); Martin Anthony Read, Sheerness (GB); Anthony Reszka, Kilburn (GB)

(73) Assignee: Cancer Research Technology Limited, London ( * ) Notice: Subject to any disclaimer, the term of this patent is extended or adjusted under 35 U.S.C. 154(b) by 35 days.

(21) Appl. No.: 10/501,474

(22) PCT Filed: Jan. 14, 2003

(86) PCT No.: PCT/GB03/00102

§ 371 (c)(1),
(2), (4) Date: Jul. 14, 2004

(87) PCT Pub. No.: WO03/059885

PCT Pub. Date: Jul. 24, 2003

(65) Prior Publication Data

US 2005/0070568 A1    Mar. 31, 2005

Related U.S. Application Data

(60) Provisional application No. 60/347,899, filed on Jan. 15, 2002.

(51) Int. Cl.
*A01N 43/42* (2006.01)
*A61K 31/44* (2006.01)
*C07D 219/00* (2006.01)
*C07D 221/06* (2006.01)

(52) U.S. Cl. .................. 514/297; 546/102; 546/110

(58) Field of Classification Search ................ 546/110, 546/102; 514/297
See application file for complete search history.

(56) References Cited

U.S. PATENT DOCUMENTS

2003/0207909 A1   11/2003   Neidle

FOREIGN PATENT DOCUMENTS

DE        488 890          1/1930
WO    WO 02/08193 A1        1/2002

OTHER PUBLICATIONS

McConnaughie et al., "Novel Acridine-Triazenes as Prototype Combilexins:Synthesis, DNA Binding, and Biological Activity", Journal of medicinal Chemistry, vol. 38, pp. 3488-3501.*
Bears et al., "Telomere maintenance mechanisms as a target for drug development", Oncogene, vol. 19, pp. 6632-6641.*
Vietor et al., "On the significance of telomerase activity in human malignant glima cell", European Journal of Pharmacology, vol. 407, pp. 27-37.*
Alberti, P., et al., 2002, "Benzoindoloquinolines Interact with DNA Tetraplexes and Inhibit Telomerase," *Biorganic & Medicinal Chemistry Letters*, vol. 12, pp. 1071-1074.
Autexier, C., 1999, "Telomerase as a Possible Target for Anticancer Therapy," *Chemistry & Biology*, Nov. 1999, vol. 6, pp. R299-R303.
Bogert, M.T., et al., 1930, "Researchers in the Acridine Series. The Synthesis of Isomers of Proflavine and of Neutral Acriflavine," *Collect. Czech. Chem. Comm.*, vol. 2, pp. 383-395.
Bostock-Smith, C.E., et al., 1999, "Molecular Recognition between a New Pentacyclic Acridinium Salt and DNA Sequences Investigated by Optical Spectroscopic Techniques, Proton Nuclear Magnetic Resonance Spectroscopy, and Molecular Modeling," *Biochemistry*, vol. 38, No. 21, pp. 6723-6731.
Cain, B.F., et al., 1974, "Potential Antitumor Agents. 14. Acridylmethanesulfonanilides," *J. Med. Chem.*, vol. 17, No. 9, pp. 922-930.
Cain, B.F., et al., 1976, "Potential Antitumor Agents. 17. 9-Anilino-10-methylacridinium salts," *J. Med. Chem.*, vol. 19, No. 6, pp. 772-777.
Cain, B.F., et al., 1976, "Potential Antitumor Agents. 19. Multiply Substituted 4'-(9-Acridinylamino)methanesulfonanilides," *J. Med. Chem.*, vol. 19, No. 9, pp. 1124-1129.

(Continued)

*Primary Examiner*—Margaret D. Seaman
*Assistant Examiner*—Niloofar Rahmani
(74) *Attorney, Agent, or Firm*—Nixon & Vanderhye P.C.

(57) ABSTRACT

This invention pertains to certain acridone and acridine compounds of the formula which inhibit telomerase, regulate cell proliferation, etc., and/or treat cancer, proliferative conditions, etc.: wherein either: (a) K is =O, L is —H, alpha single bond, beta is a double bond, gamma is a single bond (acridones); or, (b) K is a 9-substituent, L is absent, alpha is a double bond, beta is a single bond, gamma is a double bond (acridines); and wherein: $J^1$ is a 2- or 3-substituent; $J^2$ is a 6- or 7-substituent; $J^1$ and $J^2$ are each a group of the formula —N($R^N$)—W, wherein: $R^N$ is a nitrogen substituent and is hydrogen, $C_{1-7}$alkyl, $C_{3-20}$heterocyclyl, or $C_{5-20}$aryl, and is optionally substituted; and, W is $C_{1-17}$alkyl, $C_{3-20}$heterocyclyl, or $C_{5-20}$aryl, and is optionally substituted; and, wherein, when K is a 9-substituent, K is a group of the formula —N($R^N$)—Q, wherein: $R^N$ is an amino substituent and is hydrogen, $C_{1-7}$alkyl, $C_{3-20}$heterocyclyl, or $C_{5-20}$aryl; and, Q is $C_{1-7}$alkyl, $C_{3-20}$heterocyclyl, or $C_{5-20}$aryl, and is optionally substituted; and pharmaceutically acceptable salts, esters, amides, solvates, hydrates, and protected forms thereof. The present invention also pertains to pharmaceutical compositions comprising such compounds, and the use of such compounds and compositions, both in vitro and in vivo, to inhibit telomerase, to regulate cell proliferation, etc., and/or in the treatment of cancer, proliferative conditions, etc.

59 Claims, 13 Drawing Sheets

OTHER PUBLICATIONS

Carrasco, C., et al., 2002, "Tight Binding of te Antitumor Drug Ditercalcinium to Quaduplex DNA," *ChemBioChem*, vol. 3, pp. 1235-1241.

Corey, D.R., 2002, "Telomerase Inhibition, Oligonucleotides, and Clinical Trials," *Oncogene*, vol. 21, pp. 631-637.

Denny, W.A., et al., 1982, "Potential Antitumor Agents. 36. Quantitative Relationships between Experimental Antitumour Activity, Toxicity, and Structure for the General Class of 9-Anilinoacridine Antitumor Agents," *J. Med. Chem.*, vol. 25, pp. 276-315.

Gamage, S.A., et al., 1994, "Synthesis and in Vitro Evaluation of 9-Anilino-3,6-diaminoacridines Active Against a Multidrug Resistant Strain of the Malaria Parasite Plasmodium falciparum," *J. Med. Chem.*, vol. 37, No. 10, pp. 1486-1494.

Gimenez-Arnau, E. et al., 1998, "Antitumour Polycyclic Acridines, Part 2," *Anti-Cancer Drug Design*, vol. 13, pp. 125-143.

Gimenez-Arnau, E., et al., 1998, "Antitumour Polycyclic Acridines, Part 4," *Anti-Cancer Drug Design*, vol. 13, pp. 431-451.

Goldberg, A.A. and Kelly, W., 1946, "29. Synthesis of Diaminoacridines. Part I," *J. Chem.Soc.*, p. 102-111.

Goldstein, H., and de Simo, M., 1927, "Quelques derives de l'acide phenyl-anthranilique III," *Helv. Chim. Acta.*, vol. 10, p. 603-606.

Gomez, D., et al., 2002, "Detection of Telomerase Inhibitors Based on G-Quadruplex Ligands by a Modified Telomeric Repeat Amplification Protocol Assay," *Cancer Research*, vol. 62, pp. 3365-3368.

Gowan, S.M., et al., 2002, "A G-Quadruplex-Interactive Potent Small-Molecule Inhibitor of Telomerase Exhibiting in Vitro and in Vivo Antitumour Activity," *Molecular Pharmacology*, vol. 61, No. 5, pp. 1154-1162.

Hagan, D.H., et al., 1997, "Antitumour Polycyclic Acridines, Part 1," *J. Chem. Soc., Perkin Trans. 1*, pp. 2739-2746.

Hagan, D.H., et al., 1998, "Antitumour Polycyclic Acridines, Part 3," *J. Chem. Soc., Perkin Trans. 1*, p. 915-923.

Harrison, R.J., et al., 1999, "Human Telomerase Inhibition by Substituted Acridine Derivatives," *Bioorganic & Medicinal Chemistry Letters*, vol. 9, pp. 2463-2468.

Herbert, B.-S., et al., 2001, "Telomerase and Breast Cancer," *Breast Cancer Research*, vol. 3, pp. 146-149.

Hoffmann, S., et al., 1986, "Synthese bisbasisch-substituierter Acridine als potentielle Nucleinsaureelfecktoren," *Zeitschrift fur Chemie*, vol. 26, No. 9, pp. 331-332.

Julino, M., et al., 1998, "Antitumour Polycyclic Acridines, Part 5," *J. Chem. Soc., Perkin Trans. 1*, pp. 1677-1684.

Kern, J.T., et al., 2002, "The Relationship between Ligand Aggregation and G-Quadruplex DNA Selectivity in a Series of 3,4,9,10-Perylenetetracarboxylic Acid Diimides," *Biochemistry*, vol. 41, pp. 11379-11389.

Kim, M.-Y., et al., 2002, "Telomestatin, a Potent Telomerase Inhibitor That Interacts Quite Specifically with the Human Telomeric Intramolecular G-Quadruplex," *J. Amer. Chem. Soc.*, vol. 124, No. 10, pp. 2098-2099.

Kim, N.W., et al., 1994, "Specific Association of Human Telomerase Activity with Immortal Cells and Cancer", *Science*, vol. 266, pp. 2011-2015.

Klopman, G., et al., 1987, "Computer-Automated Structure Evaluation of Antiluekemic 9-Anilinoacridines," *Molecular Pharmacology*, vol. 31, pp. 457-476.

Korolev, B.A., et al., 1976, "Preparation of 2-Aminoacridan by the Reduction of 2-Amino-9-Acridanone with Biborane," *J. Gen. Chem. USSR (Engl. Trans.)*, vol. 46, pp. 2250-2252.

Korolev, B.A., et al., 1977, "Acridines. II. Selective Reductionof Nitro Derivatives of 2-Amino-9-Acridanone with Diborane," *J. Gen. Chem. USSR (Engl. Trans.)*, vol. 47, pp. 2118-2122.

Li, J.-L., et al., 2001, "Inhibition of the Bloom's and Werner's Syndrome Helicases by G-Quadruplex Interacting Ligands", *Biochemistry*, vol. 40, pp. 15194-15202.

Lorente, A., et al., 1996, "Syntheses of Imidazole-Acridine Conjugates as Ribonuclease A Mimics," *Tetrahedron Letters*, vol. 37, No. 25, pp. 4417-4420.

Matsumura, K., 1929, "The Synthesis of Certain Acridine Compounds," *J. Amer. Chem. Soc.*, vol. 51, pp. 816-820.

Mergny, J.-L., et al., 2002, "Natural and Pharmacological Regulation of Telomerase," *Nucleic Acids Research*, vol. 30, No. 4, pp. 839-865.

Moisan, M., et al., 1993, "New α, ω-Diamino Mono- and Di-Bridged Acridine Dimers," *Monatshefte fur Chemie*, vol. 124, pp. 23-35.

Neidle, S., et al., 1999, "Telomerase as an Anti-Cancer Target: Current Status and Future Prospects," *Anti-Cancer Drug Design*, vol. 14, pp. 341-347.

Neidle, S., et al., 2002, "Telomere Maintenance as a Target for Anticancer Drug Discovery," *Nature Reviews*, vol. 1, May 2002, pp. 383-393.

Parkinson, G.N., et al., 2002, "Crystal structure of parallel quadruplexes from human telomeric DNA," *Nature*, vol. 417, Jun. 20, 2002, pp. 876-880.

Perry, P.J., et al., 1998a, "1,4- and 2,6-Disubstituted Amidoanthracene-9,10-dione Derivatives as Inhibitors of Human Telomerase," *J. Med. Chem.*, vol. 41, No. 17, pp. 3253-3260.

Perry, P.J., et al., 1998b, "Human Telomerase Inhibition by Regioisomeric Disubstituted Amidoanthracene-9,10-diones," *J. Med. Chem.*, vol. 41, No. 24, pp. 4873-4884.

Perry, P.J., et al., 1998c, "Telomeres and Telomerase: Targets for Cancer Chemotherapy?," *Exp. Opin. Ther. Patents*, vol. 8, No. 12, pp. 1567-1586.

Perry, P.J., et al., 1999a, "Design, Synthesis and Evaluation of Human Telomerase Inhibitors Based Upon a Tetracyclic Structural Motif," *Anti-Cancer Drug Design*, vol. 14, pp. 373-382.

Perry, P.J., et al., 1999b, "2,7-Disubstituted Amidofluorenon Derivatives as Inhibitors of Human Telomerase," *J. Med. Chem.*, vol. 42, No. 14, pp. 2679-2684.

Read et al., Apr. 24, 2001, "Structure-based design of selective and potent G quadruplex-mediated telomerase inhibitors," *Proceedings of the National Academy of Science*, vol. 98, No. 9, pp. 4844-4849.

Read, M.A., et al., 1999, "Molecular Modeling Studies on G-Quadruplex Complexes of Telomerase inhibitors: Structure-Activity Relationships," *J. Med. Chem.*, vol. 42, pp. 458-4546.

Reddel, R.R., 2003, "Alternative Lengthening of Telomeres, Telomerase, and Cancer," *Cancer Letters*, 194, pp. 155-162.

Rezler, E.M., et al., 2002, "Telomeres and Telomerases as Drug Targets," *Current Opinion in Pharmacology*, vol. 2, pp. 415-423.

Riou, J.F., et al., 2002, "Cell Senescence and Telomere Shortening Induced by a New Series of Specific G-Quadruplex DNA Ligands," *Proc. Nat. Acad. Sci.*, vol. 99, No. 5, pp. 2627-2677.

Sharma, S., et al., 1997, "Preclinical and Clinical Strategies for Development of Telomerase and Telomere Inhbitors," *Annals of Oncology*, vol. 8, pp. 1063-1074.

Shay, J.W., et al., 2002, "Telomerase: A Target for Cancer Therapeutics," *Cancer Cell*, vol. 2, pp. 257-265.

Sun, D., et al., 1997, "Inhibition of Human Telomerase by a G-Quadruplex-Interactive Compound," *J. Med. Chem.*, vol. 40, pp. 2113-2116.

Urquidi, V., et al., 1998, "Telomerase in Cancer: Clinical Applications," *Ann. Med.*, vol. 30, pp. 419-430.

Yale, H.L., 1955, "3-Chloro-10-dialkylaminoalkylphenothiazines," *J. Amer. Chem. Soc.*, vol. 77, pp. 2270-2272.

Johnson et al (British Journal of Cancer (2001) 84(10), 1424-1431).

* cited by examiner

THERAPEUTIC ACRIDONE AND ACRIDINE COMPOUNDS

RELATED APPLICATION

This application is the US national phase of international application PCT/GB03/00102 filed 14 Jan. 2003, which designated the U.S. and claims priority to U.S. Application No. 60/347,899 filed 15 Jan. 2002. The entire contents of these applications are incorporated herein by reference.

TECHNICAL FIELD

This invention pertains generally to the field of chemistry and pharmaceuticals, and more specifically to certain acridine and acridine compounds which inhibit telomerase, regulate cell proliferation, etc., and/or treat cancer, proliferative conditions, etc. The present invention also pertains to pharmaceutical compositions comprising such compounds, and the use of such compounds and compositions, both in vitro and in vivo, to inhibit telomerase, to regulate cell proliferation, etc., and/or in the treatment of cancer, proliferative conditions, etc.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Mammalian cells are normally subject to tight controls regulating replication in order to maintain organ structure and function. Conversely, the disease of cancer is characterized by uncontrolled proliferation. Compromise of any of the steps involved in cell cycle regulation could be involved in escape from regulatory mechanisms and therefore lead to neoplasia. However, even if a cell escapes proliferation suppression, there are limitations to the number of replicative cycles it can progress through before safety mechanisms cause cell cycle shutdown, and this restriction is thought to be a component of the process of organismal aging. Although aging is a complex process, a major candidate for the molecular signal for replicative senescence is that of telomere shortening.

Telomeres are nucleoprotein structures at the ends of linear chromosomes consisting of DNA sequences arranged in tandemly repeated units which extend from less than 100 to several thousands of bases. In contrast to chromosome ends created by random breakage, telomeres are stable structures not prone to degradation or fusion with other chromosome ends and are not subject to DNA repair mechanisms.

During each round of cellular replication, both strands of DNA separate and daughter strands are synthesized in a slightly different manner on the leading and lagging strand. While the lead strand replicates in a continuous fashion using conventional DNA polymerase, the lagging strand replicates in a discontinuous fashion using Okazaki fragments. The gaps between individual Okazaki fragments are filled by the regular DNA polymerase. However, this sets the stage for a potential "end replication problem." This arises because Okazaki fragment priming will not necessarily start at the very end of the DNA and because the RNA primer, once removed, would result in a portion of unreplicated 3'-DNA (an unrepaired 3'-overhang). This can lead to a loss of 50–200 base pairs with every round of somatic cell division, with eventual shortening of telomeres to a length that coincides with the activation of an antiproliferative mechanism termed "mortality stage 1" (M1), and at this stage, senescence in somatic cells occurs. Thus, telomere shortening functions as a "mitotic clock" and limits division in somatic cells to about 50–70 times, thereby contributing to cell aging.

In some cells, due to various mechanisms, the M1 stage is bypassed and cells can continue to divide until telomeres become critically shortened ("mortality stage 2," M2). At this M2 stage, in many immortalized cells, a specialized DNA polymerase called "telomerase" appears and utilizes its internal RNA template to synthesize the telomeric sequence and compensate for the loss of telomeric DNA due to incomplete replication. This prevents further shortening of telomeres, and the resulting stabilization of their length contributes to immortalization.

Telomerase is not expressed, or if it is, its activity is repressed, in most normal mammalian somatic cells. Exceptions to this rule include male germ line cells and some epithelial stem cells (e.g., as in the intestinal crypts, the basal layer of the epidermis, and within human hair follicles). Nonetheless, both telomerase activity and shortened but stabilized telomeres have been detected in the majority of tumours examined (and in over 90% of all human cancers examined), and consequently, telomeres and telomerase are recognized targets for anti-neoplastic (e.g., cancer) chemotherapy.

The absence of telomerase in most normal cells makes this enzyme a particularly attractive target, considering that its inhibition would probably cause minimal damage to the whole patient. The fact that tumour cells have shorter telomeres and higher proliferation rates than normal replicative cell populations suggests that a therapeutic telomerase inhibitor may cause tumour cell death well before damage to regenerative tissues occurs, thereby minimizing undesirable side-effects.

For a more detailed discussion of telomeres and telomerase, and their role as anti-proliferative targets, see, for example, Sharma et al., 1997; Urquidi et al., 1998; Perry et al., 1998c; Autexier, 1999; Neidle et al., 1999; 2001; Rezler et al., Parkinson et al., 2002; Neidle et al., 2002; Gowan et al., 2002; Herbert et al., 2002; Shay et al., 2002; Mergny et al., 2002; Corey et al., 2002; and references therein.

A range of telomerase inhibitors have been investigated. See, for example, Carrasco et al., 2002; Alberti et al., 2002; Riou et al., 2002; Kim et al., 2002; Kern et al., 2002; Gomez et al., 2002.

A number of polycyclic compounds, including polycyclic acridines, anthraquinones, and fluorenones have been shown to inhibit telomerase and/or to have anti-tumour effects in vitro. See, for example, Bostock-Smith et al., 1999; Gimenez-Arnau et al., 1998; Gimenez-Arnau et al., 1998; Hagan et al., 1997; Hagan et al., 1998; Harrison et al., 1999; Julino et al., 1998; Perry et al., 1998a, 1998b, 1999a, 1999b; Sun et al., 1997.

Harrison et al., 1999, describe certain 3,6-disubstituted acridines which are shown to inhibit telomerase, and to inhibit cell growth in certain ovarian carcinoma cell lines.

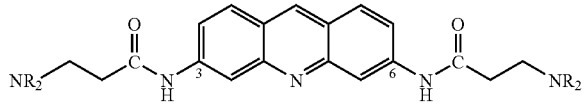

Read et al., April 2001, describe certain 3,6-disubstituted and 3,6,9-trisubstituted acridines (see compounds 1, 2, 3, and 4 in FIG. 1 therein), shown below (where n is 4 or 7, and R is —H or -Me). These compounds were shown to have potent in vitro inhibitory activity against human telomerase.

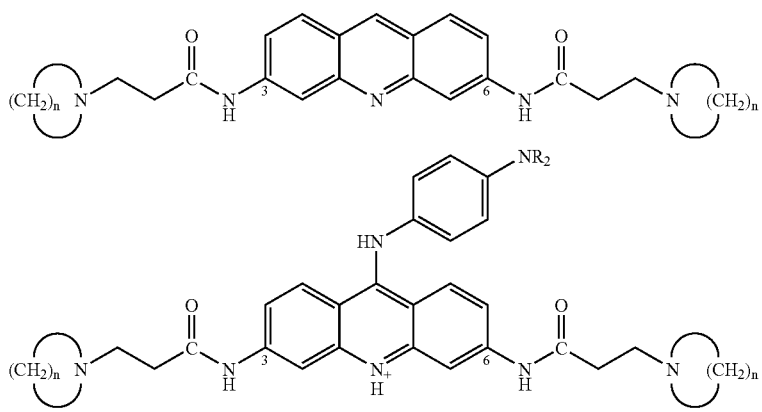

Neidle et al., 2002, describe various disubstituted acridines and trisubstituted acridines, shown below, which inhibit telomerase and/or regulate cell proliferation.

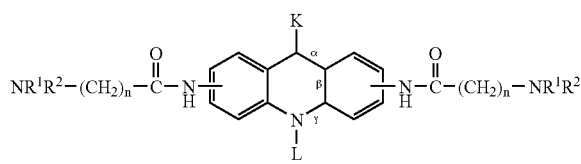

Lorente et al., 1996, describe the synthesis of certain 3,6-disubstituted acridines (which are also 9-H), shown below (wherein R' is —H or —Boc and R is —H or —CPh$_3$), which apparently are catalytically active and cleave t-RNA.

I.G. Farbenindustrie Akt.-Ges in Frankfurt a.M., 1930, describes one 3,6-disubstituted acridine (which is also 9-H), shown below.

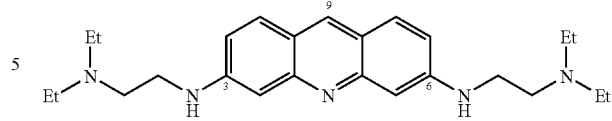

Although many are known, there remains a great need for potent telomerase inhibitors, anticancer agents, antiproliferative agents, etc. particularly for such compounds which offer one or more additional pharmacological advantages, such as:

(a) improved activity.
(b) improved selectivity (e.g., against tumour cells versus normal cells).
(c) complement the activity of other treatments (e.g., chemotherapeutic agents);
(d) reduced intensity of undesired side-effects;
(e) fewer undesired side-effects;
(f) simpler methods of administration;
(g) reduction in required dosage amounts;
(h) reduction in required frequency of administration;
(i) increased ease of synthesis, purification, handling, storage, etc.;
(j) reduced cost of synthesis, purification, handling, storage, etc.

For example, particularly preferred telomerase inhibitors are ones which are characterized by one or more of the following properties:

(a) no inhibition of Taq polymerase at 10–50 μM (in order to provide specificity and eliminate broad-spectrum polymerase inhibitors);

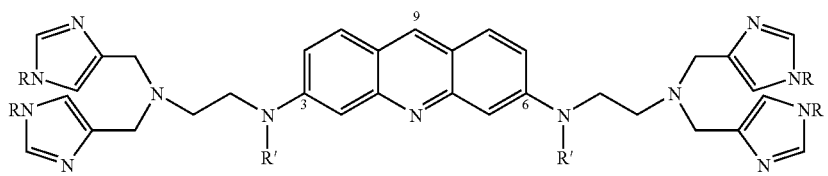

(b) cell free telomerase inhibition (at <1 μM) at concentrations more than 5 to 10-fold less than for concentrations for acute cytotoxicity;
(c) shortening of telomere length in tumour cells at concentrations 5 to 10-fold less than concentrations for acute cytotoxicity;
(d) telomere shortening in human tumour xenografts; and,
(e) oral bioavailability.

Thus, one aim of the present invention is the provision of compounds which are telomerase inhibitors, anticancer agents, antiproliferative agents, etc. which offer one or more of the above advantages and properties.

SUMMARY OF THE INVENTION

One aspect of the invention pertains to active acridine and acridine compounds, as described herein.

Another aspect of the invention pertains to active acridine and acridine compounds, as described herein, which inhibit telomerase.

Another aspect of the invention pertains to active compounds, as described herein, which treat conditions which are known to be mediated by telomerase, or which are known to be treated by telomerase inhibitors.

Another aspect of the invention pertains to active compounds, as described herein, which (a) regulate (e.g., inhibit) cell proliferation; (b) inhibit cell cycle progression; (c) promote apoptosis; or (d) a combination of one or more of these.

Another aspect of the invention pertains to active compounds, as described herein, which are anti-telomerase agents, and which treat a condition mediated by telomerase.

Another aspect of the invention pertains to active compounds, as described herein, which are anticancer agents, and which treat cancer.

Another aspect of the invention pertains to active compounds, as described herein, which are antiproliferative agents, and which treat a proliferative condition.

Another aspect of the present invention pertains to a composition comprising a compound as described herein and a pharmaceutically acceptable carrier.

Another aspect of the present invention pertains to methods of inhibiting telomerase in a cell, comprising contacting said cell with an effective amount of an active compound, as described herein.

Another aspect of the present invention pertains to methods of (a) regulating (e.g., inhibiting) cell proliferation; (b) inhibiting cell cycle progression; (c) promoting apoptosis; or (d) a combination of one or more of these, comprising contacting a cell with an effective amount of an active compound, as described herein, whether in vitro or in vivo.

Another aspect of the present invention pertains to methods of treating a condition which is known to be mediated by telomerase, or which is known to be treated by telomerase inhibitors, comprising administering to a subject in need of treatment a therapeutically-effective amount of an active compound, as described herein.

Another aspect of the present invention pertains to methods of treating cancer, comprising administering to a subject in need of treatment a therapeutically-effective amount of an active compound, as described herein.

Another aspect of the present invention pertains to methods of treating a proliferative condition comprising administering to a subject in need of treatment a therapeutically-effective amount of an active compound, as described herein.

Another aspect of the present invention pertains to an active compound, as described herein, for use in a method of treatment of the human or animal body by therapy.

Another aspect of the present invention pertains to use of an active compound, as described herein, for the manufacture of a medicament for use in the treatment of a condition mediated by telomerase, cancer, a proliferative condition, or other condition as described herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

Figure 1:
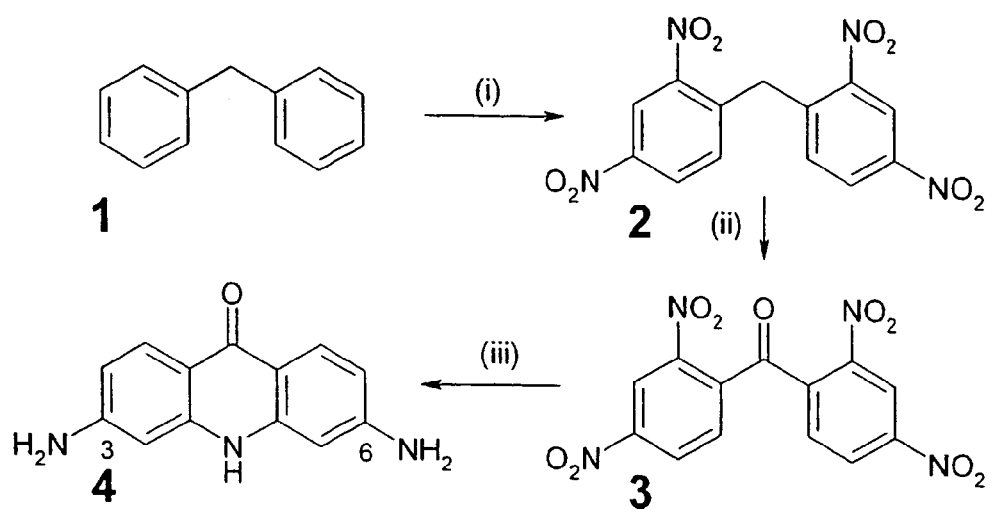
FIG. 1 is a scheme illustrating a chemical synthesis method for 3,6-diamino-acridone.

The present invention pertains generally to a class of compounds referred to herein as "acridines" and "acridines" which have the following general formula:

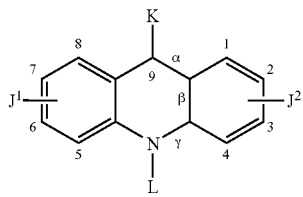

(1)

wherein either:
(a) K is =O, L is —H, α is a single bond, β is a double bond, γ is a single bond (i.e., "acridines"); or:
(b) K is a 9-substituent, L is absent, α is a double bond, β is a single bond, γ is a double bond (i.e., "acridines");

and wherein:
$J^1$ is a 2- or 3-substituent; and,
$J^2$ is a 6- or 7-substituent;

and wherein $J^1$ and $J^2$ are each independently a group of the formula:

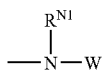

wherein:
$R^{N1}$ is independently a nitrogen substituent and is hydrogen, $C_{1-7}$alkyl, $C_{3-20}$heterocyclyl, or $C_{5-20}$aryl, and is optionally substituted; and,
W is independently $C_{1-7}$alkyl, $C_{3-20}$heterocyclyl, or $C_{5-20}$aryl, and is optionally substituted;

and wherein, when K is a 9-substituent, K is a group of the formula:

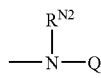

wherein:
$R^{N2}$ is independently a nitrogen substituent and is hydrogen, $C_{1-7}$alkyl, $C_{3-20}$heterocyclyl, or $C_{5-20}$aryl, and is optionally substituted; and,
Q is independently $C_{1-7}$alkyl, $C_{3-20}$heterocyclyl, or $C_{5-20}$aryl, and is optionally substituted;

and pharmaceutically acceptable salts, esters, amides, solvates, hydrates, and protected forms thereof.

As will be appreciated by the skilled artisan, the above structure is one of many possible resonance structures which may be drawn to depict the same compound. As used herein, a reference to one such structure is to be considered a reference to all possible corresponding resonance structures.

In another embodiment, the compounds are "acridines" of the following formula:

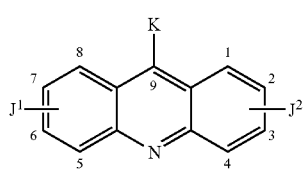

(2)

In one embodiment, the compounds are "acridines" of the following formula:

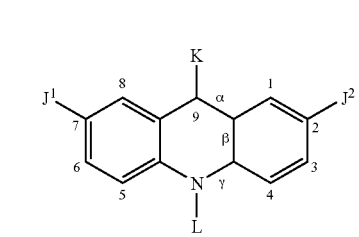

(3)

For the avoidance of doubt, the phrase "optionally substituted," as used herein, is synonymous with the phrase "is unsubstituted or substituted."

Side Chains, $J^1$ and $J^2$

In one embodiment, whether acridine or acridone, $J^1$ is a 2-substituent and $J^2$ is a 7-substituent (i.e., 2,7-disubstituted).

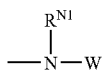

(4)

In one embodiment, whether acridine or acridone, $J^1$ is a 3-substituent and $J^2$ is a 6-substituent (i.e., 3,6-disubstituted).

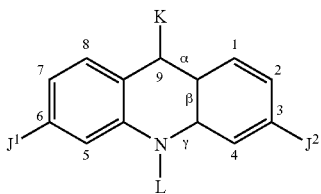

(5)

These embodiments may conveniently be referred to as "symmetrical" compounds.

In one embodiment, whether acridine or acridone, $J^1$ is a 2-substituent and $J^2$ is a 6-substituent (i.e., 2,6-disubstituted), or, equivalently, $J^1$ is a 3-substituent and $J^2$ is a 7-substituent (i.e., 3,7-disubstituted).

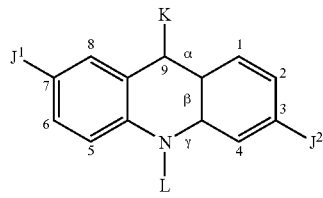

(6)

These embodiments may conveniently be referred to as "non-symmetrical" compounds.

In one preferred embodiment, $J^1$ and $J^2$ are the same.

Side Chains, $J^1$ and $J^2$: —N($R^{N1}$)—W

In the compounds of the present invention, $J^1$ and $J^2$ are each independently a group of the formula:

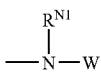

wherein:
$R^{N1}$ is independently a nitrogen substituent and is hydrogen, $C_{1-7}$alkyl, $C_{3-20}$heterocyclyl, or $C_{5-20}$aryl, and is optionally substituted; and, W is independently $C_{1-7}$alkyl, $C_{3-20}$heterocyclyl, or $C_{5-20}$aryl, and is optionally substituted.

Note that it is not intended that, through substitution on W, the nitrogen atom forms part of a larger functional group. For example, it is not intended that the group —N($R^{N1}$)— be connected to an oxo- or thione-substituted carbon atom of W (i.e., —C(=O)— or —C(=S)—, respectively), thereby forming an amide (i.e., —N($R^{N1}$)C(=O)—) or a thioamide (i.e., —N($R^{N1}$)C(=S)—), respectively.

Side Chains, $J^1$ and $J^2$: Alkyl

In one embodiment, W is independently $C_{1-7}$alkyl, $C_{3-20}$heterocyclyl, or $C_{5-20}$aryl, and is optionally substituted.

In one embodiment, W is independently $C_{1-7}$alkyl, $C_{3-20}$heterocyclyl, or $C_{5-20}$aryl, and is optionally substituted with one or more groups selected from: amino; ether (e.g., $C_{1-7}$alkoxy); amido; acylamino; carboxy; ester; acyloxy; and sulfonamido.

In one embodiment, W is independently $C_{1-7}$alkyl and is optionally substituted.

In one embodiment, W is independently $C_{1-7}$alkyl, and is optionally substituted with one or more groups selected from: amino; ether (e.g., $C_{1-7}$alkoxy); amido; acylamino; carboxy; ester; acyloxy; and sulfonamido.

In one embodiment, W is independently $C_{1-7}$alkyl and is optionally substituted with one or more groups selected from: amino and ether (e.g., $C_{1-7}$alkoxy).

In one embodiment, W is independently $C_{1-7}$alkyl substituted with one or more groups selected from: amino and ether (e.g., $C_{1-7}$alkoxy).

In one embodiment, W is independently $C_{1-7}$alkyl substituted with one or more group selected from: amino; ether; polyamino; polyether; and polyether-polyamino.

In one embodiment, W is independently a group of the formula:

wherein:
n is independently an integer from 1 to 8;
each m is independently an integer from 1 to 8;
s is independently an integer from 0 to 3;
each G is independently —O— or —$NR^N$—;
each $R^N$ is independently a nitrogen substituent;
T is independently a terminal amino group, —$NR^1R^2$ or a terminal ether group, —$OR^5$.

In one embodiment, the compounds have the following formula:

(7)

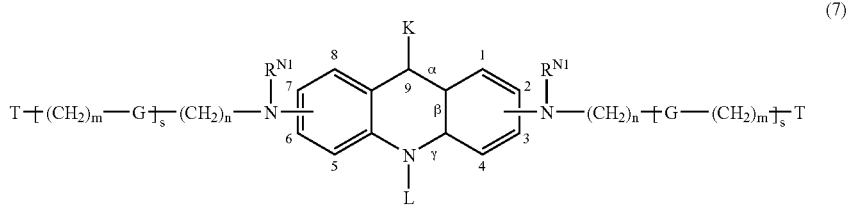

In one embodiment, the compounds are acridines, and have the following formula:

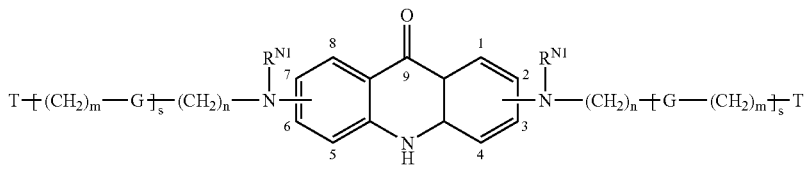

(8)

In one embodiment, the compounds are acridines, and have the following formula:

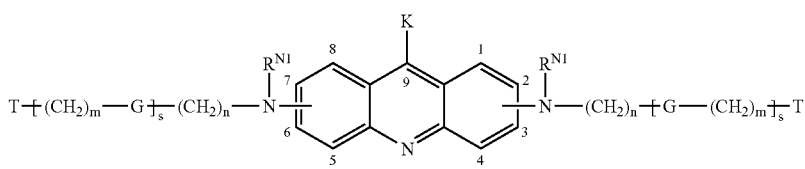

(9)

In one embodiment, s is independently an integer from 0 to 3.
In one embodiment, s is independently an integer from 0 to 2.
In one embodiment, s is independently 0 or 1.
In one embodiment, s is independently an integer from 1 to 3.
In one embodiment, s is independently 1 or 2.
In one embodiment, s is independently 3.
In one embodiment, s is independently 2.
In one embodiment, s is independently 1.
In one embodiment, s is independently 0.
In one embodiment, W is independently $C_{1-7}$alkyl substituted with one or more group selected from: amino; ether; amino-$C_{1-7}$alkyl-amino; amino-$C_{1-7}$alkoxy; and ether-$C_{1-7}$alkoxy.
In one embodiment, W is independently selected from:
amino-$C_{1-7}$alkyl;
ether-$C_{1-7}$alkyl;
amino-$C_{1-7}$alkyl-amino-$C_{1-7}$alkyl;
amino-$C_{1-7}$alkoxy-$C_{1-7}$alkyl; and,
ether-$C_{1-7}$alkoxy-$C_{1-7}$alkyl.
In one embodiment, W is independently selected from the following, wherein $-NR^1R^2$ is a terminal amino group, $-OR^5$ is a terminal ether group, $R^N$ is a nitrogen substituent, and each of n and m is independently an integer from 1 to 8:
—$(CH_2)_n$—$NR^1R^2$;
—$(CH_2)_n$—$OR^5$;
—$(CH_2)_n$—$NR^N$—$(CH_2)_m$—$NR^1R^2$;
—$(CH_2)_n$—$NR^N$—$(CH_2)_m$—$OR^5$;
—$(CH_2)_n$—O—$(CH_2)_m$—$NR^1R^2$; and,
—$(CH_2)_n$—O—$(CH_2)_m$—$OR^5$.
In one embodiment, n is independently an integer from 1 to 5.
In one embodiment, n is independently an integer from 1 to 4.
In one embodiment, n is independently an integer from 1 to 3.

In one embodiment, n is independently 1 or 2.
In one embodiment, n is independently 1.
In one embodiment, n is independently 2.
In one embodiment, n is independently 3.
In one embodiment, n is independently 4.
In one embodiment, n is independently 5.
In one embodiment, each m is independently an integer from 1 to 5.
In one embodiment, each m is independently an integer from 1 to 4.
In one embodiment, each m is independently an integer from 1 to 3.
In one embodiment, each m is independently 1 or 2.
In one embodiment, each m is independently 1.
In one embodiment, each m is independently 2.
In one embodiment, each m is independently 3.
In one embodiment, each m is independently 4.
In one embodiment, each m is independently 5.
In one embodiment, W is independently selected from the following, wherein $-NR^1R^2$ is a terminal amino group, $-OR^5$ is a terminal ether group, $R^N$ is a nitrogen substituent, and m is as defined above:
—$(CH_2)_2$—$NR^1R^2$,
—$(CH_2)_2$—$OR^5$;
—$(CH_2)_2$—$NR^N$—$(CH_2)_m$—$NR^1R^2$;
—$(CH_2)_2$—$NR^N$—$(CH_2)_m$—$OR^5$;
—$(CH_2)_2$—O—$(CH_2)_m$—$NR^1R^2$; and,
—$(CH_2)_2$—O—$(CH_2)_m$—$OR^5$;
—$(CH_2)_3$—$NR^1R^2$;
—$(CH_2)_3$—$OR^5$;
—$(CH_2)_3$—$NR^N$—$(CH_2)_m$—$NR^1R^2$;
—$(CH_2)_3$—$NR^N$—$(CH_2)_m$—$OR^5$;
—$(CH_2)_3$—O—$(CH_2)_m$—$NR^1R^2$; and,
—$(CH_2)_3$—O—$(CH_2)_m$—$OR^5$;
—$(CH_2)_4$—$NR^1R^2$;
—$(CH_2)_4$—$OR^5$;
—$(CH_2)_4$—$NR^N$—$(CH_2)_m$—$NR^1R^2$;
—$(CH_2)_4$—$NR^N$—$(CH_2)_m$—$OR^5$;
—$(CH_2)_4$—O—$(CH_2)_m$—$NR^1R^2$; and,
—$(CH_2)_4$—O—$(CH_2)_m$—$OR^5$.

In one embodiment, W is independently selected from the following, wherein —$NR^1R^2$ is a terminal amino group, —$OR^5$ is a terminal ether group, and $R^N$ is a nitrogen substituent:
  —$(CH_2)_2$—$NR^1R^2$;
  —$(CH_2)_2$—$OR^5$;
  —$(CH_2)_2$—$NR^N$—$(CH_2)_2$—$NR^1R^2$;
  —$(CH_2)_2$—$NR^N$—$(CH_2)_2$—$OR^5$;
  —$(CH_2)_2$—O—$(CH_2)_2$—$NR^1R^2$; and,
  —$(CH_2)_2$—O—$(CH_2)_2$—$OR^5$;
  —$(CH_2)_2$—$NR^N$—$(CH_2)_3$—$NR^1R^2$;
  —$(CH_2)_2$—$NR^N$—$(CH_2)_3$—$OR^5$;
  —$(CH_2)_2$—O—$(CH_2)_3$—$NR^1R^2$; and,
  —$(CH_2)_2$—O—$(CH_2)_3$—$OR^5$;
  —$(CH_2)_2$—$NR^N$—$(CH_2)_4$—$NR^1R^2$;
  —$(CH_2)_2$—$NR^N$—$(CH_2)_4$—$OR^5$;
  —$(CH_2)_2$—O—$(CH_2)_4$—$NR^1R^2$; and,
  —$(CH_2)_2$—O—$(CH_2)_4$—$OR^5$;
  —$(CH_2)_3$—$NR^1R^2$;
  —$(CH_2)_3$—$OR^5$;
  —$(CH_2)_3$—$NR^N$—$(CH_2)_2$—$NR^1R^2$;
  —$(CH_2)_3$—$NR^N$—$(CH_2)_2$—$OR^5$;
  —$(CH_2)_3$—O—$(CH_2)_2$—$NR^1R^2$; and,
  —$(CH_2)_3$—O—$(CH_2)_2$—$OR^5$;
  —$(CH_2)_3$—$NR^N$—$(CH_2)_3$—$NR^1R^2$;
  —$(CH_2)_3$—$NR^N$—$(CH_2)_3$—$OR^5$;
  —$(CH_2)_3$—O—$(CH_2)_3$—$NR^1R^2$; and,
  —$(CH_2)_3$—O—$(CH_2)_3$—$OR^5$;
  —$(CH_2)_3$—$NR^N$—$(CH_2)_4$—$NR^1R^2$;
  —$(CH_2)_3$—$NR^N$—$(CH_2)_4$—$OR^5$;
  —$(CH_2)_3$—O—$(CH_2)_4$—$NR^1R^2$; and,
  —$(CH_2)_3$—O—$(CH_2)_4$—$OR^5$;
  —$(CH_2)_4$—$NR^1R^2$;
  —$(CH_2)_4$—$OR^5$;
  —$(CH_2)_4$—$NR^N$—$(CH_2)_2$—$NR^1R^2$;
  —$(CH_2)_4$—$NR^N$—$(CH_2)_2$—$OR^5$;
  —$(CH_2)_4$—O—$(CH_2)_2$—$NR^1R^2$;and,
  —$(CH_2)_4$—O—$(CH_2)_2$—$OR^5$;
  —$(CH_2)_4$—$NR^N$—$(CH_2)_3$—$NR^1R^2$;
  —$(CH_2)_4$—$NR^N$—$(CH_2)_3$—$OR^5$;
  —$(CH_2)_4$—O—$(CH_2)_3$—$NR^1R^2$; and,
  —$(CH_2)_4$—O—$(CH_2)_3$—$OR^5$;
  —$(CH_2)_4$—$NR^N$—$(CH_2)_4$—$NR^1R^2$;
  —$(CH_2)_4$—$NR^N$—$(CH_2)_4$—$OR^5$;
  —$(CH_2)_4$—O—$(CH_2)_4$—$NR^1R^2$; and,
  —$(CH_2)_4$—O—$(CH_2)_4$—$OR^5$.

In one embodiment, W is independently selected from the following, wherein —$NR^1R^2$ is a terminal amino group, —$OR^5$ is a terminal ether group, and n is as defined above:
  —$(CH_2)_n$—$NR^1R^2$; and,
  —$(CH_2)_n$—$OR^5$.

In one embodiment, W is independently selected from the following, wherein —$NR^1R^2$ is a terminal amino group, and —$OR^5$ is a terminal ether group:
  —$(CH_2)_2$—$NR^1R^2$; and,
  —$(CH_2)_2$—$OR^5$;
  —$(CH_2)_3$—$NR^1R^2$; and,
  —$(CH_2)_3$—$OR^5$;
  —$(CH_2)_4$—$NR^1R^2$; and,
  —$(CH_2)_4$—$OR^5$.

In one embodiment, W is independently selected from the following, wherein —$NR^1R^2$ is a terminal amino group:
  —$(CH_2)_2$—$NR^1R^2$;
  —$(CH_2)_3$—$NR^1R^2$; and,
  —$(CH_2)_4$—$NR^1R^2$.

Terminal Amino Groups, —$NR^1R^2$

The term "terminal amino group," as used herein, pertains to an amino group of the formula —$NR^1R^2$, wherein each of $R^1$ and $R^2$ is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

In one embodiment, the terminal amino group, —$NR^1R^2$, is a secondary amino group, and one of $R^1$ and $R^2$ is —H.

In one embodiment, the terminal amino group, —$NR^1R^2$, is a tertiary amino group, and neither $R^1$ nor $R^2$ is —H.

In one embodiment, the terminal amino group, —$NR^1R^2$, is a tertiary amino group, neither $R^1$ nor $R^2$ is —H, and $R^1$ and $R^2$ are the same.

In one embodiment, the terminal amino group, —$NR^1R^2$, is a tertiary amino group, neither $R^1$ nor $R^2$ is —H, and $R^1$ and $R^2$ are different.

In one embodiment, each of $R^1$ and $R^2$ is independently $C_{5-20}$aryl, and is optionally substituted.

In one embodiment, at least one of $R^1$ and $R^2$ is independently $C_{5-20}$aryl, and is optionally substituted.

In one embodiment, each of $R^1$ and $R^2$ is independently $C_{5-20}$heteroaryl, and is optionally substituted.

In one embodiment, at least one of $R^1$ and $R^2$ is independently $C_{5-20}$heteroaryl, and is optionally substituted.

In one embodiment, each of $R^1$ and $R^2$ is independently $C_{5-20}$carboaryl, and is optionally substituted.

In one embodiment, each of $R^1$ and $R^2$ is independently phenyl, and is optionally substituted.

In one embodiment, at least one of $R^1$ and $R^2$ is independently phenyl, and is optionally substituted.

In one embodiment, each of $R^1$ and $R^2$ is independently $C_{1-7}$alkyl, and is optionally substituted.

In one embodiment, at least one of $R^1$ and $R^2$ is independently $C_{1-7}$alkyl, and is optionally substituted.

In one embodiment, each of $R^1$ and $R^2$ is independently aliphatic saturated $C_{1-7}$alkyl, and is optionally substituted.

In one embodiment, each of $R^1$ and $R^2$ is independently aliphatic saturated unsubstituted $C_{1-7}$alkyl.

In one embodiment, each of $R^1$ and $R^2$ is independently -Me, -Et, -nPr, -iPr, -nBu, or -tBu.

In one embodiment, the terminal amino group, —$NR^1R^2$, is independently —$N(Me)_2$, —$N(Et)_2$, —$N(nPr)_2$, —$N(iPr)_2$, —$N(nBu)_2$, or —$N(tBu)_2$.

In one embodiment, $R^2$ is H and $R^1$ and is independently $C_{1-7}$alkyl, and is optionally substituted.

In one embodiment, $R^2$ is H and $R^1$ and is independently aliphatic saturated $C_{1-7}$alkyl, and is optionally substituted.

In one embodiment, $R^2$ is H and $R^1$ and is independently aliphatic saturated unsubstituted $C_{1-7}$alkyl.

In one embodiment, $R^2$ is H and $R^1$ and is independently -Me, -Et, -nPr, -iPr, -nBu, or -tBu.

In one embodiment, the terminal amino group, —$NR^1R^2$, is independently —NHMe, —NHEt, —NH(nPr), —NH(iPr), —NH(nBu), or —NH(tBu).

Alternatively, $R^1$ and $R^2$, taken together with the nitrogen atom to which they are attached, may form a heterocyclic ring having from 3 to 8 ring atoms (e.g., a $C_{3-8}$heterocyclyl group), more preferably 5 to 8 ring atoms (e.g., a $C_{5-8}$heterocyclyl group), which heterocyclic ring may be saturated, partially unsaturated, or fully unsaturated, and is optionally substituted.

In one embodiment, $R^1$ and $R^2$, taken together with the nitrogen atom to which they are attached, form a saturated heterocyclic ring having from 3 to 8 ring atoms (e.g., a $C_{3-8}$heterocyclyl group), more preferably 5 to 8 ring atoms (e.g., a $C_{5-8}$heterocyclyl group), which heterocyclic ring is optionally substituted.

In one embodiment, $R^1$ and $R^2$, taken together with the nitrogen atom to which they are attached, form a saturated heterocyclic ring having from 3 to 8 ring atoms (e.g., a $C_{3-8}$heterocyclyl group), more preferably 5 to 8 ring atoms (e.g., a $C_{5-8}$heterocyclyl group), wherein only one of said ring atoms is nitrogen, and all others are carbon, and which heterocyclic ring is optionally substituted.

In one embodiment, $R^1$ and $R^2$, taken together with the nitrogen atom to which they are attached form a cyclic amino group of the following formula, wherein q is independently an integer from 2 to 7, and wherein said group is optionally substituted:

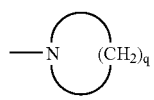

In one embodiment, q is independently an integer from 3 to 7.

In one embodiment, q is independently an integer from 4 to 7.

In one embodiment, q is independently an integer from 4 to 6.

In one embodiment, q is independently 4 or 5.

In one embodiment, the terminal amino group, $-NR^1R^2$, is independently one of the following cyclic amino groups, and is optionally substituted:

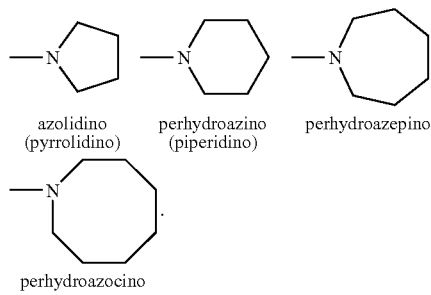

In one embodiment, $R^1$ and $R^2$, taken together with the nitrogen atom to which they are attached, form a heterocyclic ring having from 3 to 8 ring atoms (e.g., a $C_{3-8}$heterocyclyl group), more preferably 5 to 8 ring atoms (e.g., a $C_{3-8}$heterocyclyl group), wherein said ring has at least two heteroatoms selected from nitrogen, oxygen, and sulfur, which heterocyclic ring may saturated, partially unsaturated, or fully unsaturated, and is optionally substituted.

In one embodiment, $R^1$ and $R^2$, taken together with the nitrogen atom to which they are attached, form a saturated heterocyclic ring having from 3 to 8 ring atoms (e.g., a $C_{3-8}$heterocyclyl group), more preferably 5 to 8 ring atoms (e.g., a $C_{3-8}$heterocyclyl group), wherein said ring has at least two heteroatoms selected from nitrogen, oxygen, and sulfur, which heterocyclic ring is optionally substituted.

In one embodiment, the terminal amino group, $-NR^1R^2$, is one of the following groups, and is optionally substituted:

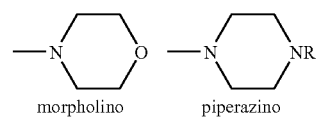

wherein R is an amino substituent, for example, hydrogen, $C_{1-7}$alkyl, $C_{3-20}$heterocyclyl, or $C_{5-20}$aryl.

In one embodiment, $-NR^1R^2$, is piperazino, and R is -Me or -Et.

When $R^1$ and $R^2$, taken together with the nitrogen atom, form a heterocyclic ring, the ring may optionally be bridged, fused, and/or spiro in nature, and is optionally substituted. An example of such a terminal amino group, $-NR^1R^2$, is shown below:

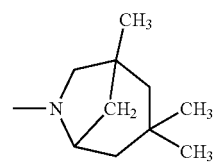

As mentioned above, the groups $R^1$ and $R^2$, or the heterocyclic ring formed from $R^1$ and $R^2$ and the nitrogen atom to which they are attached, are optionally substituted. For example, in one embodiment, $R^1$ and $R^2$ and the nitrogen atom to which they are attached form a cyclic amino group, $-NR^1R^2$, which has one or more substituents selected from: $C_{1-7}$alkyl, $C_{3-20}$aryl-$C_{1-7}$alkyl, $C_{3-20}$aryl, $C_{1-7}$alkyl-$C_{3-20}$aryl, hydroxy $C_{1-7}$hydroxyalkyl, and $C_{1-7}$aminoalkyl.

In one embodiment, $R^1$ and $R^2$ and the nitrogen atom to which they are attached form a cyclic amino group, $-NR^1R^2$, which has one or more substituents selected from: -Me, -Et, $-CH_2Ph$, $-OH$, $-CH_2OH$, $-CH_2CH_2OH$, $-CH_2NH_2$, and $-CH_2CH_2NH_2$.

In one embodiment, the terminal amino group, $-NR^1R^2$, is one of the following substituted cyclic amino groups:

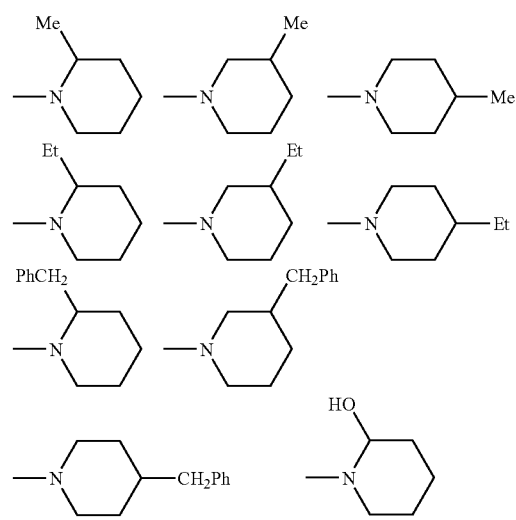

-continued

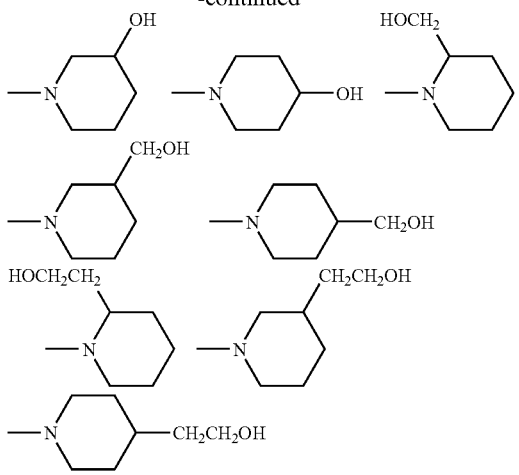

Terminal Ether Substituents

The term "terminal ether group," as used herein, pertains to an ether group of the formula —$OR^5$, wherein $R^5$ is independently an ether substituent, and is selected from: hydrogen, $C_{1-7}$alkyl, $C_{3-20}$heterocyclyl, and $C_{5-20}$aryl; and is optionally substituted.

In one embodiment, $R^5$ is independently —H.

In one embodiment, $R^5$ is independently not —H.

In one embodiment, $R^5$ is independently $C_{1-7}$alkyl, $C_{3-20}$heterocyclyl, and $C_{5-20}$aryl; and is optionally substituted.

In one embodiment, $R^5$ is independently $C_{1-7}$alkyl, and is optionally substituted.

In one embodiment, $R^5$ is independently aliphatic $C_{1-7}$alkyl, and is optionally substituted.

In one embodiment, $R^5$ is independently aliphatic $C_{1-7}$alkyl, and is unsubstituted.

In one embodiment, $R^5$ is independently aliphatic saturated $C_{1-7}$alkyl, and is optionally substituted.

In one embodiment, $R^5$ is independently aliphatic saturated $C_{1-7}$alkyl, and is unsubstituted.

In one embodiment, $R^5$ is independently -Me, -Et, -nPr, -iPr, -nBu, or -tBu.

In one embodiment, $R^5$ is independently $C_{5-20}$aryl, and is optionally substituted.

In one embodiment, $R^5$ is independently $C_{5-20}$carboaryl, and is optionally substituted.

In one embodiment, $R^5$ is independently $C_{5-20}$heteroaryl, and is optionally substituted.

In one embodiment, $R^5$ is independently phenyl, and is optionally substituted.

In one embodiment, $R^5$ is independently -Me, -Et, -nPr, -iPr, -nBu, -tBu, or optionally substituted -Ph.

In one embodiment, $R^5$ is independently -Me, -Et, -nPr, -iPr, -nBu, -tBu, optionally substituted -Ph, or optionally substituted -Bn.

9-Substituents, K

In the above acridine compounds, wherein K is a 9-substituent, K is independently a group of the formula;

wherein:

$R^{N2}$ is independently a nitrogen substituent and is hydrogen, $C_{1-7}$alkyl, $C_{3-20}$heterocyclyl, or $C_{5-20}$aryl, and is optionally substituted; and, Q is independently $C_{1-7}$alkyl, $C_{3-20}$heterocyclyl, or $C_{5-20}$aryl, and is optionally substituted.

Thus, in one embodiment, the compounds are "acridines" of the following formula:

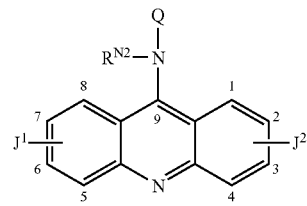

(10)

In one embodiment, the compounds are acridines, and have the following formula:

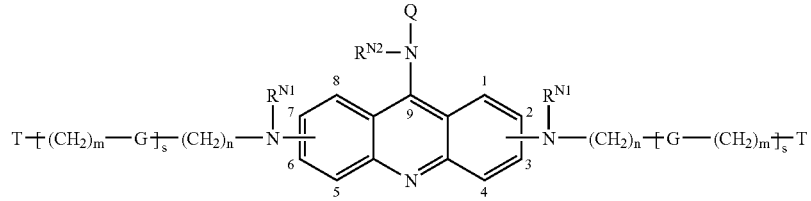

(11)

The Moiety, Q, as Optionally Substituted Aryl Group

In one embodiment, when K is a 9-substituent, Q is independently a $C_{5-20}$aryl group, and is optionally substituted.

In one embodiment, when K is a 9-substituent, Q is independently a $C_6$aryl group (e.g., $C_6$carboaryl or $C_6$heteroaryl), and is optionally substituted.

In one embodiment, when K is a 9-substituent, Q is independently an azinyl (pyridyl) group, and is optionally substituted, and K is a group of the formula:

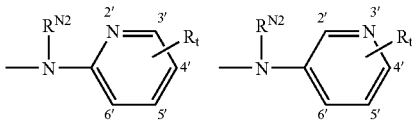

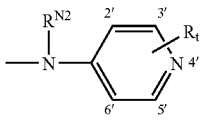

wherein t is independently an integer from 0 to 4, and each R is independently a substituent as defined herein.

In one embodiment, when K is a 9-substituent, Q is independently a substituted diazinyl (e.g., pyridazinyl, pyrimidinyl, pyrazinyl) group, and is optionally substituted, and K is, for example, a group having one of the following formulae:

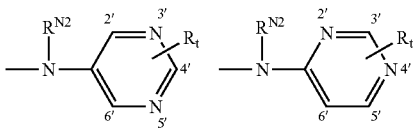

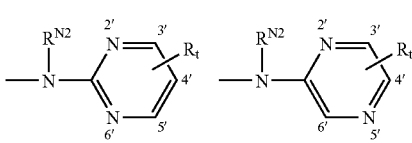

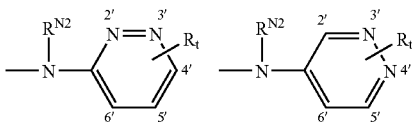

wherein t is independently an integer from 0 to 3, and each R is independently a substituent as defined herein.

In one embodiment, when K is a 9-substituent, Q is independently a phenyl group, and is optionally substituted, and K is a group of the formula:

$R^{N2}$—N
(phenyl with positions 2', 3', 4', 5', 6' and $R_t$)

wherein t is independently an integer from 0 to 5, and each R is independently a substituent as defined herein.

In this embodiment, the acridine compounds have the formula:

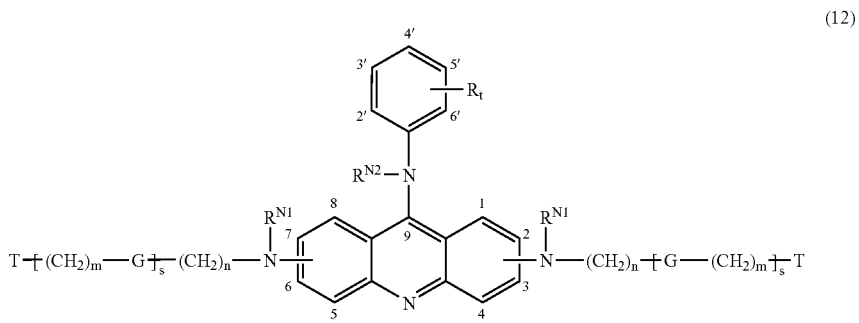

(12)

In one embodiment, t is independently an integer from 0 to 4.

In one embodiment, t is independently an integer from 0 to 3.

In one embodiment, t is independently an integer from 0 to 2.

In one embodiment, t is independently 0 or 1.

In one embodiment, t is independently an integer from 1 to 5.

In one embodiment, t is independently an integer from 1 to 4.

In one embodiment, t is independently an integer from 1 to 3.

In one embodiment, t is independently 1 or 2.

In one embodiment, t is independently 5.

In one embodiment, t is independently 4.

In one embodiment, t is independently 3.

In one embodiment, t is independently 2.

In one embodiment, t is independently 1.

In one embodiment, t is independently 0.

If the phenyl group has less than the full complement of ring substituents, R, they may be arranged in any combination. For example, if m is 1, R may be in the 2'-, 3'-, 4'-, 5'-, or 6'-position. Similarly, if m is 2, the two R groups may be in, for example, the 2',3-, 2',4'-, 2',5'-, 2',6'-, 3',4'-, or 3',5'-positions. If m is 3, the three R groups may be in, for example, the 2',3',4'-, 2',3',5'-, 2',3',6'-, or 3',4', 5'-positions.

Examples of some preferred phenyl substituents include, but are not limited to, halo, amino, hydroxy, ether (e.g., $C_{1-7}$alkoxy), thio, thioether (e.g., $C_{1-7}$alkylthio), $C_{1-7}$alkyl, $C_{1-7}$haloalkyl, acyl (e.g., $C_{1-7}$alkylacyl), amido (e.g., $C_{1-7}$alkylamido), carboxy, cyano, and aminoalkyl.

Examples of substituted phenyl groups which are suitable as Q include, but are not limited to, the following:

monohalophenyl, for example,
4'-fluorophenyl, 3'-fluorophenyl, 2'-fluorophenyl;
4'-chlorophenyl, 3'-chlorophenyl, 2'-chlorophenyl;
4'-bromophenyl, 3'-bromophenyl, 2'-bromophenyl.

dihalophenyl, for example,
2',3'-difluorophenyl, 2',3'-dichlorophenyl;
2',4'-difluorophenyl, 2',4'-dichlorophenyl;
2',5'-difluorophenyl, 2',5'-dichlorophenyl;
3',4'-difluorophenyl, 3',4'-dichlorophenyl;
3',5'-difluorophenyl, 3',5'-dichlorophenyl.

monoaminophenyl, for example,
4'-aminophenyl, 3'-aminophenyl, 2'-aminophenyl.

diaminophenyl, for example,
2',3'-diaminophenyl, 2',4'-diaminophenyl, 2',5'-diaminophenyl,
3',4'-diaminophenyl, 3',5'-diaminophenyl.

monohydroxyphenyl, for example,
4'-hydroxyphenyl, 3'-hydroxyphenyl, 2'-hydroxyphenyl.

monomethoxyphenyl, for example,
4'-methoxyphenyl, 3'-methoxyphenyl, 2'-methoxyphenyl.

monothiophenyl, for example,
4'-thiophenyl, 3'-thiophenyl, 2'-thiophenyl.

monomethylthiophenyl, for example,
4'-methylthiophenyl, 3'-methylthiophenyl, 2'-methylthiophenyl.

monomethylphenyl, for example,
4'-methylphenyl, 3'-methylphenyl, 2'-methylphenyl.

monotrifluoromethylphenyl, for example,
4'-trifluoromethylphenyl, 3'-trifluoromethylphenyl, 2'-trifluoromethylphenyl.

monoacetylphenyl, for example,
4'-acetylphenyl, 3'-acetylphenyl, 2'-acetylphenyl.

monoamidophenyl, for example,
4'-amidophenyl, 3'-amidophenyl, 2'-amidophenyl.
4'-(methylamido)phenyl, 3'-(methylamido)phenyl, 2'-(methylamido)phenyl.

monocarboxyphenyl, for example,
4'-carboxyphenyl, 3'-carboxyphenyl, 2'-carboxyphenyl.

monocyanophenyl, for example,
4'-cyanophenyl, 3'-cyanophenyl, 2'-cyanophenyl.

mono(aminoalkyl)phenyl, for example,
4'-aminoalkylphenyl, 3'-aminoalkylphenyl, 2'-aminoalkylphenyl;
4'-aminomethylphenyl, 3'-aminomethylphenyl, 2'-aminomethylphenyl;
4'-aminoethylphenyl, 3'-aminoethylphenyl, 2'-aminoethylphenyl.

monohalo-mono(aminoalkyl)phenyl, for example,
2'-halo-4'-aminoalkylphenyl, 2'-halo-3'-aminoalkylphenyl,
3'-halo-2'-aminoalkylphenyl, 3'-halo-4'-aminoalkylphenyl,
4'-halo-2'-aminoalkylphenyl, 4'-halo-3'-aminoalkylphenyl.

In one embodiment, when K is a 9-substituent, Q is a 4'-aminophenyl group, and K is a group of the formula:

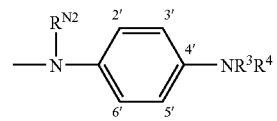

wherein $-NR^3R^4$ is as defined above for $-NR^1R^2$.

In this embodiment, the acridine compounds have the formula:

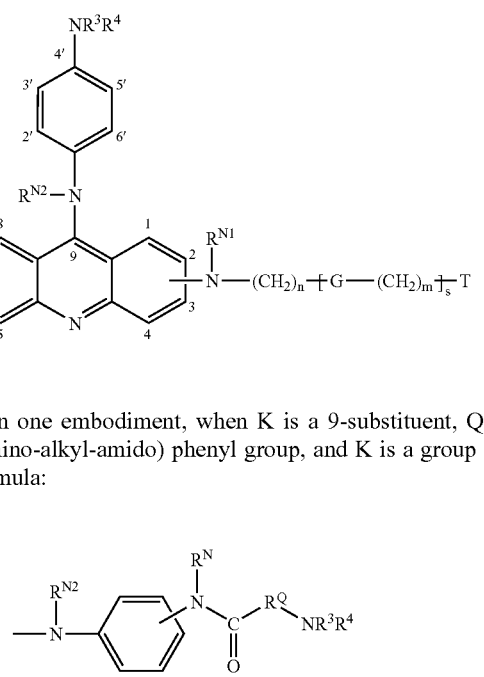

(13)

In one embodiment, when K is a 9-substituent, Q is an (amino-alkyl-amido) phenyl group, and K is a group of the formula:

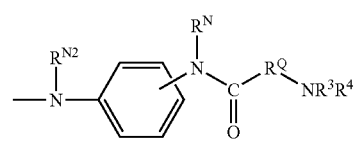

wherein $R^N$ is a nitrogen substituent as defined for $R^{N2}$, $R^Q$ is independently a $C_{1-10}$alkylene group, and $-NR^3R^4$ is as defined above for $-NR^1R^2$.

In one embodiment, when K is a 9-substituent, Q is a 4'-(amino-alkyl-amido) phenyl group, and K is a group of the formula:

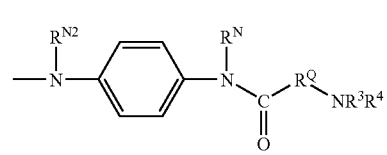

wherein $R^N$ is a nitrogen substituent as defined for $R^{N2}$, $R^Q$ is independently a $C_{1-10}$alkylene group, and —$NR^3R^4$ is as defined above for —$NR^1R^2$.

In one embodiment, when K is a 9-substituent, $R^Q$ is —$(CH_2)_p$—, wherein p is independently an integer from 1 to 8, and K has the following formula:

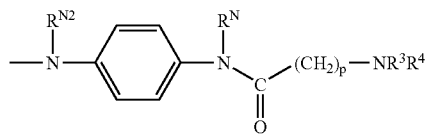

wherein $R^N$ is a nitrogen substituent as defined for $R^{N2}$, and —$NR^3R^4$ is as defined above for —$NR^1R^2$.

In this embodiment, the acridine compounds have the formula:

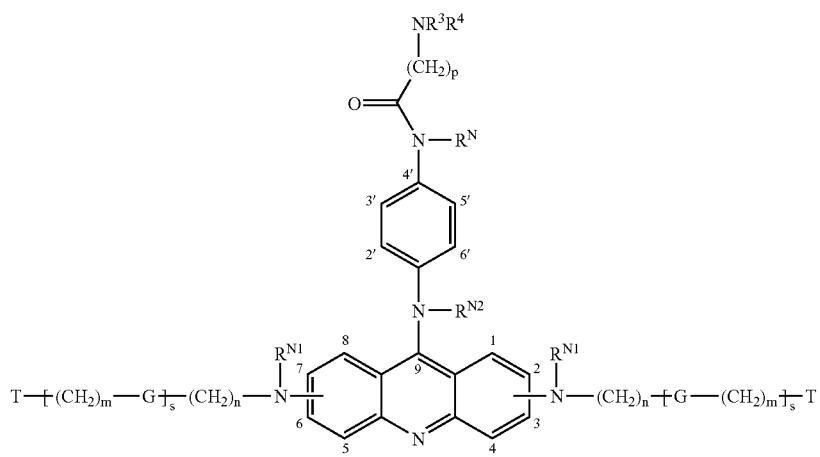

In one embodiment, p is independently an integer from 1 to 8.

In one embodiment, p is independently an integer from 1 to 6.

In one embodiment, p is independently an integer from 1 to 4.

In one embodiment, p is independently an integer from 2 to 6.

In one embodiment, p is independently an integer from 2 to 4.

In one embodiment, p is independently 2 or 3.

In one embodiment, p is independently 2, and K is a group of the formula, wherein $R^N$ is a nitrogen substituent as defined for $R^{N2}$, and —$NR^3R^4$ is as defined above for —$NR^1R^2$:

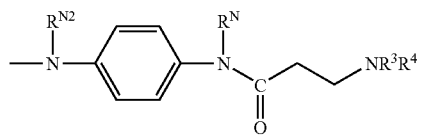

In one embodiment, K is a group of the formula:

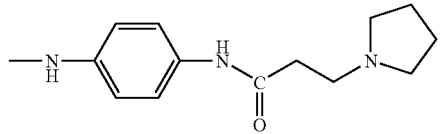

In one embodiment, when K is a 9-substituent, Q is a certain substituted phenyl group, and K is a group of the formula:

(14)

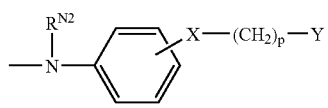

wherein:
X is —$N(R^N)$—, —$CH_2$—, —O—, or —S—;
$R^N$ is a nitrogen substituent as defined for $R^{N2}$;
Y is —OH, —$OR^Y$, or —$NR^3R^4$;
—$OR^Y$ is as defined above for —$OR^5$;
—$NR^3R^4$ is as defined above for —$NR^1R^2$; and,
p is independently an integer from 1 to 8, as defined above.

In one embodiment, the substituent is positioned para, and K is a group of the formula:

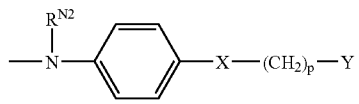

In one embodiment, X is —N(R$^N$)—, —CH$_2$—, —O—, or —S—, and Y is —NR$^3$R$^4$.

In one embodiment, X is —O—, or —S—, and Y is —OH, —OR$^Y$, or —NR$^3$R$^4$.

In one embodiment, X is —O—, or —S—, and Y is —NR$^3$R$^4$.

In one embodiment, X is —O—, and Y is —NR$^3$R$^4$.

In one embodiment, X is —N(R$^N$) and Y is —OH, —OR$^Y$, or —NR$^3$R$^4$.

In one embodiment, X is —N(R$^N$) and Y is —NR$^3$R$^4$:

The Moiety, Q, as Optionally Substituted Alkyl Group

In one embodiment, when K is a 9-substituent, Q is independently a C$_{1-7}$alkyl group, and is optionally substituted.

In one embodiment, when K is a 9-substituent, Q is independently a C$_{1-7}$alkyl group optionally substituted with one or more amino groups, one or more hydroxy groups, one more ether groups, one or more carboxy groups, one or more C$_{3-20}$heterocyclyl groups, one or more C$_{5-20}$aryl groups, etc.

In one embodiment, when K is a 9-substituent, Q is independently a substituted C$_{1-7}$alkyl group, for example, a C$_{1-7}$alkyl group substituted with one or more amino groups, one or more hydroxy groups, one more ether groups, one or more carboxy groups, one or more C$_{3-20}$heterocyclyl groups, one or more C$_{5-20}$aryl groups, etc.

In one embodiment, when K is a 9-substituent, Q is independently an amino substituted C$_{1-7}$alkyl group, that is, a C$_{1-7}$alkyl group substituted with one or more amino groups.

In one embodiment, when K is a 9-substituent, Q is independently a hydroxy substituted C$_{1-7}$alkyl group, that is, a C$_{1-7}$alkyl group substituted with one or more hydroxy groups.

In one embodiment, when K is a 9-substituent, Q is independently an ether substituted C$_{1-7}$alkyl group, that is, a C$_{1-7}$alkyl group substituted with one or more ether groups. For example, Q may be —CH$_2$CH$_2$—OMe.

In one embodiment, when K is a 9-substituent, Q is independently a carboxy substituted C$_{1-7}$alkyl group, that is, a C$_{1-7}$alkyl group substituted with one or more carboxy groups.

In one embodiment, when K is a 9-substituent, Q is independently a C$_{3-20}$heterocyclyl substituted C$_{1-7}$alkyl group, that is, a C$_{1-7}$alkyl group substituted with one or more C$_{3-20}$heterocyclyl groups. For example, Q may be —CH$_2$CH$_2$—(N-methyl-pyrrolidin-2-yl).

In one embodiment, when K is a 9-substituent, Q is independently a C$_{5-20}$aryl substituted C$_{1-7}$alkyl group, that is, a C$_{1-7}$alkyl group substituted with one or more C$_{5-20}$aryl groups. For example, Q may be —CH$_2$CH$_2$—(pyrid-3-yl).

In one embodiment, when K is a 9-substituent, Q is independently an amino substituted aliphatic saturated C$_{1-7}$alkyl group, that is, an aliphatic saturated C$_{1-7}$alkyl group substituted with one or more amino groups.

In one embodiment, when K is a 9-substituent, Q is independently an amino substituted linear saturated C$_{1-7}$alkyl group, that is, a linear saturated C$_{1-7}$alkyl group substituted with one or more amino groups.

In one embodiment, when K is a 9-substituent, Q is independently a terminally amino substituted linear saturated C$_{1-7}$alkyl group, that is, a linear saturated C$_{1-7}$alkyl group substituted with a terminal amino group, and K is a group of the formula:

$$-\underset{\underset{R^{N2}}{|}}{N}-(CH_2)_p-NR^3R^4$$

wherein p is independently an integer from 1 to 8, and the group —NR$^3$R$^4$ is as defined above for —NR$^1$R$^2$.

In this embodiment, the acridine compounds have the formula:

(15)

$$T\text{-}[(CH_2)_m\text{-}G]_s\text{-}(CH_2)_n\text{-}\underset{R^{N1}}{N}\text{-}\underset{7}{\overset{8}{\bigcirc}}\overset{9}{\underset{N}{\bigcirc}}\overset{1}{\underset{3}{\bigcirc}}\text{-}\underset{R^{N1}}{N}\text{-}(CH_2)_n\text{-}[G\text{-}(CH_2)_m]_s\text{-}T$$

with 9-position substituent: $R^{N2}-N-(CH_2)_p-NR^3R^4$

In one embodiment, p is independently an integer from 1 to 8.

In one embodiment, p is independently an integer from 1 to 6.

In one embodiment, p is independently an integer from 1 to 4.

In one embodiment, p is independently an integer from 2 to 6.

In one embodiment, p is independently an integer from 2 to 4.

In one embodiment, p is independently 2 or 3.

In one embodiment, when K is a 9-substituent, Q is independently an amino substituted branched saturated C$_{1-7}$alkyl group, that is, a branched saturated C$_{1-7}$alkyl group substituted with one or more amino groups.

In one embodiment, when K is a 9-substituent, Q is independently an amino disubstituted branched saturated C$_{1-7}$alkyl group, that is, a branched saturated C$_{1-7}$alkyl group substituted with two amino groups.

In one embodiment, when K is a 9-substituent, Q is independently an amino disubstituted branched saturated C$_{1-7}$alkyl group, and K is a group of the formula:

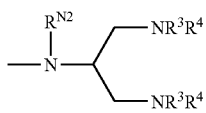

wherein each group —NR³R⁴ is as defined above for —NR¹R².

In one embodiment, when K is a 9-substituent, Q independently is, or comprises, an alicyclic saturated $C_{1-7}$alkyl group, and is optionally substituted. In one embodiment, Q is independently an alicyclic saturated $C_{1-7}$alkyl group, and is optionally substituted. In one embodiment, Q is independently a saturated $C_{1-7}$cycloalkyl-$C_{1-7}$alkyl group, and is optionally substituted.

In one embodiment, when K is a 9-substituent, Q independently is, or comprises, an alicyclic saturated $C_{1-7}$alkyl group, and K is a group of the formula:

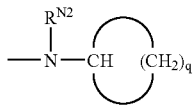

wherein q is independently an integer from 2 to 7 (as defined above), and wherein the cyclic group is optionally substituted. Examples of preferred substituents include halo, hydroxy, amino, and $C_{1-7}$alkyl.

In one embodiment, when K is a 9-substituent, Q independently is, or comprises, an alicyclic saturated $C_{1-7}$alkyl group, and K is a group of one of the following formulae:

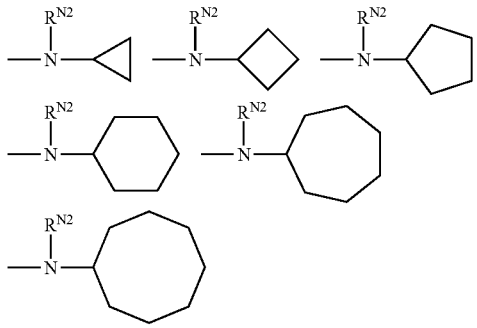

In one embodiment, when K is a 9-substituent, Q independently is, or comprises, an alicyclic saturated $C_{1-7}$alkyl group, and K is a group of the formula:

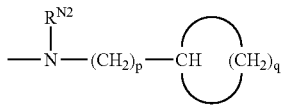

wherein p is independently an integer from 1 to 8 (as defined above) and q is independently an integer from 2 to 7 (as defined above), and wherein the cyclic group is optionally substituted. Examples of preferred substituents include halo, hydroxy, amino, and $C_{1-7}$alkyl.

In one embodiment, when K is a 9-substituent, Q independently is, or comprises, an alicyclic saturated $C_{1-7}$alkyl group, and K is a group of one of the following formulae:

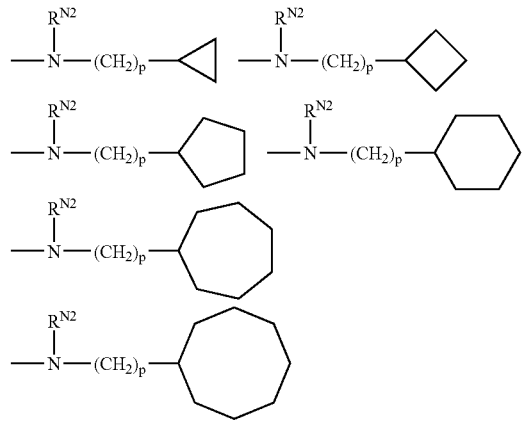

wherein p is independently an integer from 1 to 8 (as defined above), and wherein the cyclic group is optionally substituted.

Examples of other embodiments, when K is a 9-substituent, wherein Q is, or comprises, an alicyclic saturated $C_{1-7}$alkyl group, which is optionally substituted include the following:

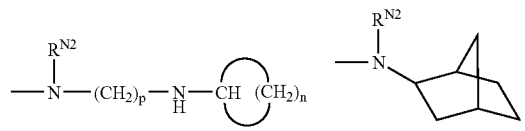

wherein p is independently an integer from 1 to 8 (as defined above), and n is independently an integer from 1 to 8 (as defined above).

In one embodiment, when K is a 9-substituent, Q is independently an amino, ether, polyamino, polyether, or polyaminoether group, and K is a group of the formula:

—N(R$^{N2}$)—(CH$_2$)$_n$—[G—(CH$_2$)$_m$]$_s$—T;

wherein n, m, s, G, and T are each independently as defined above.

Nitrogen Substituents: R$^{N1}$, R$^{N2}$, R$^{N}$

In one embodiment, each R$^{N1}$ is independently hydrogen, $C_{1-7}$alkyl, $C_{3-20}$heterocyclyl, or $C_{5-20}$aryl; and is optionally substituted.

In one embodiment, each R$^{N1}$ is independently hydrogen, $C_{1-7}$alkyl, $C_{5-12}$heterocyclyl, or $C_{5-12}$aryl; and is optionally substituted.

In one embodiment, each R$^{N1}$ is independently hydrogen, $C_{1-7}$alkyl, $C_{5-6}$heterocyclyl, or $C_{5-6}$aryl; and is optionally substituted.

In one embodiment, each R$^{N1}$ is independently hydrogen or $C_{1-7}$alkyl; and is optionally substituted.

In one embodiment, each R$^{N1}$ is independently hydrogen or aliphatic saturated $C_{1-7}$alkyl; and is optionally substituted.

In one embodiment, each R$^{N1}$ is independently hydrogen or aliphatic saturated $C_{1-7}$alkyl; and is unsubstituted.

In one embodiment, each $R^{N1}$ is independently —H, -Me, -Et, -nPr, -iPr, or -tBu.

In one embodiment, each $R^{N1}$ is independently —H, -Me, -Et, -nPr, -iPr, -tBu, -Bn, or -Ph.

In one embodiment, each $R^{N1}$ is independently —H.

In one embodiment, each $R^{N2}$ is independently as defined above for $R^{N1}$.

In one embodiment, each $R^N$ is independently as defined above for $R^{N1}$.

Examples of Substituents

In one embodiment, the substituent(s), often referred to herein as R, are independently selected from: halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one embodiment, the substituent(s), often referred to herein as R, are independently selected from:
- —F, —Cl, —Br, and —I;
- —OH;
- —OMe, —OEt, —O(tBu), and —OCH₂Ph;
- —SH;
- —SMe, —SEt, —S(tBu), and —SCH₂Ph;
- —C(=O)H;
- —C(=O) Me, —C(=O) Et, —C(=O)(tBu), and —C(=O)Ph;
- —C(=O)OH;
- —C(=O)OMe, —C(=O)OEt, and —C(=O)O(tBu);
- —C(=O)NH₂, —C(=O)NHMe, —C(=O)NMe₂, and —C(=O)NHEt;
- —NHC(=O)Me, —NHC(=O)Et, —NHC(=O)Ph, succinimidyl, and maleimidyl;
- —NH₂, —NHMe, —NHEt, —NH(iPr), —NH(nPr), —NMe₂, —NEt₂, —N(iPr)₂, —N(nPr)₂, —N(nBu)₂, and —N(tBu)₂;
- —CN;
- —NO₂;
- -Me, -Et, -nPr, -iPr, -nBu, -tBu;
- —CF₃, —CHF₂, —CH₂F, —CCl₃, —CBr₃, —CH₂CH₂F, —CH₂CHF₂, and —CH₂CF₃;
- —OCF₃, —OCHF₂, —OCH₂F, —OCCl₃, —OCBr₃, —OCH₂CH₂F, —OCH₂CHF₂, and —OCH₂CF₃;
- —CH₂OH, —CH₂CH₂OH, and —CH(OH)CH₂OH;
- —CH₂NH₂, —CH₂CH₂NH₂, and —CH₂CH₂NMe₂; and, optionally substituted phenyl.

In one embodiment, the substituent(s), often referred to herein as R, are independently selected from: —F, —Cl, —Br, —I, —OH, —OMe, —OEt, —SH, —SMe, —SEt, —C(=O)Me, —C(=O)OH, —C(=O)OMe, —CONH₂, —CONHMe, —NH₂, —NMe₂, —NEt₂, —N(nPr)₂, —N(iPr)₂, —CN, —NO₂, -Me, -Et, —CF₃, —OCF₃, —CH₂OH, —CH₂CH₂OH, —CH₂NH₂, —CH₂CH₂NH₂, and -Ph.

In one embodiment, the substituent(s), often referred to herein as R, are independently selected from: hydroxy; ether (e.g., $C_{1-7}$alkoxy); ester; amido; amino; and, $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl).

In one embodiment, the substituent(s), often referred to herein as R, are independently selected from:
- —OH;
- —OMe, —OEt, —O(tBu), and —OCH₂Ph;
- —C(=O)OMe, —C(=O)OEt, and C(=O)O(tBu);
- —C(=O)NH₂, —C(=O)NHMe, —C(=O)NMe₂, and —C(=O)NHEt;
- —NH₂, —NHMe, —NHEt, —NH(iPr), —NH(nPr), —NMe₂, —NEt₂, —N(iPr)₂, —N(nPr)₂, —N(nBu)₂, and —N(tBu)₂;
- -Me, -Et, -nPr, -iPr, -nBu, -tBu;
- —CF₃, —CHF₂, —CH₂F, —CCl₃, —CBr₃, —CH₂CH₂F, —CH₂CHF₂, and —CH₂CF₃;
- —CH₂OH, —CH₂CH₂OH, and —CH(OH)CH₂OH; and,
- —CH₂NH₂, —CH₂CH₂NH₂, and —CH₂CH₂NMe₂.

Examples of Specific Embodiments

Some individual embodiments of the present invention include the following compounds:

| # HCl Salt Free Base | Structure |
|---|---|
| 1 SB-ACI-03 BSU-SB-36/102 | |
| 2 SB-ACI-04 BSU-SB-36/100 | |
| 3 SB-ACI-05 BSU-SB-36/104 | |

-continued
| # HCl Salt Free Base | Structure |
|---|---|
| 4 SB-ACI-06 BSU-SB-36/108 | 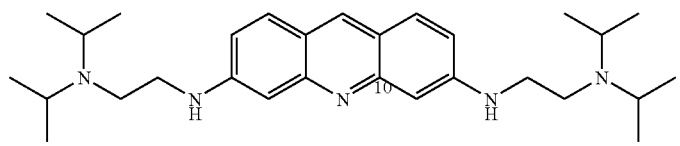 |
| 5 SB-ACI-10 BSU-SB-36/106 | 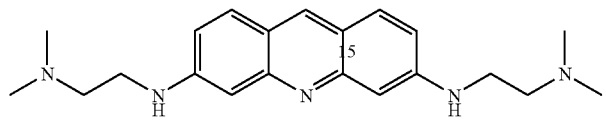 |
| 6 SB-ACI-23 BSU-SB-36/228 | 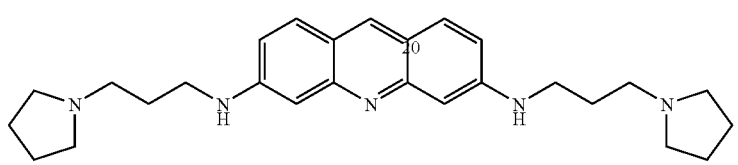 |
| 7 SB-ACI-24 BSU-SB-36/234 | 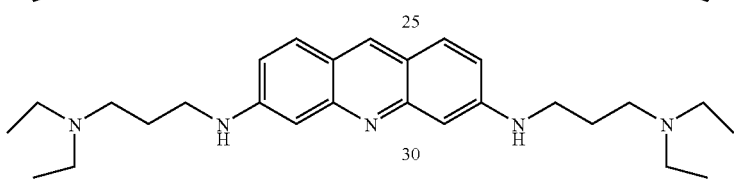 |
| 8 SB-ACI-25 BSU-SB-36/236 | 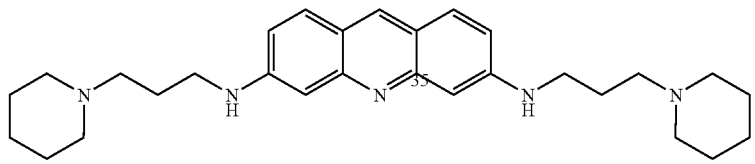 |
| 9 SB-ACI-27 BSU-SB-36a/030 | 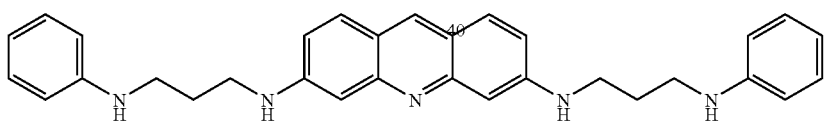 |
| 10 SB-ACI-26 BSU-SB-36a/028 | 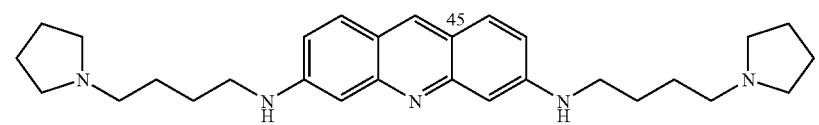 |
| 11 SB-ACI-28 BSU-SB-36a/038 | 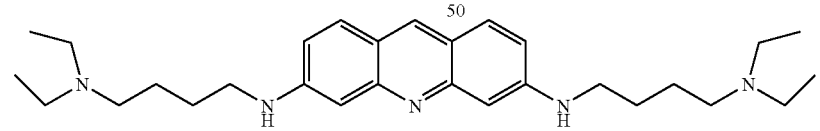 |
| 12 SB-ACI-08 BSU-SB-36/112 | 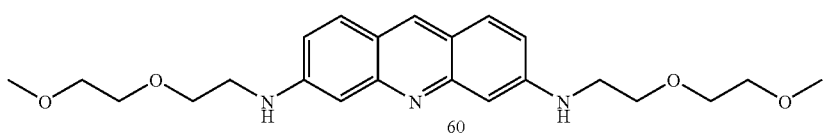 |
| 13 SB-ACI-09 BSU-SB-36/114 | 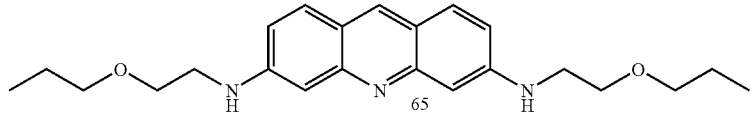 |

Chemical Terms

The term "carbo," "carbyl," "hydrocarbo," and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alkilidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

Examples of substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), norcarane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl, menthane, thujane, carane, pinane, bornane, norcarane, and camphene.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), aceanthrene ($C_{16}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=$CH_2$), 1-propenyl (—CH=CH—$CH_3$), 2-propenyl (allyl, —CH—CH—$CH_2$), isopropenyl (—C($CH_3$)=$CH_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —$CH_2$—C≡CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidene groups include $C_{1-4}$alkylidene, $C_{1-7}$alkylidene, $C_{1-20}$alkylidene.

Examples of alkylidene groups include, but are not limited to, methylidene (=$CH_2$), ethylidene (=CH—$CH_3$), vinylidene (=C=$CH_2$), and isopropylidene (=C($CH_3$)$_2$). An example of a substituted alkylidene is benzylidene (=CH-Ph).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne (≡CH) and ethylidyne (≡C—$CH_3$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl, and $C_{5-6}$heterocyclyl Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{3-12}$aryl, $C_{5-12}$aryl, $C_{5-7}$aryl, and $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl).

Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:
$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazble ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);
$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
$C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$oaryl, and acyl groups.

Heterocyclic groups (including heteroaryl groups) which have a nitrogen ring atom in the form of an —N═ group may be substituted in the form of an N-oxide, that is, as —N(→O)═ (also denoted —N$^+$ (→O$^-$)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms. Monocyclic examples of such groups include, but are not limited to, those derived from:
$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (═O) groups on ring carbon atoms include, but are not limited to, those derived from:
cyclic anhydrides (—C(═O)—O—C(═O)— in a ring), including but not limited to maleic anhydride ($C_5$), succinic anhydride ($C_5$), and glutaric anhydride ($C_6$);
cyclic carbonates (—O—C(═O)—O— in a ring), such as ethylene carbonate ($C_5$) and 1,2-propylene carbonate ($C_5$);
imides (—C(═O)—NR—C(═O)— in a ring), including but not limited to, succinimide ($C_5$), maleimide ($C_5$), phthalimide, and glutarimide ($C_6$);
lactones (cyclic esters, —O—C(═O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$); cyclic ureas (—NR—C(=O)—NR— in a ring), such as 2-imidazolidone ($C_5$) and pyrimidine-2,4-dione (e.g., thymine, uracil) ($C_6$).

The above groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

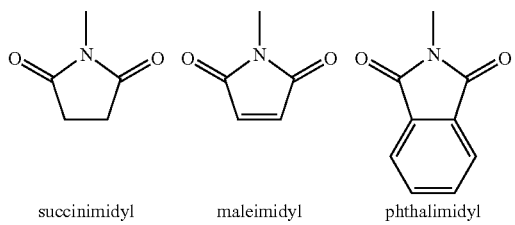

succinimidyl  maleimidyl  phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R1 is a ureido substituent, for example, hydrogen, a C$_{1-7}$alkyl group, a C$_{3-20}$heterocyclyl group, or a C$_{5-20}$aryl group, preferably hydrogen or a C$_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

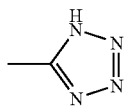

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a C$_{1-7}$alkyl group, a C$_{3-20}$heterocyclyl group, or a C$_{5-20}$aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$alkyl group, a C$_{3-20}$heterocyclyl group, or a C$_{5-20}$aryl group, preferably H or a C$_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$alkyl group, a C$_{3-20}$heterocyclyl group, or a C$_{5-20}$aryl group, preferably a C$_{1-7}$alkyl group (also referred to herein as C$_{1-7}$alkyl disulfide). Examples of C$_{1-7}$alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$alkyl group, a C$_{3-20}$heterocyclyl group, or a C$_{5-20}$aryl group, preferably a C$_{1-7}$alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group, including, for example, a fluorinated or perfluorinated C$_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$alkyl group, a C$_{3-20}$heterocyclyl group, or a C$_{5-20}$aryl group, preferably a C$_{1-7}$alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$alkyl group, a C$_{3-20}$heterocyclyl group, or a C$_{5-20}$aryl group, preferably a C$_{1-7}$alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

In many cases, substituents are themselves substituted. For example, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted-substituents are described below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$haloalkoxy: —OR, wherein R is a C$_{1-7}$haloalkyl group. Examples of C$_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of C$_{1-7}$carboxyalkyl groups include, but are not limited to, —CH$_2$COOH and —CH$_2$CH$_2$COOH.

C$_{1-7}$aminoalkyl: The term "C$_{1-7}$aminoalkyl group," as used herein, pertains to a C$_{1-7}$alkyl group in which at least one hydrogen atom has been replaced with an amino group. Examples of C$_{1-7}$aminoalkyl groups include, but are not limited to, —CH$_2$NH$_2$, —CH$_2$CH$_2$NH$_2$, and —CH$_2$CH$_2$N(CH$_3$)$_2$.

C$_{5-20}$aryl-C$_{1-7}$alkyl: The term "C$_{5-20}$aryl-C$_{1-7}$alkyl," as used herein, describers certain C$_{1-7}$alkyl groups which have been substituted with a C$_{5-20}$aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—), cinnamyl (Ph-CH=CH—CH$_2$—).

C$_{5-20}$aryl-C$_{1-7}$alkoxy: The term "C$_{5-20}$aryl-C$_{1-7}$alkoxy," as used herein, describes certain C$_{1-7}$alkoxy groups which have been substituted with a C$_{5-20}$aryl group. Examples of such groups include, but are not limited to, benzyloxy, benzhydryloxy, trityloxy, phenethoxy, styryloxy, and cimmamyloxy.

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (from toluene), xylyl (from xylene), mesityl (from mesitylene), and cumenyl (or cumyl, from cumene), and duryl (from durene).

C$_{1-7}$alkyl-C$_{5-20}$aryloxy: The term "C$_{1-7}$alkyl-C$_{5-20}$aryloxy," as used herein, describes certain C$_{5-20}$aryloxy groups which have been substituted with a C$_{1-7}$alkyl group. Examples of such groups include, but are not limited to, tolyloxy, xylyloxy, mesityloxy, cumenyloxy, and duryloxy.

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r- forms; endo- and exo-forms; R—, S—, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amidelimino alcohol, amidine/amidine, nitroso/oxime, thioketone/enethiol, N-nitroso/hyroxyazo, and nitrolaci-nitro.

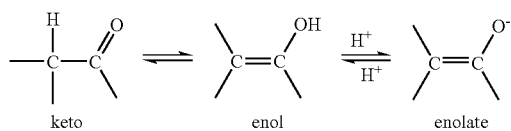

keto       enol       enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective*

*Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH—Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amride (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O$).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
C$_{1-7}$alkyl
(e.g., -Me, -Et, -nPr, -iPr, -nBu, -sBu, -iBu, -tBu);
C$_{1-7}$aminoalkyl
(e.g., aminoethyl; 2-(N,N-diethylamino)ethyl; 2-(4-morpholino)ethyl); and
acyloxy-C$_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Synthesis

Several methods for the chemical synthesis of compounds of the present invention are described herein (see, e.g., the Figures discussed below). These and/or other well known methods may be modified and/or adapted in known ways in order to facilitate the synthesis of additional compounds within the scope of the present invention.

FIG. 1 is a scheme illustrating a chemical synthesis method for 3,6-diamino-acridone. The reagents/conditions for the steps in this figure are: (i) KNO$_3$/H$_2$SO$_4$; (ii) CrO$_3$, AcOH, reflux; (iii) SnCl$_2$/HCl, 90–100° C.

Figure 2:
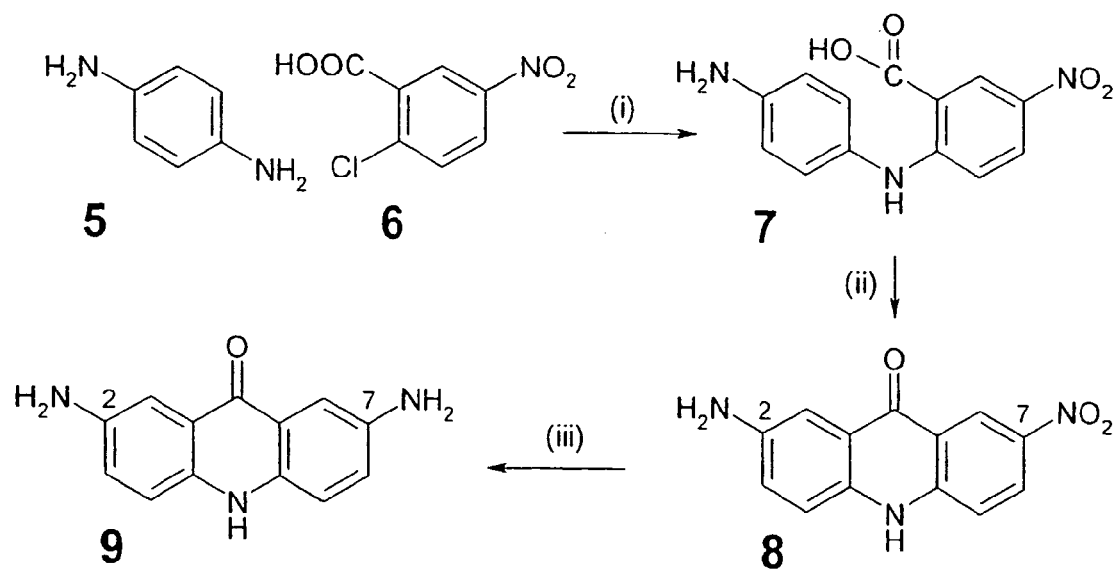
FIG. 2 is a scheme illustrating a chemical synthesis method for 2,7-diamino-acridone.

FIG. 2 is a scheme illustrating a chemical synthesis method for 2,7-diamino-acridone. The reagents/conditions for the steps in this figure are: (i) Cu/CuSO$_4$/K$_2$CO$_3$/H$_2$O, 5 hrs reflux; (ii) polyphosphoric acid (PPA), 100° C., 5 hr; (iii) Na$_2$S, NaOH, EtOH, H$_2$O, reflux.

Figure 3:
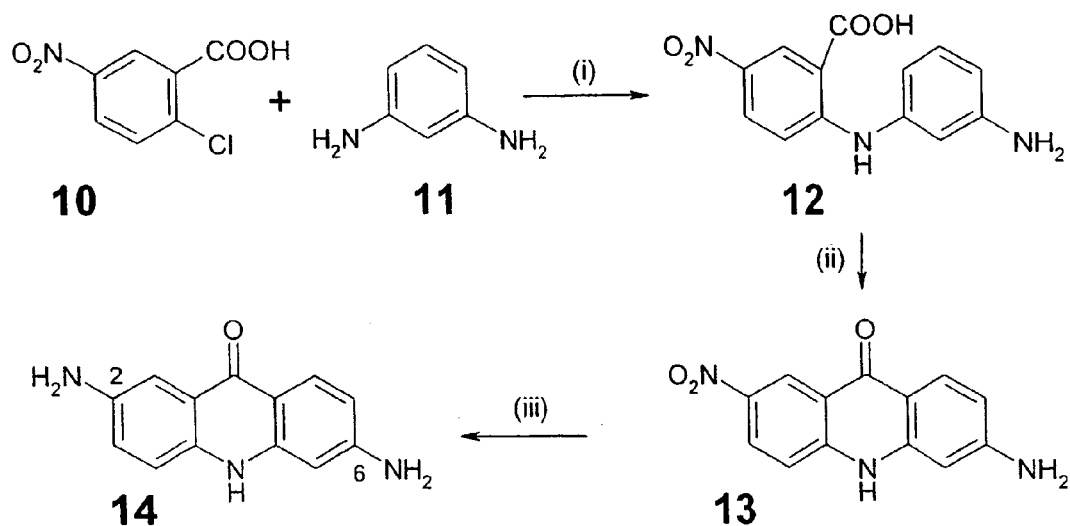
FIG. 3 is a scheme illustrating a chemical synthesis method for 2,6-diamino-acridone.

FIG. 3 is a scheme illustrating a chemical synthesis method for 2,6-diamino-acridone. The reagents/conditions for the steps in this figure are: (i) Cu, CuSO$_4$, K$_2$CO$_3$, H$_2$O; (ii) H$_2$SO$_4$, H$_2$O; (iii) Na$_2$S, NaOH.

Figure 4:
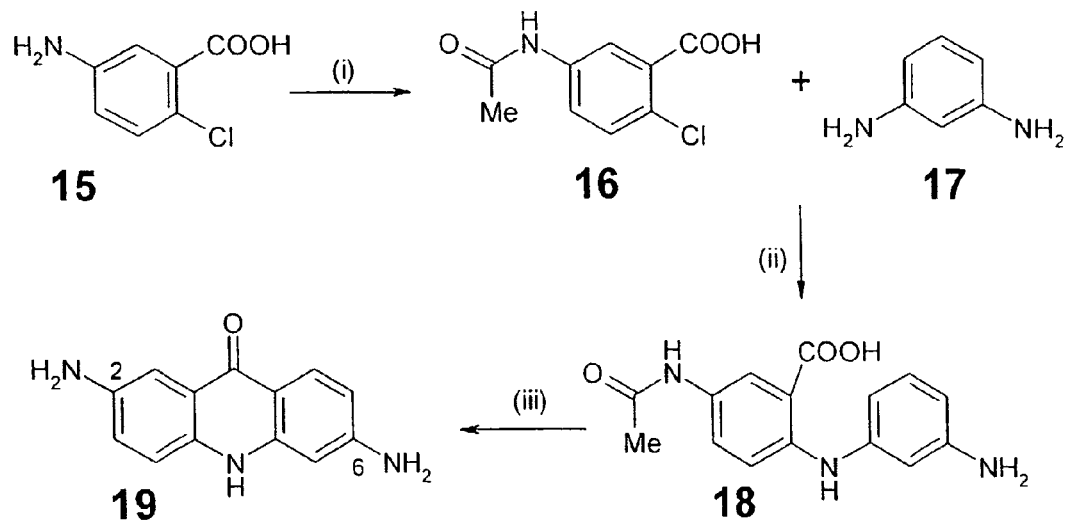
FIG. 4 is a scheme illustrating another chemical synthesis method for 2,6-diamino-acridone.

FIG. 4 is a scheme illustrating another chemical synthesis method for 2,6-diamino-acridone. The reagents/conditions for the steps in this figure are: (i) acetic anhydride, $H_2O$, $Na_2CO_3$; (ii) pentan-1-ol, $KCO_3$, Cu; (iii) $H_2SO_4$, $H_2O$.

Figure 5:
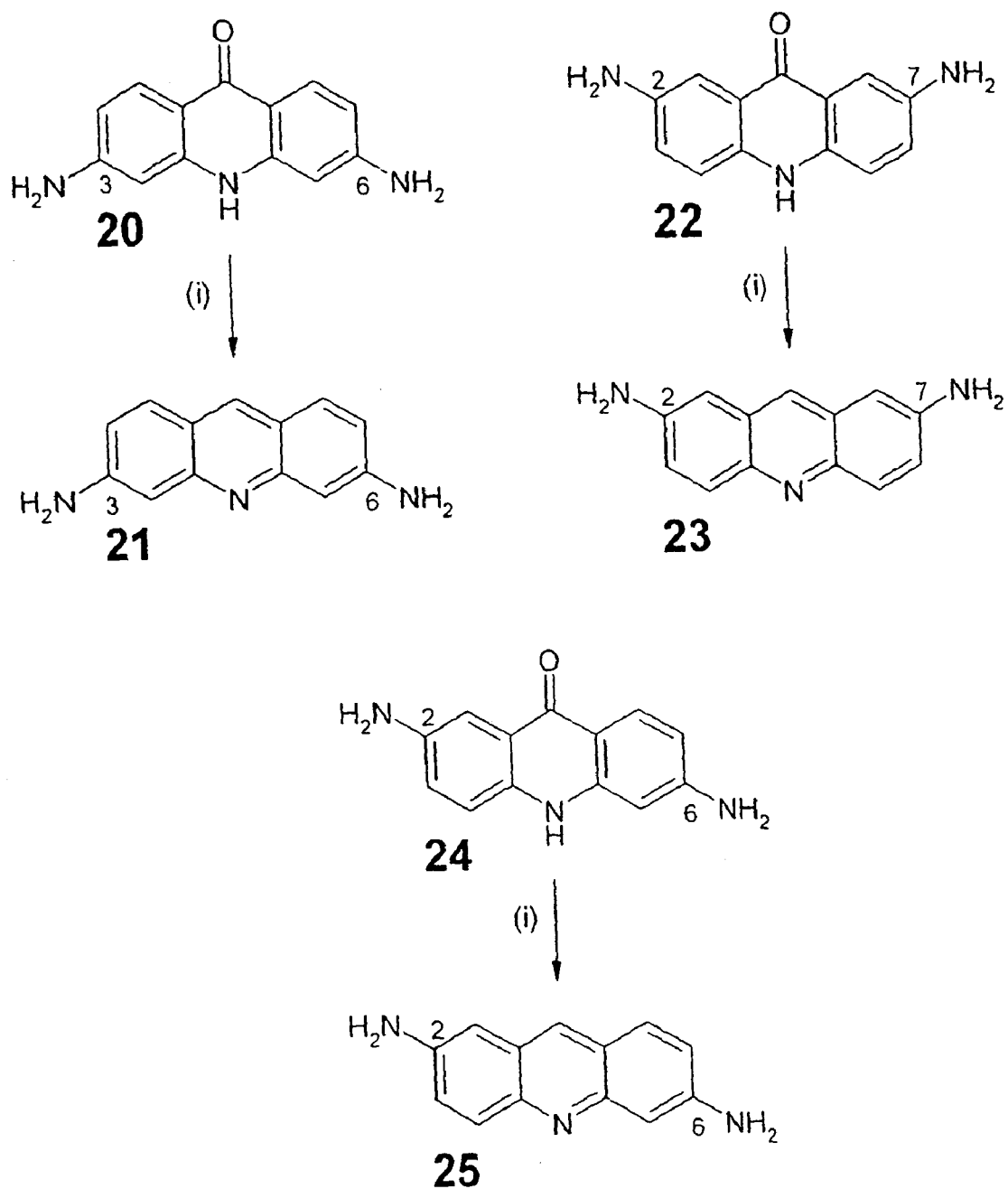
FIG. 5 is a scheme illustrating a chemical synthesis method for 2,6-diamino-acridine, 2,7-diamino-acridine, and 2,6-diamino-acridine.

FIG. 5 is a scheme illustrating a chemical synthesis method for 2,6-diamino-acridine, 2,7-diamino-acridine, and 2,6-diamino-acridine. The reagents/conditions for the steps in this figure are: (i) Na/Hg, 2% aq NaOH.

Figure 6:
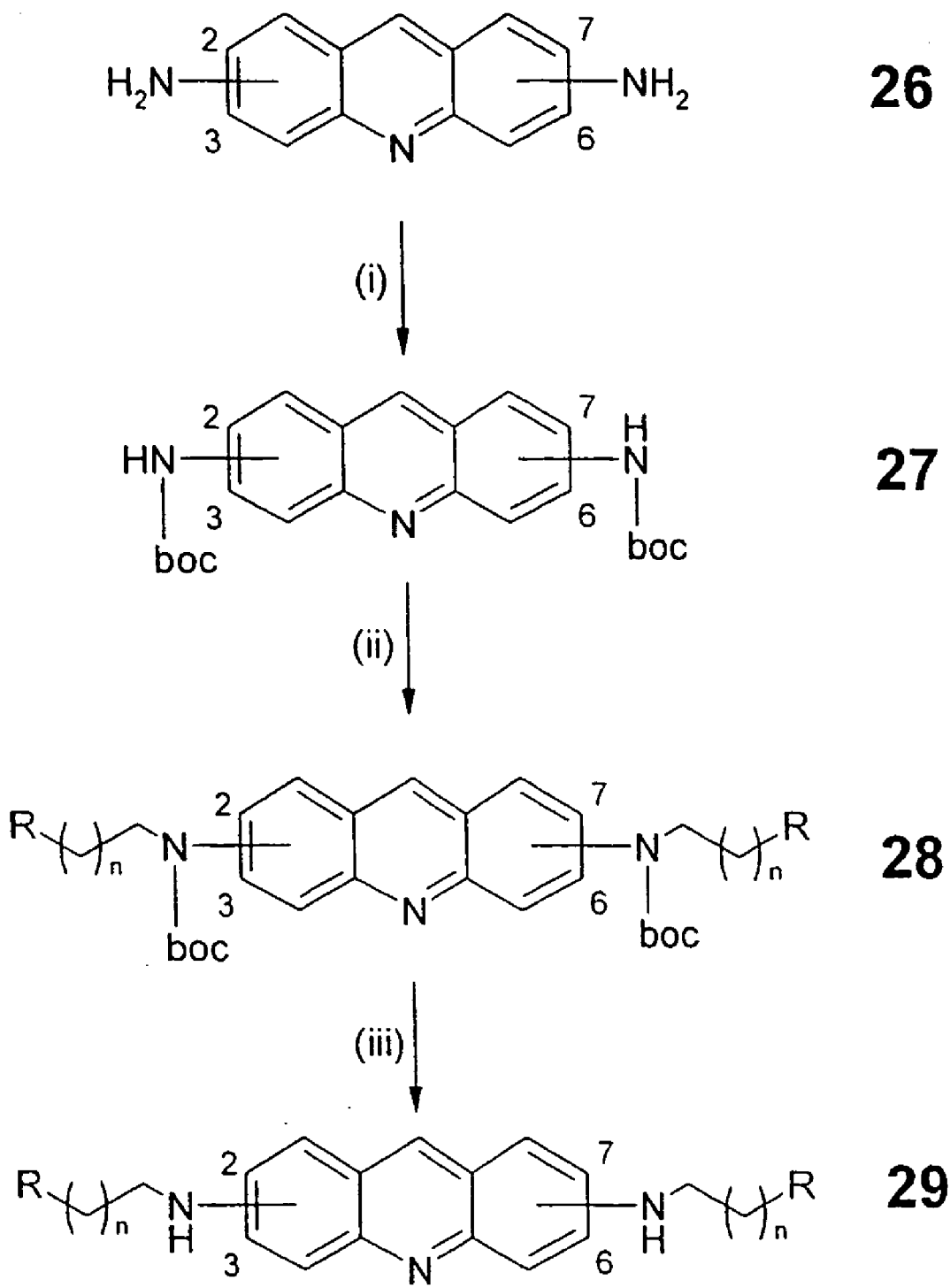
FIG. 6 is a scheme illustrating a chemical synthesis method for certain disubstituted acridines of the present invention.

FIG. 6 is a scheme illustrating a chemical synthesis method for certain disubstituted acridines of the present invention. The reagents/conditions for the steps in this figure are: (i) acetone, $(Boc)_2O$, $Et_3N$; (ii) NaH, DMF, $ClCH_2(CH_2)_nR$; (iii) 10% HCl, EtOAc. By using appropriate halides (e.g., $ClCH_2(CH_2)_nR$), different acridines of the present invention are obtained.

Figure 7:
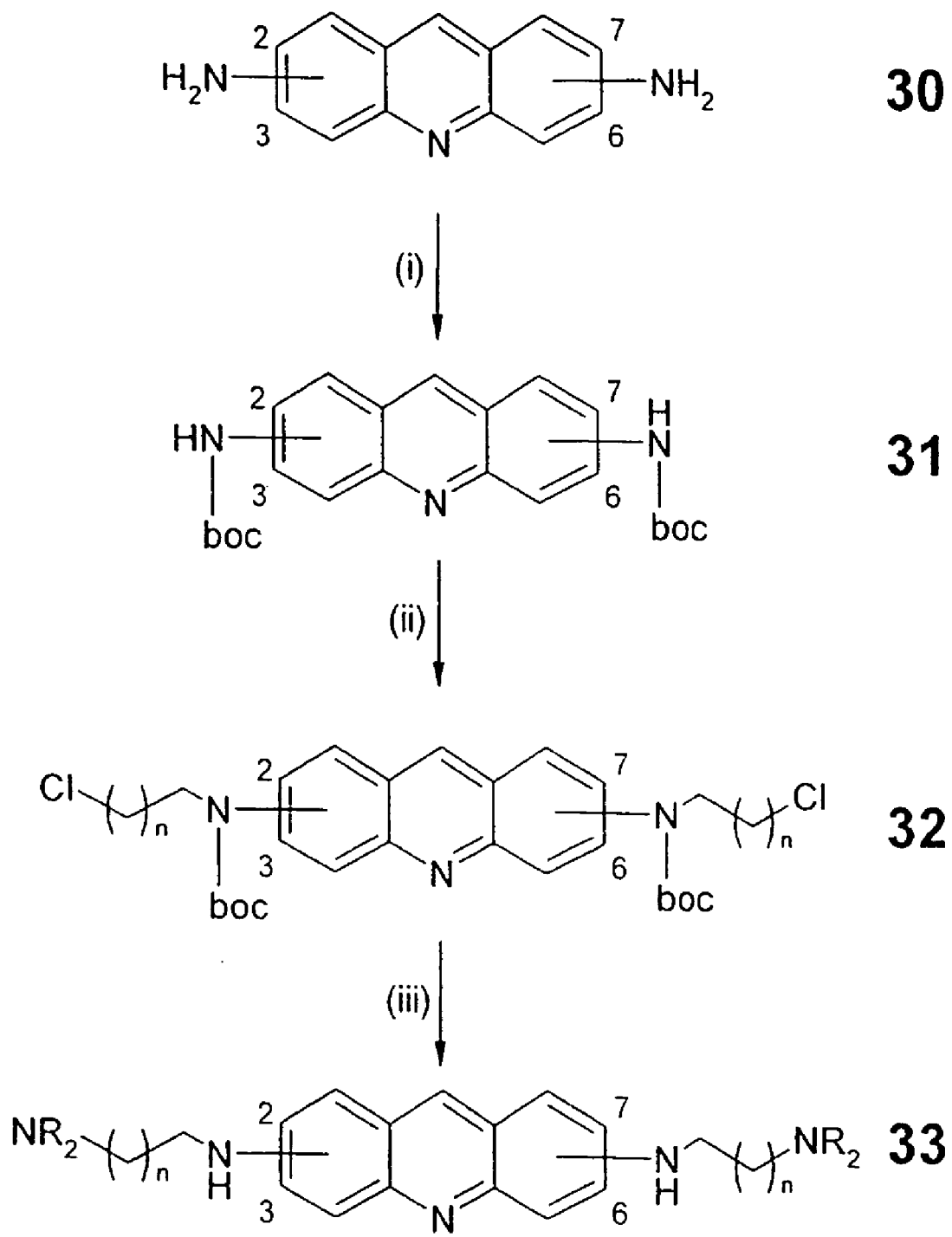
FIG. 7 is a scheme illustrating a chemical synthesis method for certain disubstituted acridines of the present invention.

FIG. 7 is a scheme illustrating a chemical synthesis method for certain disubstituted acridines of the present invention. The reagents/conditions for the steps in this figure are: (i) acetone, $(Boc)_2O$, $Et_3N$; (ii) NaH, DMF, $ClCH_2(CH_2)_nBr$; (iii) EtOH, KI, $NHR_2$. By using appropriate dihalides (e.g., $ClCH_2(CH_2)_nBr$), and appropriate amines (e.g., $NHR_2$), different acridines of the present invention are obtained.

Figure 8:
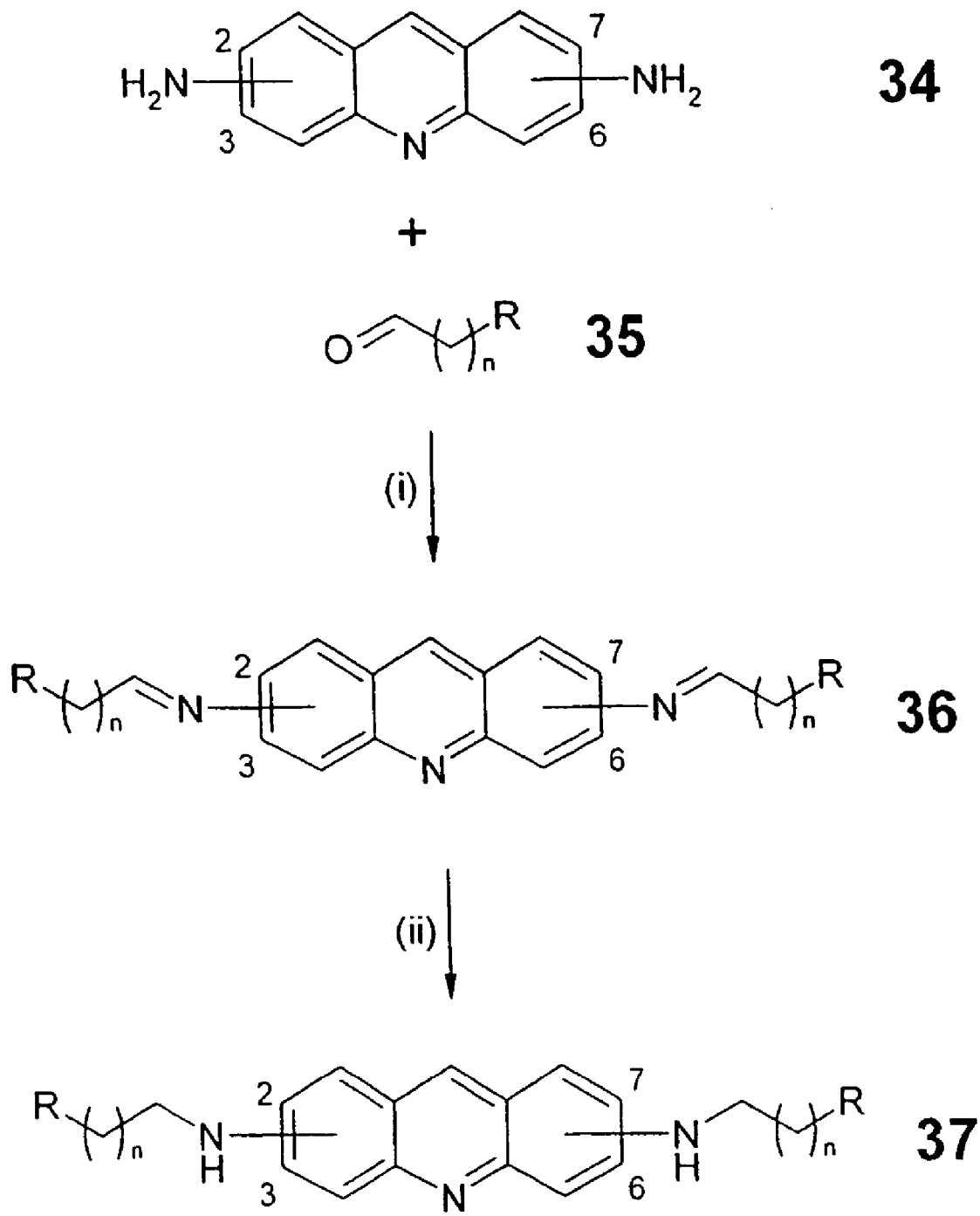
FIG. 8 is a scheme illustrating a chemical synthesis method for certain disubstituted acridines of the present invention.

FIG. 8 is a scheme illustrating a chemical synthesis method for certain disubstituted acridines of the present invention. The reagents/conditions for the steps in this figure are: (i) DMF or THF; (ii) reducing agent: $NaBH_4$ or NaCNBH or $NaB(OAc)_3H$. By using appropriate aldehydes (e.g., $R(CH_2)_nCHO$), different acridines of the present invention are obtained.

Figure 9:
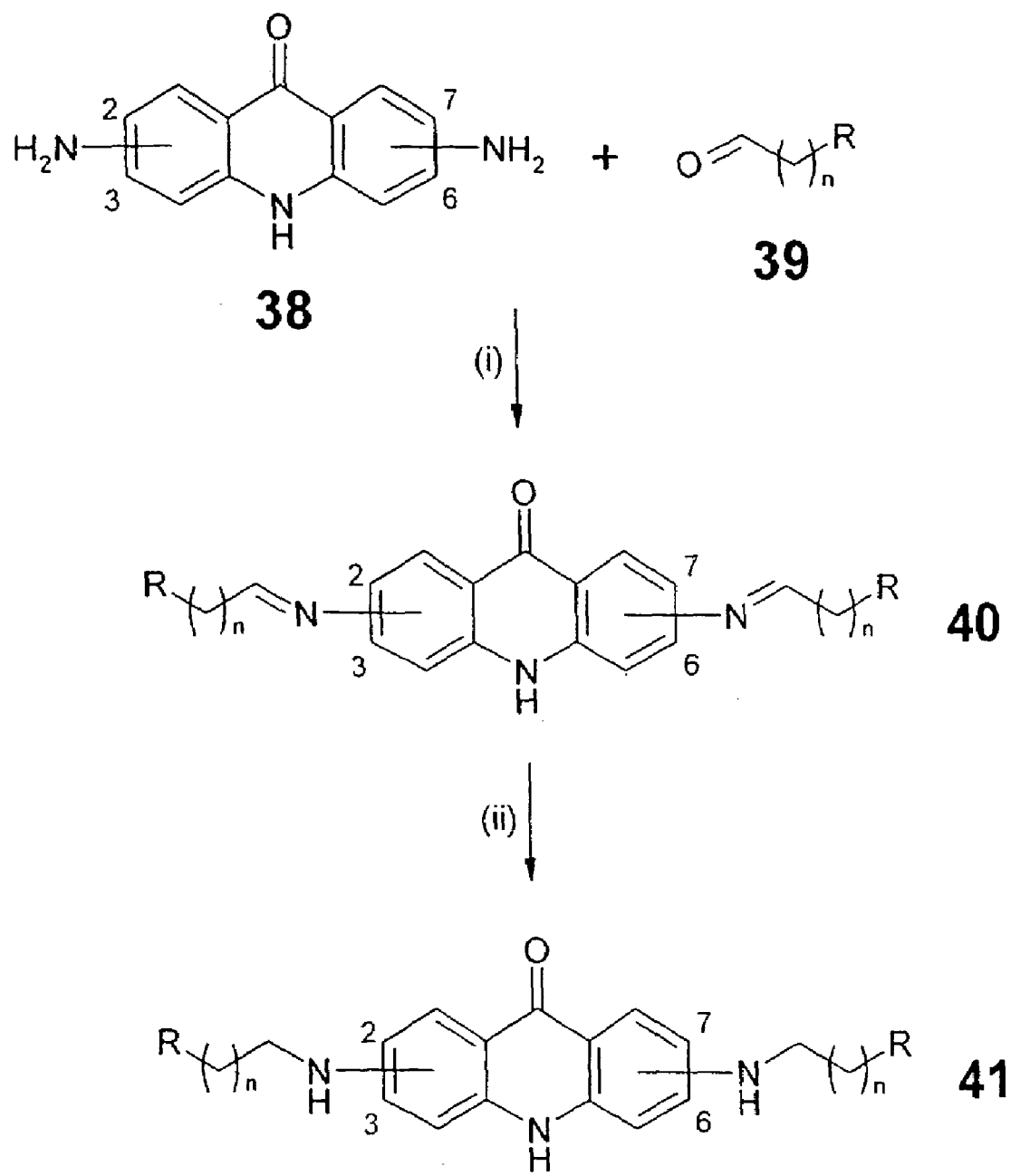
FIG. 9 is a scheme illustrating a chemical synthesis method for certain disubstituted acridines of the present invention.

FIG. 9 is a scheme illustrating a chemical synthesis method for certain disubstituted acridines of the present invention. The reagents/conditions for the steps in this figure are: (i) DMF or THF; (ii) reducing agent: $NaBH_4$ or NaCNBH or $NaB(OAc)_3H$. By using appropriate aldehydes (e.g., $R(CH_2)_nCHO$), different acridines of the present invention are obtained.

Figure 10:
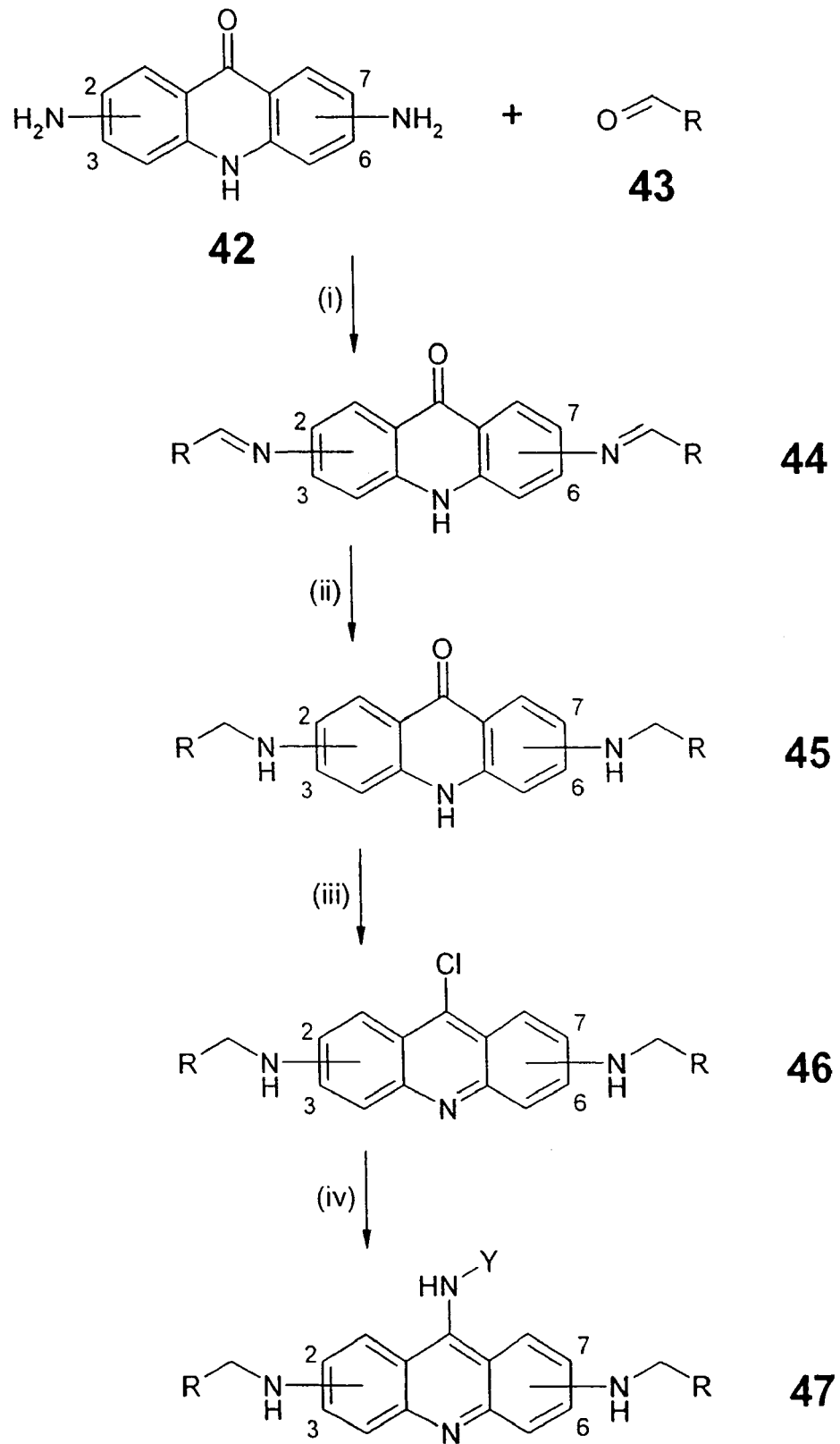
FIG. 10 is a scheme illustrating a chemical synthesis method for certain disubstituted acridines and certain trisubstituted acridines of the present invention.

FIG. 10 is a scheme illustrating a chemical synthesis method for certain disubstituted acridines and certain trisubstituted acridines of the present invention. The reagents/conditions for the steps in this figure are: (i) DMF or THF; (ii) reducing agent: $NaBH_4$ or NaCNBH or $NaB(OAc)_3H$; (iii) $POCl_3$, reflux; (iv) $NH_2Y$, $CHCl_3$, reflux. By using appropriate aldehydes (e.g., RCHO), and appropriate amines (e.g., $NH_2Y$), different acridines of the present invention are obtained.

Figure 11:
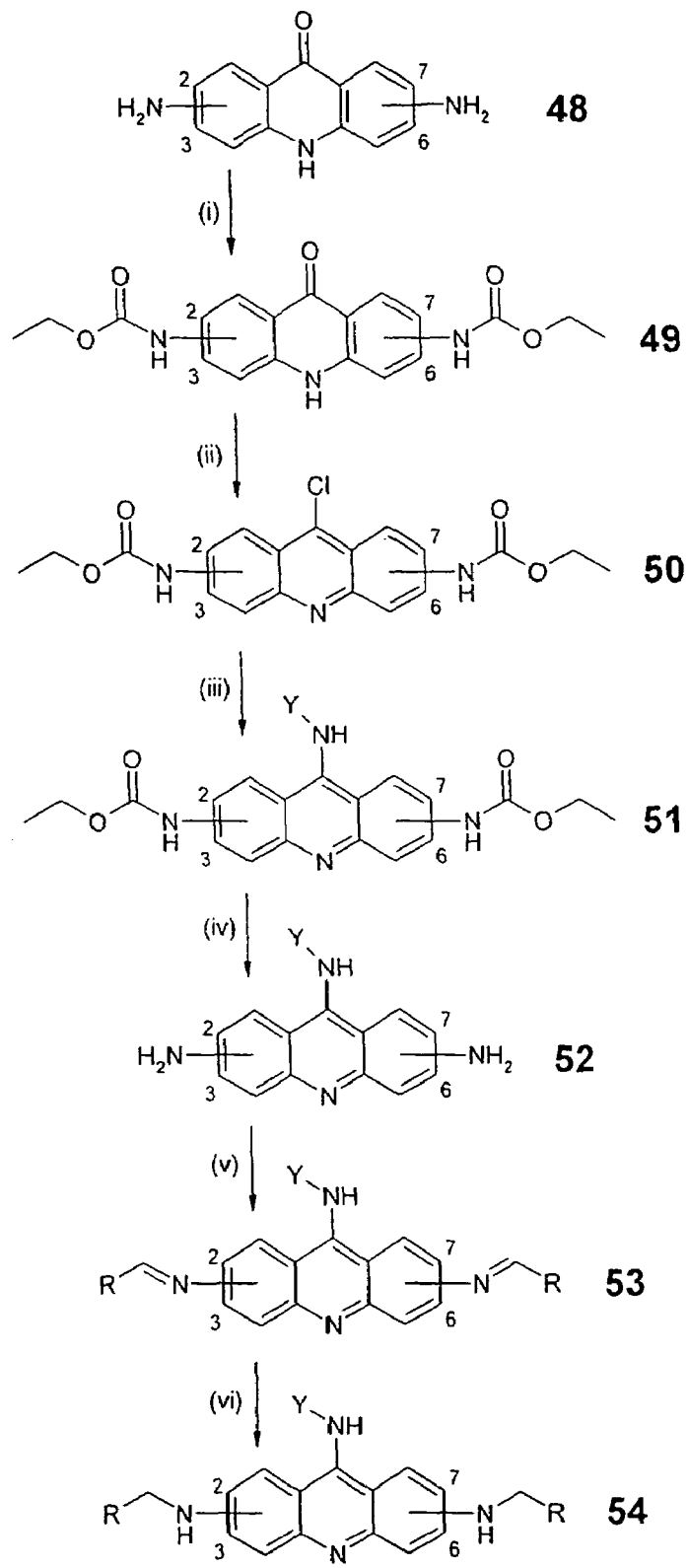
FIG. 11 is a scheme illustrating a chemical synthesis method for certain trisubstituted acridines of the present invention.

FIG. 11 is a scheme illustrating a chemical synthesis method for certain trisubstituted acridines of the present invention. The reagents/conditions for the steps in this figure are: (i) EtOCOCl; (ii) $POCl_3$, reflux; (iii) $NH_2Y$, $CHCl_3$, reflux; (iv) deprotection; (v) DMF or THF, RCHO; (vi) reducing agent: $NaBH_4$ or $NaCNBH_3$ or $NaB(OAc)_3H$. By using appropriate amines (e.g., $NH_2Y$), and appropriate aldehydes (e.g., RCHO), different acridines of the present invention are obtained.

Figure 12:
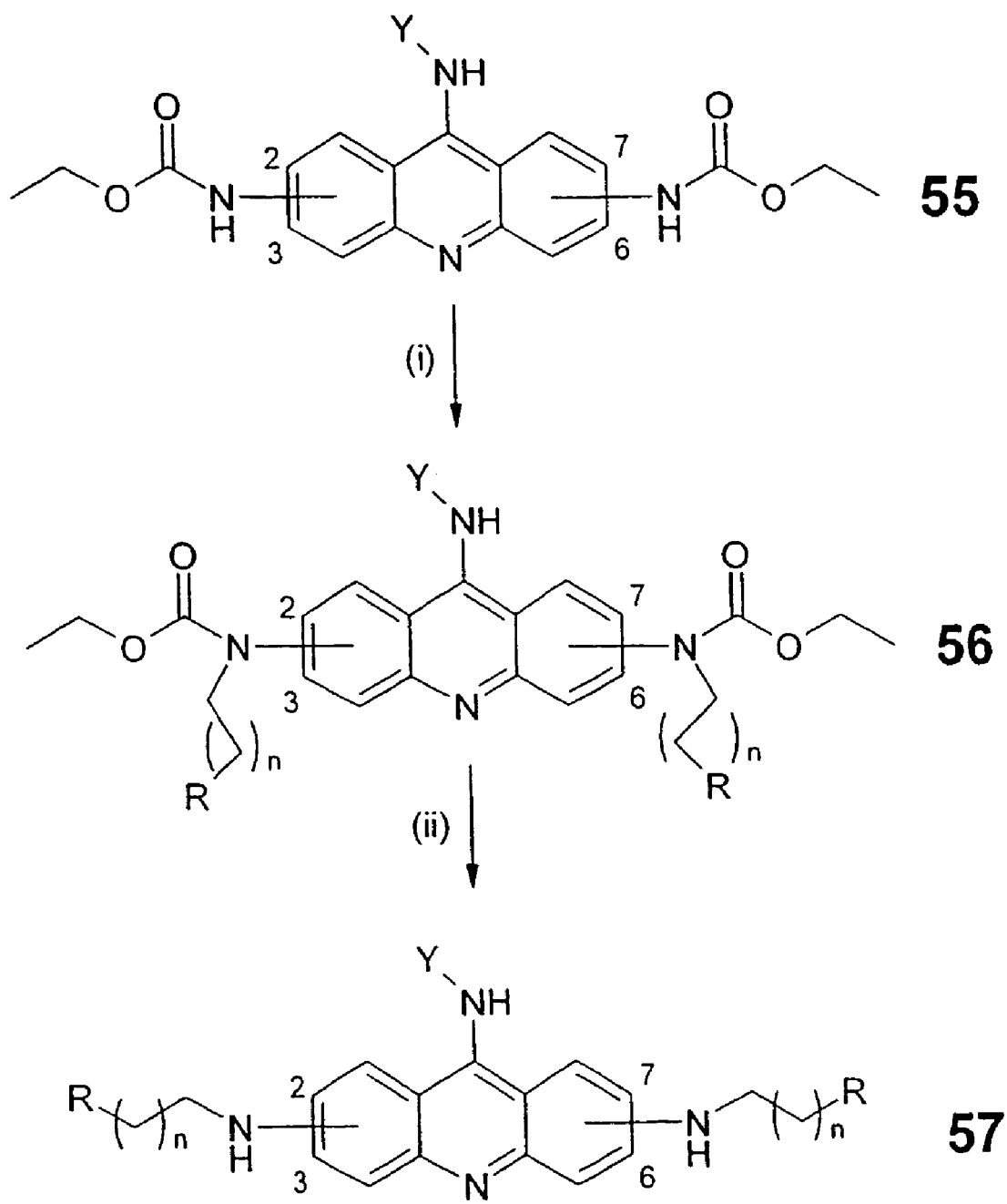
FIG. 12 is a scheme illustrating a chemical synthesis method for certain trisubstituted acridines of the present invention.

FIG. 12 is a scheme illustrating a chemical synthesis method for certain trisubstituted acridines of the present invention. The reagents/conditions for the steps in this figure are: (i) NaH, $RCH_2(CH_2)_nCl$; (ii) deprotection. By using appropriate amines (e.g., $NH_2Y$), and appropriate halides (e.g., $RCH_2(CH_2)_nCl$), different acridines of the present invention are obtained.

Figure 13:
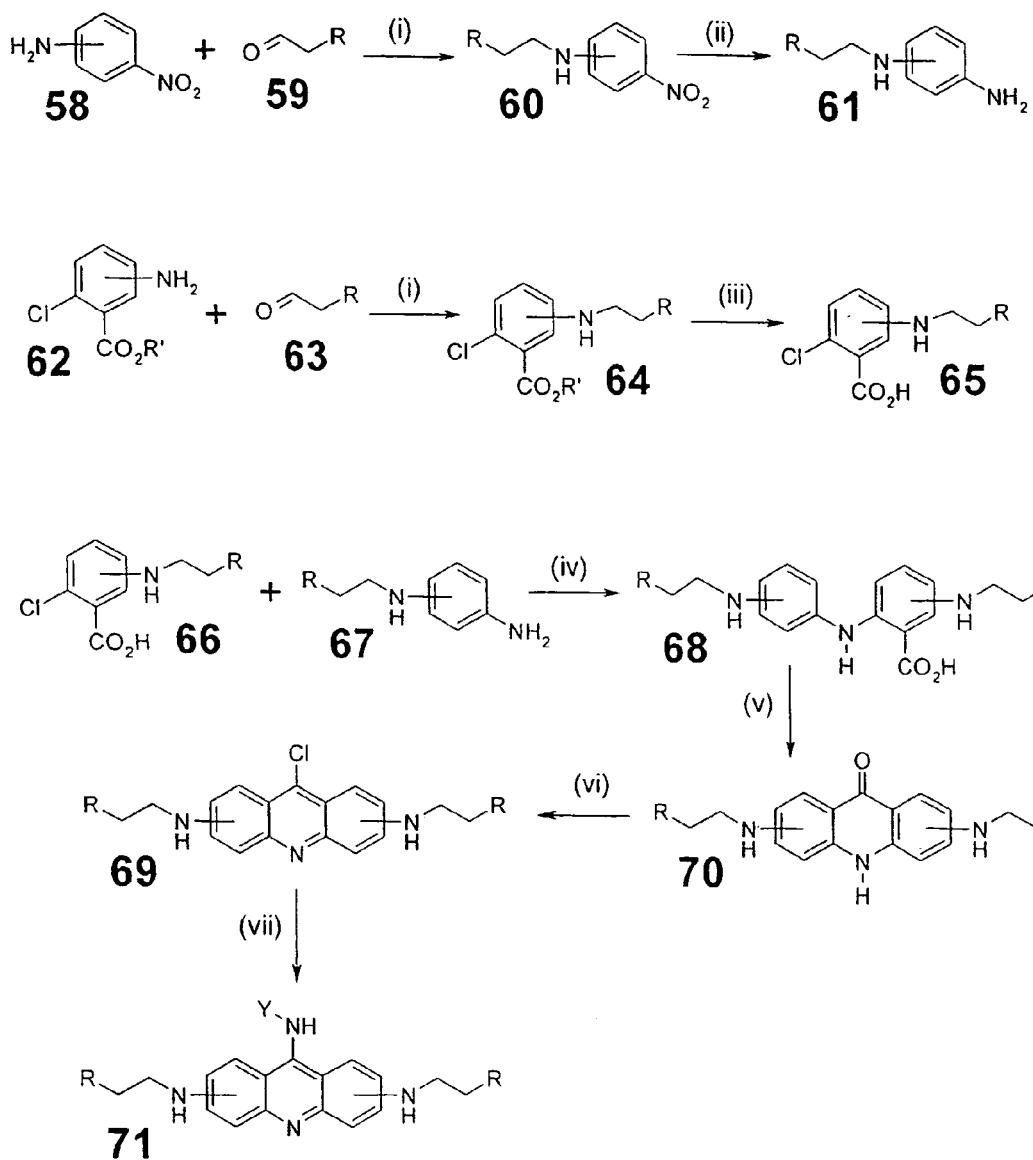
FIG. 13 is a scheme illustrating a chemical synthesis method for certain trisubstituted acridines of the present invention.

FIG. 13 is a scheme illustrating a chemical synthesis method for certain trisubstituted acridines of the present invention. The reagents/conditions for the steps in this figure are: (i) THF/DMF, $NaCNBH_3$; (ii) $H_2$ Pd/C; (iii) $H^+$ (deprotection), (iv) Cu, $CuSO_4$, $K_2CO_3$; (V) polyphosphoric acid (PPA); (vi) $POCl_3$, $NH_2Y$, $CHCl_3$. By using appropriate aldehydes (e.g., $RCH_2CHO$), and appropriate amines (e.g., $NH_2Y$), different acridines of the present invention are obtained.

Figure 14:
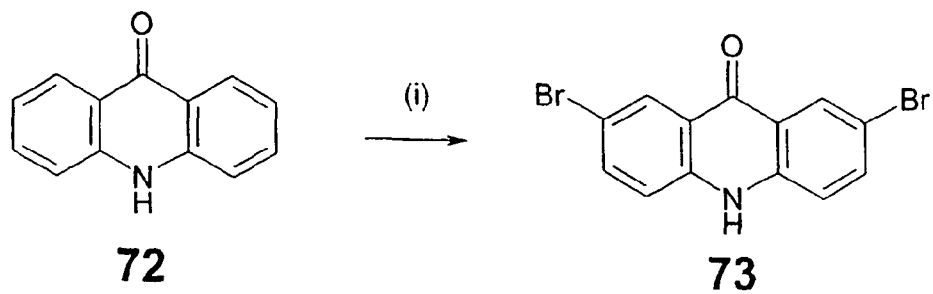
FIG. 14 is a scheme illustrating a chemical synthesis method for 2,7-dibromoacridone.

FIG. 14 is a scheme illustrating a chemical synthesis method for 2,7-dibromoacridone. The reagents/conditions for the steps in this figure are: (i) $CH_3COOH$, $Br_2$, reflux.

Figure 15:
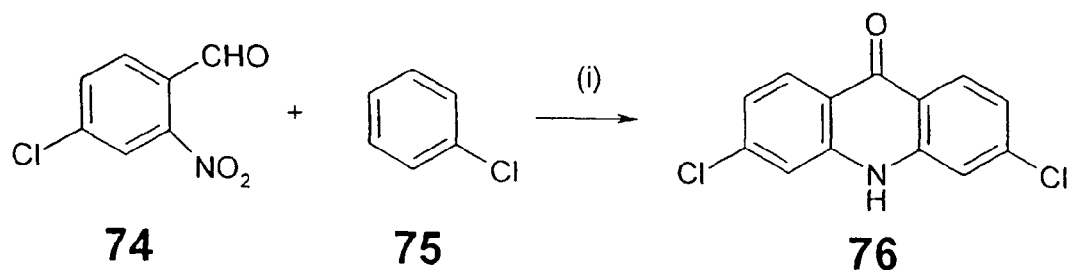
FIG. 15 is a scheme illustrating a chemical synthesis method for 3,6-dichloroacridone.

FIG. 15 is a scheme illustrating a chemical synthesis method for 3,6-dichloroacridone. The reagents/conditions for the steps in this figure are: (i) $H_2SO_4$, $NaNO_2$.

Figure 16:
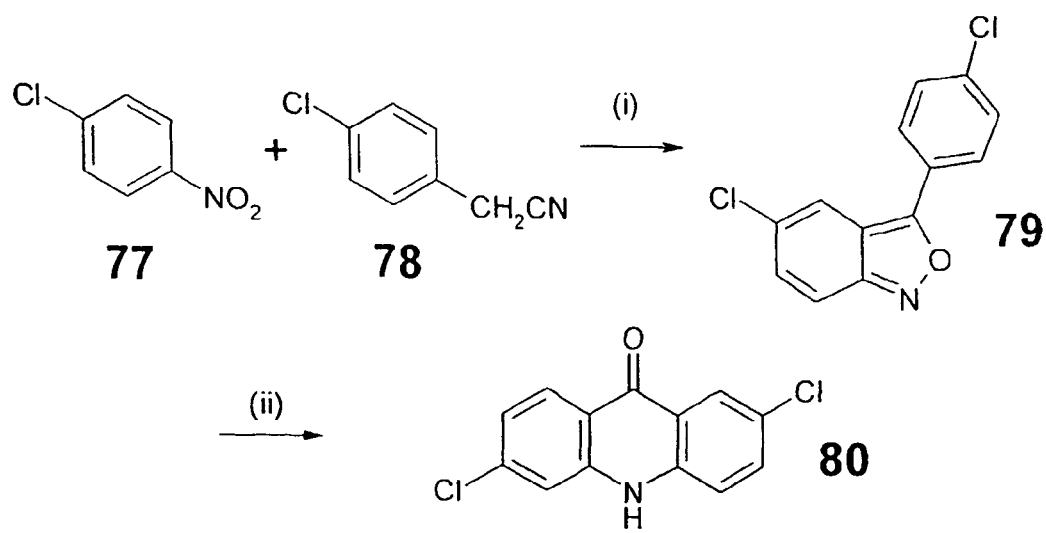
FIG. 16 is a scheme illustrating a chemical synthesis method for 2,6-dichloroacridone.

FIG. 16 is a scheme illustrating a chemical synthesis method for 2,6-dichloroacridone. The reagents/conditions for the steps in this figure are: (i) KOH, $CHCl_3$; (ii) $H_2SO_4$, $NaNO_2$.

Figure 17:
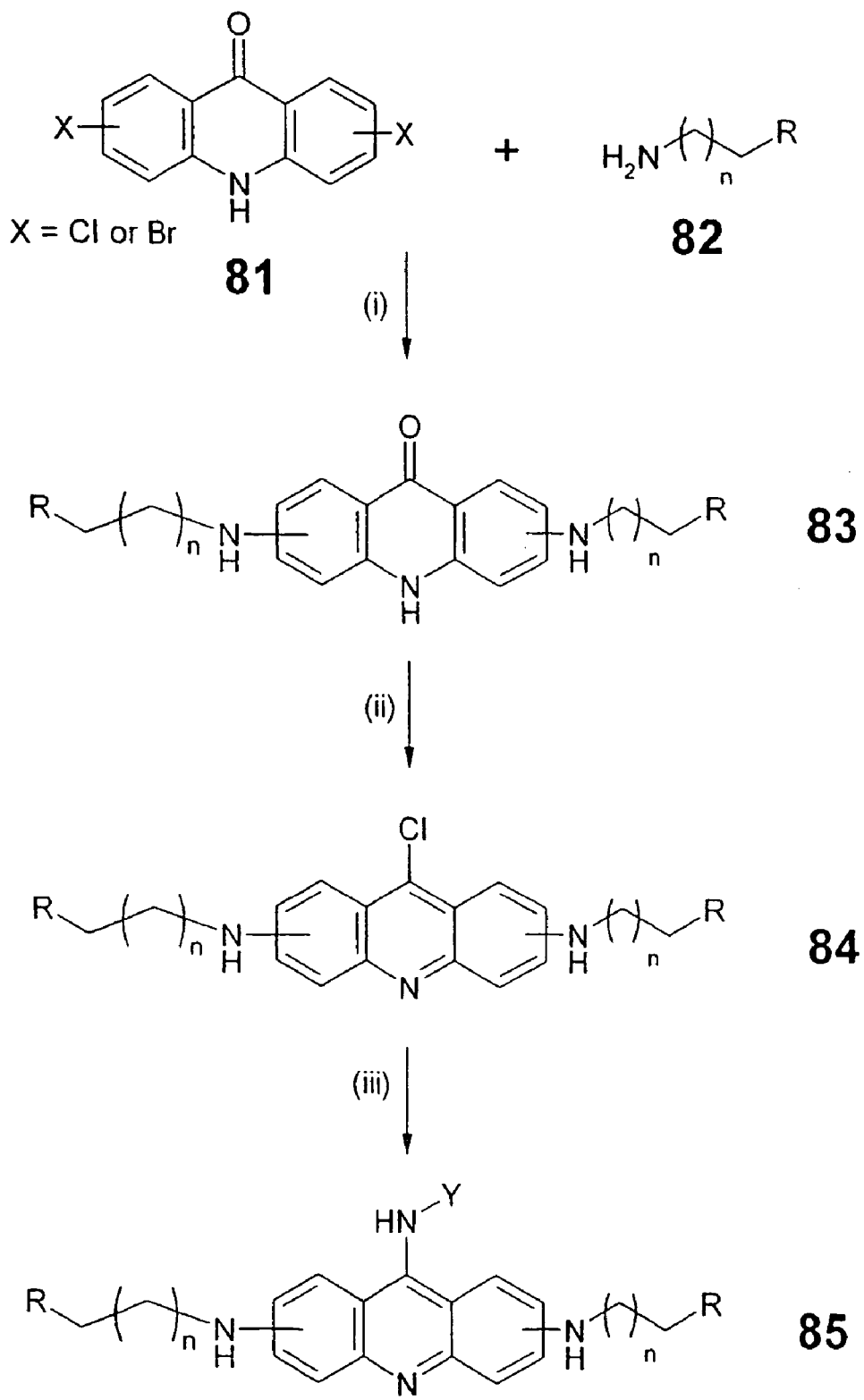
FIG. 17 is a scheme illustrating a chemical synthesis method for certain trisubstituted acridines of the present invention.

FIG. 17 is a scheme illustrating a chemical synthesis method for certain trisubstituted acridine. The reagents/conditions for the steps in this figure are: (i) Pd; (ii) $POCl_3$; (iii) $NH_2Y$, $CHCl_3$. By using appropriate amines (e.g., $RCH_2(CH_2)_nNH_2$), and appropriate amines (e.g., $NH_2Y$), different acridines of the present invention are obtained.

Additional relevant synthesis methods are described in, for example, Matsumura, 1929, Korolev et al., 1977, and I.G. Farbenindustrie Akt.-Ges in Frankfurt a.M., 1930, and the references cited therein.

Uses

The present invention provides active compounds, specifically, active acridines and acridines, as described herein.

The term "active," as used herein, specifically includes both compounds with intrinsic activity (drugs) as well as prodrugs of such compounds, which prodrugs may themselves exhibit little or no intrinsic activity.

The present invention also provides active compounds which inhibit telomerase.

The present invention also provides methods of inhibiting telomerase, in vitro or in vivo, comprising contacting a cell with an effective amount of an active compound, as described herein. In one embodiment, the method is performed in vitro. In one embodiment, the method is performed in vivo.

The term "inhibiting telomerase," as used herein, includes: inhibiting telomerase activity; inhibiting the formation of telomerase complexes; and inhibiting the activity of telomerase complexes.

One of ordinary skill in the art is readily able to determine whether or not a candidate compound inhibits telomerase activity. For example, one assay which may conveniently be used in order to assess the telomerase inhibition offered by a particular compound is described in the examples below.

The present invention also provides methods of inhibiting telomerase in a cell, comprising contacting said cell with an effective amount of an active compound, preferably in the form of a pharmaceutically acceptable composition. Such a method may be practised in vitro or in vivo.

The present invention also provides active compounds which (a) regulate (e.g., inhibit) cell proliferation; (b) inhibit cell cycle progression; (c) promote apoptosis; or (d) a combination of one or more of these.

Thus, the present invention also provides methods of (a) regulating (e.g., inhibiting) cell proliferation; (b) inhibiting cell cycle progression; (c) promoting apoptosis; or (d) a combination of one or more of these, in vitro or in vivo, comprising contacting a cell with an effective amount of an active compound, as described herein.

One of ordinary skill in the art is readily able to determine whether or not a candidate compound regulate (e.g., inhibit) cell proliferation, etc. For example, assays which may conveniently be used to assess the activity offered by a particular compound are described in the examples below.

For example, a sample of cells (e.g., from a tumour) may be grown in vitro and an active compound brought into contact with said cells, and the effect of the compound on those cells observed. As an example of "effect," the morphological status of the cells (e.g., alive or dead, etc.) may be determined. Where the active compound is found to exert an influence on the cells, this may be used as a prognostic or diagnostic marker of the efficacy of the compound in methods of treating a patient carrying cells of the same cellular type.

Methods of Treatment, Etc.

The invention further provides methods of treatment, comprising administering to a subject in need of treatment a therapeutically-effective amount of an active compound, preferably in the form of a pharmaceutical composition.

The invention further provides active compounds for use in a method of treatment of the human or animal body by therapy, example, in the treatment of a condition mediated by telomerase, cancer, a proliferative condition, or other condition as described herein.

The invention further provides the use of an active compound for the manufacture of a medicament, for example, for the treatment of a condition mediated by telomerase, cancer, a proliferative condition, or other condition as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Active compounds may also be used, as described above, in combination therapies, that is, in conjunction with other agents, for example, cytotoxic agents.

Anti-Telomerase Applications

The present invention also provides active compounds which are anti-telomerase agents, and which treat a condition mediated by telomerase.

The term "a condition mediated by telomerase," as used herein pertains to a condition in which telomerase and/or the action of telomerase is important or necessary, e.g., for the onset, progress, expression, etc. of that condition.

One of ordinary skill in the art is readily able to determine whether or not a candidate compound treats a condition mediated by telomerase for any particular cell type. For example, assays which may conveniently be used to assess the activity offered by a particular compound are described in the examples below.

Anticancer Applications

The present invention also provides active compounds which are anticancer agents, and treat cancer.

Thus, the present invention also provides methods of treating cancer, comprising administering to a subject in need of treatment a therapeutically-effective amount of an active compound, as described herein, preferably in the form of a pharmaceutical composition.

One of ordinary skill in the art is readily able to determine whether or not a candidate compound treats a cancerous condition for any particular cell type. For example, assays which may conveniently be used to assess the activity offered by a particular compound are described in the examples below.

The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). Examples of cancers are discussed below.

Antiproliferative Applications

The present invention also provides active compounds which are antiproliferative agents. The term "antiproliferative agent" as used herein, pertain to a compound which treats a proliferative condition (i.e., a compound which is useful in the treatment of a proliferative condition).

Thus, the present invention also provides methods of treating a proliferative condition, comprising administering to a subject in need of treatment a therapeutically-effective amount of an active compound, as described herein, preferably in the form of a pharmaceutical composition.

One of ordinary skill in the art is readily able to determine whether or not a candidate compound treats a proliferative condition for any particular cell type. For example, assays which may conveniently be used to assess the activity offered by a particular compound are described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

Additional Uses

Active compounds may also be used as cell culture additives to inhibit telomerase, for example, in order to regulate (e.g., inhibit) cell proliferation in vitro.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other telomerase inhibitors, other anticancer agents, other antiproliferative agents, etc.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be an animal, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one preferred embodiment, the subject is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Suitable carriers, diluents, excipients, etc. can be found in standard pharmaceutical texts. See, for example, *Handbook fo Pharmaceutical Additives*, 2nd Edition (eds. M. Ash and I. Ash), 2001 (Synapse Information Resources, Inc., Endicott, N.Y., USA), *Remington's Pharmaceutical Sciences*, 18th edition, Mack Publishing Company, Easton, Pa., 1990; and *Handbook of Pharmaceutical Excipients*, 2nd edition, 1994.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier + which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in a the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection),: include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active ingredient is a salt, an ester, prodrug, or the like, the amount administered is calculated on the basis the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound, etc.

The written instructions may also include a list of indications for which the active ingredient is a suitable treatment.

EXAMPLES

The following are examples are provided solely to illustrate the present invention and are not intended to-limit the scope of the invention, as described herein.

General Procedures

Melting points (mp) were recorded on a Leica Galen III hot-stage melting point apparatus and are uncorrected. $^1$H-NMR spectra were recorded at 250 MHz on a Bruker AC250 spectrometer in either $d_6$-Me$_2$SO or CDCl$_3$ solution at 303±1 K using Me$_4$Si (TMS) as internal standard. EI (70 eV), FAB and high resolution accurate mass spectra were determined by The School of Pharmacy (University of London, UK). Elemental analyses were carried out by Medac Ltd. (Brunel Science Center, Egham, Surrey, UK); results for elements indicated by symbols were within 0.4% of theoretical values. TLC was carried out on silica gel (Merck 60F-254) using CHCl$_3$/MeOH (0–20% MeOH) as eluent, with visualization at 254 and 366 nm. Organic solutions were dried over sodium sulphate.

General Procedure for Preparation of 3,6-Aminoacridines

To a suspension of NaH (80% in mineral oil) (60 mg) in DMF (10 mL) was added a solution of 3,6-bis(tert-butoxycarbonylamino)acridine (200 mg, 0.49 mmol) in DMF (15 mL), and this reaction mixture was stirred at room temperature for 1 h.

A solution of the intended chloroamine (3 equiv.) in DMF (10 mL) was added and the reaction mixture heated under reflux for 18 h. The reaction mixture was poured into water (75 mL), and extracted with CHCl$_3$ (4×50 mL) and ethyl acetate (2×30 mL). The organic extracts were washed with brine (30 mL), dried (Na$_2$SO$_4$), and reduced to dryness under vacuum. The resultant product was dissolved in ethyl acetate (10 mL) and treated with conc. HCl (1 mL). The reaction mixture was stirred overnight at room temperature. The resultant solid was filtered off and washed with Et$_2$O prior to dissolving in water (40 mL). The aqueous solution was made basic to pH 7/8 by addition of dilute ammonia and extracted with CHCl$_3$ (4×25 mL). The organic extracts were combined, washed with brine (30 mL), dried (Na$_2$SO$_4$) and concentrated under vacuum to give the desired product.

General Procedure for Preparation of Chloramines

Chloroamines commercially available only as hydrochloride salts were first treated with excess KOH in DMF to obtain the free base.

Chloroamines ones not commercially available were prepared synthetically. See, for example, Yale et al., 1955.

To a solution of 1-bromo-3-chloropropane (20.3 mmol, I eq.) in diethyl ether (10 mL), was added the intended amine (2 eq.). This clear colourless solution was heated under gentle reflux for 1–48 hrs. The reaction mixture was allowed to cool to room temperature and water (2 mL) added. The ether layer was extracted with dilute HCl (3×5 mL). The acidic extracts were combined and made basic to pH 8/9 with ammonium hydroxide solution. This aqueous layer was extracted with diethyl ether (4×25 mL), the ethereal extracts were combined, washed with brine (25 mL), dried (Na$_2$SO$_4$) and concentrated to yield the product as a colourless oil.

Example 1

3,6-Bis(diallylamino)acridine

BSU-SB-36/102

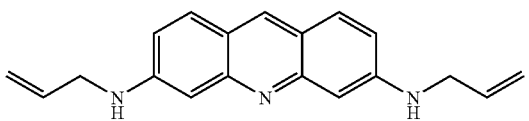

3,6-Bis(tert-butoxycarbonylamino)-acridine, JH-ACl-5 (200 mg, 0.49 mmol) was treated with allyl bromide (0.32 g) according to the general procedure to furnish the desired product BSU-SB-36/102 (0.22 g, quantitative) as a dark red hygroscopic solid.

$^1$H-NMR (DMSO) (BSU-SB-36/102) δ 3.81–3.86 (4 H, d, J 4.9 Hz, HNCH$_2$CH=CH$_2$), 5.15–5.20 (2 H, dd, J 10.3 and 1.8 Hz, HNCH$_2$CH=CH$_2$-cis), 5.28–5.35 (2 H, dd, J 17.2 and 1.8 Hz, HNCH$_2$CH=CH$_2$-trans), 5.89–6.04 (2 H, m, HNCH$_2$CH=CH$_2$), 6.60 (2 H, m, H-4, 5), 6.69–6.73 (2 H, m, HNCH$_2$), 6.90–6.95 (2 H, dd, J 9.0 and 2.1 Hz, H-7, 2), 7.62–7.65 (2 H, d, J 9.0 Hz, H-1, 8), 8.32 (1 H, s, H-9). m/z (EI) 289/290 (C$_{19}$H$_{19}$N$_3$ M+H, requires 290).

Example 2

Monohydrochloride Salt

SB-ACl-03

The monohydrochloride addition salt, SB-ACl-03, of the compound in the previous example, was also prepared by treatment with HCl.

Example 3

3,6-Bis[(N,N-dimethylaminopropyl)amino]acridine

BSU-SB-36/100

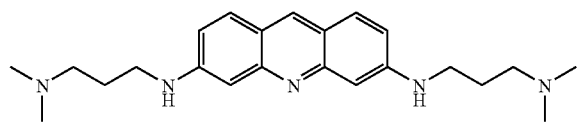

3,6-Bis(tert-butoxycarbonylamino)acridine, JH-ACl-5 (200 mg, 0.49 mmol) was treated N,N-dimethylpropylchloride (0.23 g) according to the general procedure furnish the desired product BSU-SB-36/100 (0.20 g, 100%) as a dark red residue.

$^1$H-NMR (DMSO) (BSU-SB-36/100) δ 1.70–14.81 (4 H, m, HNCH$_2$CH$_2$CH$_2$N), 2.16 (12 H, s, N(CH$_3$)$_2$), 2.31–2.37 (4 H, m, HNCH$_2$CH$_2$CH$_2$N), 3.12–3.20 (4 H, m, HNCH$_2$CH$_2$CH$_2$N), 6.37–6.41 (2 H, m, HNCH$_2$), 6.84–6.88 (2 H, dd, J 9.0 and 2.1 Hz, m, J 1.7 Hz, H-4, 5), 6.84–6.88 (2 H, dd, J 9.0 and 2.1 Hz, H-2, 7), 7.57–7.61 (2 H, d, J 9.0Hz, H-1, 8), 8.27 (1 H, s, H-9). m/z (EI) 380.2832, (C$_{23}$H$_{33}$N$_5$ M+H requires 380.2814).

Example 4

Trihydrochloride Salt

SB-ACl-04

The trihydrochloride addition salt, SB-ACl-04, of the compound in the previous example, was also prepared by treatment with HCl.

Example 5

3,6-Bis[(N,N-diethylaminoethyl)amino]acridine

BSU-SB-36/104

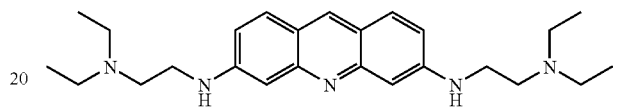

3,6-Bis(tert-butoxycarbonylamino)-acridine, JH-ACl-5 (200 mg, 0.49 mmol) was treated N,N-diisopropylethylchloride (0.25 g) according to the general procedure to furnish the desired product BSU-SB-36/104 (0.20 g, 100%) as a dark red residue.

$^1$H-NMR (DMSO) (BSU-SB-36/104) δ 0.92–0.98 (12 H, t, J 7.1 Hz, N(CH$_2$CH$_3$)$_2$), 2.50–2.56 (8 H, q, N(CH$_2$CH$_3$)$_2$), 2.60–2.66 (4 H, m, HNCH$_2$CH$_2$N), 3.15–3.22 (4 H, m, HNCH$_2$CH$_2$N), 6.18–6.23 (2 H, m, J 5.2 Hz, HNCH$_2$), 6.57 (2 H, m, H-4, 5), 6.84–6.89 (2 H, dd, J9.0 and 2.1 Hz, H-7, 2), 7.56–7.59 (2 H, d, J 9.0 Hz, H-1, 8), 8.27 (1 H, s, H-9). m/z (EI), 407.3045 (C$_{25}$H$_{37}$N$_5$ M+H requires 407.3048).

Example 6

Trihydrochloride Salt

SB-ACl-05

The trihydrochloride addition salt, SB-ACl-05, of the compound in the previous example, was also prepared by treatment with HCl.

Example 7

3,6-Bis[(N,N-diisoproyplaminoethyl)amino]acridine

BSU-SB-36/108

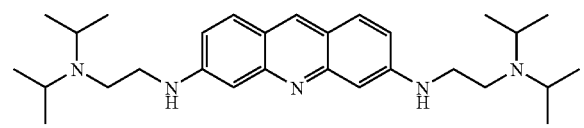

3,6-Bis(tert-butoxycarbonylamino)acridine JH-ACl-5 (200 mg, 0.49 mmol) was treated with N,N-diisopropylethylchloride (hydrochloride salt) (0.3 g) according to the general procedure to furnish the desired product BSU-SB-36/108 (0.29 g, 100%) as an orange residue.

$^1$H-NMR (DMSO) (BSU-SB-36/108) δ 0.92–1.03 (24 H, d, J 6.5 Hz, N(CHCH$_2$CH$_3$)$_2$), 2.64–2.69 (4 H, m, HNCH$_2$CH$_2$N(i-Pr)$_2$), 2.98–3.09 (4 H, m, N(CHCH$_2$CH$_3$)$_2$); 3.10–3.18 (4 H, m, HNCH$_2$CH$_2$N(i-Pr)$_2$), 6.19 (2 H, m, HNCH$_2$), 6.59 (2 H, m, H-4, 5), 6.84–6.89 (2 H, dd, J 9.0 and 2.1 Hz, H-2, 7), 7.59–7.62 (2 H, d, J 9.0 Hz, H-1, 8), 8;29 (1 H, s, H-9). m/z (EI), 464.3770 ($C_{25}H_{37}N_5$ M+H requires 464.3753).

Example 8

Trihydrochloride Salt

SB-ACl-06

The trihydrochloride addition salt, SB-ACl-06, of the compound in the previous example, was also prepared by treatment with HCl.

Example 9

3,6-Bis[(N,N-dimethylaminoethyl)amino]acridine

BSU-SB-36/106

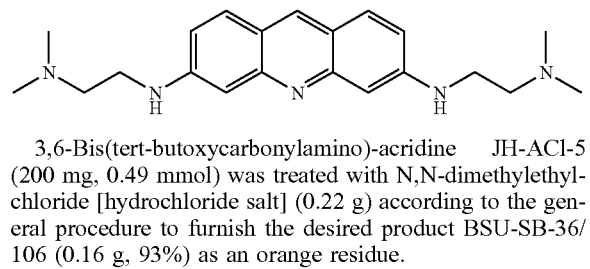

3,6-Bis(tert-butoxycarbonylamino)-acridine JH-ACl-5 (200 mg, 0.49 mmol) was treated with N,N-dimethylethylchloride [hydrochloride salt] (0.22 g) according to the general procedure to furnish the desired product BSU-SB-36/106 (0.16 g, 93%) as an orange residue.

$^1$H-NMR (DMSO) (BSU-SB-36/106) δ 2.19 (12 H, s, N($CH_3$)$_2$), 2.49–2.53 (4 H, m, HN$CH_2CH_2$N), 3.18–3.25 (4 H, m, HN$CH_2CH_2$N), 6.13–6.17 (2 H, t, J 5.2 Hz, HN$CH_2$), 6.59 (2 H, m, H-4, 5), 6.87–6.92 (2 H. dd, J 9.0 and 2.1 Hz, H-2, 7), 7.56–7.59 (2 H, d, J 9.0 Hz, H-1, 8), 8.26 (1 H, s, H-9). m/z (EI), 352.2525 ($C_{21}H_{29}N$ M+H requires 352.2501).

Example 10

Trihydrochloride Salt

SB-ACl-10

The trihydrochloride addition salt, SB-ACl-10, of the compound in the previous example, was also prepared by treatment with HCl.

Example 11

3,6-Bis[(3-pyrolidino)propylamino]acridine

BSU-SB-36/228

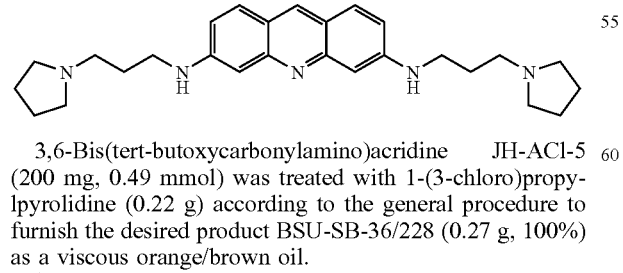

3,6-Bis(tert-butoxycarbonylamino)acridine JH-ACl-5 (200 mg, 0.49 mmol) was treated with 1-(3-chloro)propylpyrolidine (0.22 g) according to the general procedure to furnish the desired product BSU-SB-36/228 (0.27 g, 100%) as a viscous orange/brown oil.

$^1$H-NMR (CDCl$_3$) (BSU-SB-36/228) δ 1.78–1.83 (8 H, m, N($CH_2CH_2$)$_2$), 1.89–1.94 (4 H, m, HN$CH_2CH_2CH_2$N), 2.52–2.57 (8 H, m, N($CH_2CH_2$)$_2$), 2.62–2.68 (4 H, t, J 6.7 Hz, HN($CH_2CH_2CH_2$)N), 3.35–3.40 (4 H, bm, HN($CH_2CH_2CH_2$)N), 5.39 (2 H, bs, HN), 6.70–6.74 (2 H, dd, J 2.2 and 8.9 Hz, H-2,7), 6.91–6.92 (2 H, m, H-4,5), 7.56–7.60 (2 H, d, J 8.9 Hz, H-1,8), 8.22 (1 H, s, H-9). m/z (EI), 432.3128 ($C_{27}H_{38}N_5$ M–H requires 432.3127).

Example 12

Trihydrochloride Salt

SB-ACl-23

The trihydrochloride addition salt, SB-ACl-23, of the compound in the previous example, was also prepared by treatment with HCl.

Example 13

3,6-Bis[(3-diethylamino)propylamino]acridine

BSU-SB-36/234

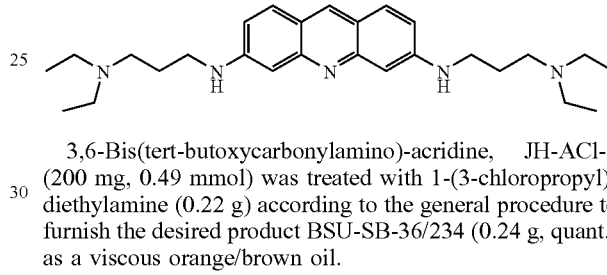

3,6-Bis(tert-butoxycarbonylamino)-acridine, JH-ACl-5 (200 mg, 0.49 mmol) was treated with 1-(3-chloropropyl)-diethylamine (0.22 g) according to the general procedure to furnish the desired product BSU-SB-36/234 (0.24 g, quant.) as a viscous orange/brown oil.

$^1$H-NMR (CDCl$_3$) (BSU-SB-36/234) δ 1.03–1.09 (12 H, t, J 7.1 Hz, $CH_3$), 1.80–1.90 (4 H, m, HN($CH_2CH_2CH_2$)N), 2.48–2.62 (12 H, m, $CH_2CH_3$ and HN($CH_2CH_2CH_2$)N), 3.33–3.38 (4 H, bt, J 6.0 Hz, HN($CH_2CH_2CH_2$)N), 5.79 (2 H, bs, HN), 6.71–6.75 (2 H, dd, J 2.2 and 8.9 Hz, H-2,7), 6.90 (2 H, s, H-4,5), 7.56–7.59 (2 H. d, J 8.9 Hz, H-1,8), 8.21 (1 H. s, H-9). m/z (EI), 436.3400 ($C_{27}H_{42}N_5$ M–H requires 436.3440).

Example 14

Trihydrochloride Salt

SB-ACl-24

The trihydrochloride addition salt, SB-ACl-24, of the compound in the previous example, was also prepared by treatment with HCl.

Example 15

3,6-Bis[(3-piperidino)propylamino]acridine

BSU-SB-36/236

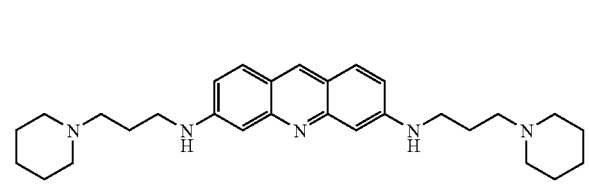

3,6-Bis(tert-butoxycarbonylamino)acridine JH-ACl-5 (200 mg, 0.49 mmol) was treated 1-(3-chloro)propylpiperidine (0.24 g) according to the general procedure furnish the desired product BSU-SB-36/236 (0.29 g, 100%) as orange/brown oil.

$^1$H-NMR (CDCl$_3$) (BSU-SB-36/236) δ 1.24–1.67 (12 H, m, N[(CH$_2$ CH$_2$)$_2$CH$_2$]), 1.79–1.92 (4 H, m, HN(CH$_2$CH$_2$CH$_2$)N), 2.21–2.58 (12 H, m, N[(CH$_2$ CH$_2$)$_2$CH$_2$] and HN(CH$_2$CH$_2$CH$_2$)N), 3.32–3.37 (4 H, t, J 6.1 Hz, HN(CH$_2$CH$_2$CH$_2$)N), 5.92 (2 H, bs, HN), 6.73–6.77 (2 H, dd, J 2.2 and 8.9 Hz, H-2,7), 6.89 (2 H, s, H-4,5), 7.56–7.59 (2 H, d, J 8.9 Hz, H-1,8), 8.21 (1 H, s, H-9). m/z (EI), 460.3448 (C$_{32}$H$_{42}$N$_5$ M–H requires 460.3440).

Example 16

Trihydrochloride Salt

SB-ACl-25

The trihydrochloride addition salt, SB-ACl-25, of the compound in the previous example, was also prepared by treatment with HCl.

Example 17

3,6-Bis[(3-phenylamino)propylamino]acridine

BSU-SB-36a/030

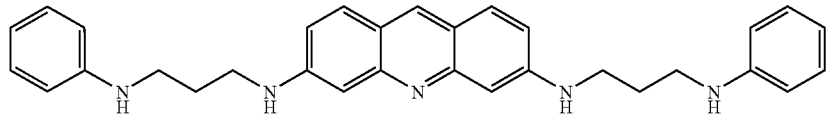

3,6-Bis(tert-butoxycarbonylamino)acridine JH-ACl-5 (200 mg, 0.49 mmol) was treated (3-chloro)propylphenylamine (0.25 g) according to the general procedure to furnish the desired product BSU-SB-36a/030 (0.14 g, 60%) as orange/brown oil.

$^1$H-NMR (CDCl$_3$) (BSU-SB-36a/030) δ 1.18–1.24 (4 H, t, J 7.0 Hz, HN(CH$_2$CH$_2$CH$_2$)N), 2.00–2.05 (4 H, t, J 6.7 Hz, HN(CH$_2$CH$_2$CH$_2$)N), 3.26–3.31 (2 H, bs, HN), 3.41–3.52 (4 H, m, HN(CH$_2$CH$_2$CH$_2$)N), 3.73 (1 H, bs, NH), 4.31–4.36 (1 H, bs, NH), 6.61–6.65 (4 H, dd, J 8.6 Hz, phenyl), 6.72–6.77 (4 H, m, phenyl), 6.97 (2 H, s, H-2,7), 7.16–7.22 (4 H, m, H-4,5 and phenyl), 7.59–7.63 (2 H, d, J 9.0 Hz, H-1,8), 8.25 (1 H, s, H-9). m/z (EI), 476.2831(C$_{31}$H$_{34}$N$_5$ M–H requires 476.2814).

Example 18

Trihydrochloride Salt

SB-ACl-27

The trihydrochloride addition salt, SB-ACl-27, of the compound in the previous example, was also prepared by treatment with HCl.

Example 19

3,6-Bis[(4-chloro)butylamino]acridine

BSU-SB-36a/026

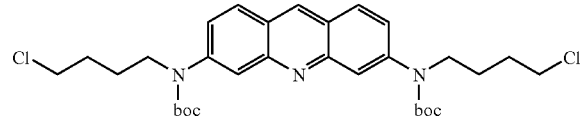

To a suspension of NaH (80% in mineral oil) (60 mg) in DMF (10 mL) was added a solution of 3,6-bis(tert-butoxycarbonylamino)acridine, JH-ACl-5 (200 mg, 0.49 mmol) in DMF (15 mL), and this reaction mixture was stirred at room temperature for 1 hr. A solution of 4-chloro-1-bromo-butane (0.13 mL, 1.1 mmol) in DMF (5 mL) was added and mixture stirred at room temperature for 4.5 h. The reaction was quenched by addition of H$_2$O (75 mL) and then extracted chloroform (4×20 mL). The organic extracts were combined, washed with brine (20 mL), dried (Na$_2$SO$_4$) and concentrated under vacuum to furnish the desired product BSU-SB-36a/026, as a brown oil (100%).

$^1$H-NMR (CDCl$_3$) (BSU-SB-36a/026) δ 1.48 (18 H, s, CH$_3$), 1.80–1.83 (8 H, m, BOCNCH$_2$CH$_2$CH$_2$CH$_2$Cl), 3.52–3.57 (4 H, bt, BOCNCH$_2$CH$_2$CH$_2$CH$_2$Cl), 3.86–3.92 (4 H, bt, BOCNCH$_2$CH$_2$CH$_2$CH$_2$Cl), 7.48–7.52 (2 H, dd, J 9.1 and 2.2 Hz, H-2, 7), 7.91–7.95 (4 H, m, H-1,8,4,5), 8.70 (1 H, s, H-9).

Example 20

3,6-Bis[(4-pyrolidino)butylamino]acridine

BSU-SB-36a/028

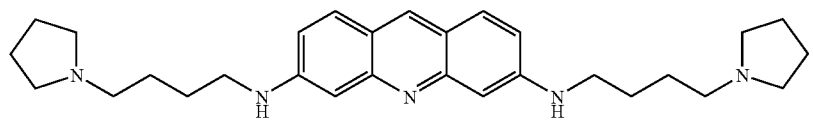

A solution of the dichloroacridine (BSU-SB-36a/026) (450 mg) in EtOH (15 ml) was treated with pyrrolidine under gentle reflux for 7 days. The reaction mixture was concentrated to dryness and then redissolved in water (30 mL). This aqueous solution was made basic to pH 8/9 by addition of ammonium hydroxide solution and extracted with $CHCl_3$ (3×25 mL). The combined organic extracts were washed with brine (20 mL), dried ($NaSO_4$) and reduced to dryness under vacuum. The resultant product was redissolved in ethyl acetate and treated with conc.HCl to furnish the desired product BSU-SB-36a/028 (0.26 g,100%) as an orange/brown oil. The product was purified by flash chromatography by gradient elution from 100% chloroform (0.1 mL $NEt_3$/100 mL) to 100% methanol (0.1 mL $NEt_3$/100 mL). Quantity of pure product obtained –0.15 g, 65%.

$^1$H-NMR ($CDCl_3$) (BSU-SB-36a/028) δ 1.64–1.83 (16 H, m, $N(CH_2CH_2)_2$, $HNCH_2CH_2CH_2CH_2N$), 2.47–2.55 (12 H, m, $HNCH_2CH_2CH_2CH_2N$, $N(CH_2CH_2)_2$), 3.27–3.32 (4 H, t, J 6.5 Hz, $HNCH_2CH_2CH_2CH_2N$), 4.76 (1 H, bs, HN), 6.70–6.75 (2 H, dd, J 2.2 and 8.9 Hz, H-2,7), 6.93 (2 H, s, H4,5), 7.57–7.60 (2 H, d, J 8.9 Hz, H-1,8), 8.22 (1 H, s, H-9). m/z (EI), 460.3448 ($C_{29}H_{42}N_5Cl_3$ M−H requires 460.3440).

Example 21

Trihydrochloride Salt

SB-ACl-26

The trihydrochloride addition salt, SB-ACl-26, of the compound in the previous example, was also prepared by treatment with HCl.

Example 22

3,6-Bis[(4-diethylamino)butylamino]-acridine

BSU-SB-36a/038

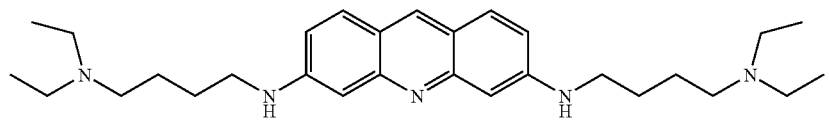

A solution of dichloroacridine (BSU-SB-36a/026) (290 mg) in EtOH (15 ml) was treated with diethylamine and refluxed for 11 days. The reaction mixture was concentrated to dryness under vacuum then redissolved in water (30 mL). This aqueous solution was made basic to pH 8/9 by addition of ammonium hydroxide solution and extracted with chloroform (3×25 mL). The combined organic extracts were washed with brine (20 mL), dried ($NaSO_4$) and concentrated under vacuum. The resultant product was redissolved in EtOAc and treated with conc. HCl to furnish the desired product BSU-SB-36a/038 as a brown oil. The product was purified by flash chromatography by gradient elution from 100% chloroform (0.1 mL $NEt_3$/100 mL) to 100% methanol (0.1 mL $NEt_3$/100 mL). 0.15 g, 65%. m/z (EI), 464.5 ($C_{29}H_{45}N_5$ M+H requires 463.7).

Example 23

Trihydrochloride Salt

SB-ACl-28

The trihydrochloride addition salt, SB-ACl-28, of the compound in the previous example, was also prepared by treatment with HCl. Product hygroscopic.

$^1$H-NMR (DMSO) (SB-ACl-28) δ 0.92–0.98 (12 H, t, J 7.1 Hz, $CH_2CH3$), 1.53–1.77 (8 H, m, $HNCH_2CH_2CH_2CH_2N$), 2.38–2.48 (12 H, m, $HNCH_2CH_2CH_2CH_2N$, $NCH_2CH_3$), 3.14–3.16 (4 H, m, $HNCH_2CH_2CH_2CH_2N$), 6.42 (2 H, bs, NH), 6.57 (2H, s, H-4,5), 6.86–6.90 (2 H, dd, J 1.9 and 9.0 Hz, H-2,7), 7.58–7.61 (2 h, d, J 9.0 Hz, H-1,8), 8.29 (1 H, s, H-9).

Example 24

3,6-Bis[2-(2-methoxy-ethoxy)ethylamino]acridine

BSU-SB-36/112

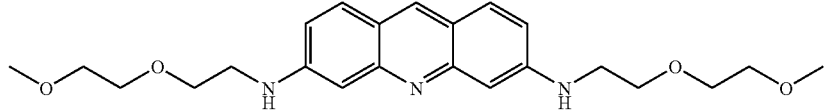

3,6-Bis(tert-butoxycarbonylamino)acridine JH-ACl-5 (200 mg, 0.49 mmol) was treated 1-(2-bromo)ethoxy-2- methoxyethane (0.3 g) according to the general procedure furnish the desired product BSU-SB-36/112 (0.16 g, 80%) as a dark brown viscous oil.

$^1$H-NMR (CDCl$_3$) (BSU-SB-36/112) δ 3.41 (6 H, s, Me), 3.46–3.52 (4 H, m, CH$_2$), 3.56–3.60 (4 H, m, CH$_2$), 3.63–3.68 (4 H, m, CH$_2$), 3.79–3.83 (4 H, m, CH$_2$), 4.73 (2 H, br, NH), 6.78–6.83 (2 H, dd, J 8.9 and 2.2 Hz, H-2,7), 6.98–6.99 (2 H, m, H-4, 5), 7.60–7.63 (2 H, d, J 8.9 Hz, H-1,8), 8.26 (1 H, s, H-9).

Example 25

Trihydrochloride Salt

SB-ACl-08

The trihydrochloride addition salt, SB-ACl-08, of the compound in the previous example, was also prepared by treatment with HCl, to yield a viscous residue.

Example 26

3,6-Bis(2-ethoxyethylamino)acridine

BSU-SB-36/114

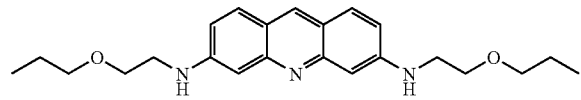

3,6-Bis(tert-butoxycarbonylamino)acridine JH-ACl-5 (200 mg, 0.49 mmol) was treated 2-chloro-ethoxyethane (0.16 mL) according to the general to furnish the desired product BSU-SB-36/114 (0.16 g, 83%) as a dark brown viscous oil.

$^1$H-NMR (CDCl$_3$) (BSU-SB-36/114) δ 1.22–1.27 (6 H, t, J 7.0 Hz, Me), 3.44–3.50 (4 H, m, CH$_2$), 3.52–3.61 (4 H, q, J 14.0 and 7.0 Hz, CH$_2$), 3.72–3.76 (4 H, m, CH$_2$), 4.54 (2 H, br NH), 6.79–6.84 (2 H, dd, J 9.0 and 2.2 Hz, H-2,7), 6.99–7.00 (2 H, m, H-4, 5), 7.60–7.64 (2 H, d, J 9.0 Hz, H-1,8), 8.27 (1 H, s, H-9).

Example 27

Trihydrochloride Salt

SB-ACl-09

The trihydrochloride addition salt, SB-ACl-09, of the compound in the previous example, was also prepared by treatment with HCl, to yield a viscous residue.

Biological Data

Tag Polymerase Assay

Compounds were tested using a Taq assay to eliminate broad-spectrum polymerase inhibitors and thus filter out any false positives which might have occurred in the TRAP assay. Thus, preferred compounds are "Taq-negative." Compounds were tested as their acid addition salts at various final concentrations (0.1, 0.5, 1, 5, 10, 20 and 50 μM) in a PCR 50 μL master mix containing 10 ng pCl-neo mammalian expression vector (Promega, Southampton, UK) and forward (GGAGTTCCGCGTTACATAAC) and reverse (GTCTGCTCGAAGCATTAACC) primers (200 nmol) as described in the art (see, e.g., Perry et al., 1998a). The product of approximately 1 kb was visualized on a 2% w/w agarose gel following amplification (30 cycles of 94° C. for 1 min, 55° C. for 1 min and 72° C. for 2.5 min). The Taq assay was carried out until no Taq polymerase inhibition was observed. All compounds were found to be Taq negative.

Modified Telomeric Repeat Amplification Protocol (TRAP) Assay

The ability of compounds to inhibit telomerase in a cell-free assay was assessed with a modified TRAP assay using extracts from exponentially growing A2780 human ovarian carcinoma cells. The TRAP assay was performed in 2 steps: (a) telomerase-mediated extension of the forward primer (TS: 5'-AATCCGTCGAGCAGAGTT, Oswel Ltd., Southampton, UK) contained in a 40 μL reaction mix comprising TRAP buffer (20 mM Tris-HCl (pH 8.3), 68 mM KCl, 1.5 mM MgCl$_2$, 1 mM EGTA, 0.05% v/v Tween 20), 0.05 μg bovine serum albumin, 50 μM of each deoxynucleotide triphosphate, 0.1 μg TS primer, and 3 pCi of [α-$^{32}$P] dCTP (Amersham pic, UK). Protein (40 ng or 20 ng) was then incubated with the reaction mix+agent (acid addition and quaternary dimethiodide salts) at final concentrations of up to 50 μM for 20 min at 25° C. A lysis buffer (no protein) control, heat-inactivated protein control, and 50% protein (20 ng or 10 ng) control were included in each assay; and (b) while heating at 80° C. in a PCR block of a thermal cycler (Hybaid, UK) for 5 min to inactivate telomerase activity, 0.1 μg of reverse CX primer (3'-AATCCCATTCCCATTC-CCATTCCC-5') and 2 Units of Taq DNA polymerase ("red hot", Advanced Biotechnologies) were added. A 3-step PCR was then performed: 94° C. for 30 s, 50° C. for 30 s, and 72° C. for 1 min for 31 cycles. Telomerase-extended PCR products in the presence or absence of compounds were then determined either by electrophoretic separation using 8% w/w acrylamide denaturing gels and analysis by phosphorimaging or autoradiography, or by harvesting on Whatman filters (25 mm glass microfibre) and analysis by liquid scintillation counting. The data are summarized in Table 1.

Growth Inhibition Assay

Growth inhibition was measured in three human ovarian carcinoma cell lines (A2780, CH1, and SKOV-3) and one human cervix carcinoma cell line (A431) using the sulforhodamine B (SRB) assay. Briefly, between 3000 and 6000 cells were seeded into the wells of 96-well microtiter plates and allowed to attach overnight. Compounds (acid addition and quaternary dimethiodide salts) were dissolved at 500 μM in water and immediately added to wells in quadruplicate at final concentrations of 0.05, 0.25, 1, 5 and 25 μM. Following an incubation period of 96 hr, remaining cells were fixed with ice-cold 10% w/v trichloroacetic acid (30 min) and stained with 0.4% SRB in 1% v/v acetic acid (15 min). Mean absorbance at 540 nm for each drug concentration was expressed as a percentage of the control untreated well absorbance, and IC$_{50}$ values (concentration required to inhibit cell growth by 50%) were determined for each agent. The data are summarized in Table 1.

TABLE 1

Telomerase Inhibitory Activity and Cytotoxicity for Salts

| Compound | | tel$IC_{50}$ | Cytotoxicity - $IC_{50}$ (μM) | | | |
|---|---|---|---|---|---|---|
| Class | Ref. No. | (μM) | A2780 | CH1 | SKOV-3 | A431 |
| 3,6-diamine | SB-ACI-03 | 1.75 | 4.4 | 0.7 | 3.5 | 1 |
| 3,6-diamine | SB-ACI-05 | 0.54 | 0.1 | 0.2 | 0.7 | 0.2 |
| 3,6-diamine | SB-ACI-06 | 0.59 | 0.4 | 0.6 | 1.3 | 1 |
| 3,6-diamine | SB-ACI-10 | 0.48 | 0.2 | 0.1 | 0.2 | 0.2 |
| 3,6-diamine | SB-ACI-04 | 0.20 | 1.8 | 2 | 3.9 | 0.7 |
| 3,6-diamine | SB-ACI-23 | 0.181 | | | 1.6[a] | |
| 3,6-diamine | SB-ACI-24 | 0.222 | | | 1.8[a] | |
| 3,6-diamine | SB-ACI-25 | 0.218 | | | 0.5[a] | |
| 3,6-diamine | SB-ACI-27 | 16.8 | | | 1.7[a] | |
| 3,6-diamine | SB-ACI-26 | 0.153 | | | 2.5[a] | |
| 3,6-diamine | SB-ACI-28 | 0.205 | | | 6.3[a] | |

[a] mean value for the four (4) cell lines.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Alberti, P., et al., 2002, "Benzoindoloquinolines Interact with DNA Tetraplexes and Inhibit Telomerase," *Bioorganic & Medicinal Chemistry Letters*, Vol. 12, pp. 1071–1074.

Autexier, C., 1999, "Telomerase as a Possible Target for Anticancer Therapy," *Chemistry & Biology*, November 1999, Vol. 6, pp. R299–R303.

Bogert, M. T., et al., 1930, "Researches in the Acridine Series. The Synthesis of Isomers of Proflavine and of Neutral Acriflavine," *Collect. Czech. Chem. Comm.*, Vol. 2, pp. 383–395.

Bostock-Smith, C. E., et al., 1999, "Molecular Recognition between a New Pentacyclic Acridinium Salt and DNA Sequences Investigated by Optical Spectroscopic Techniques, Proton Nuclear Magnetic Resonance Spectroscopy, and Molecular Modeling," *Biochemistry*, Vol. 38, No. 21, pp. 6723–6731.

Carrasco, C., et al., 2002, "Tight Binding of the Antitumour Drug Ditercalcinium to Quaduplex DNA," *ChemBioChem*, Vol. 3, pp. 1235–1241.

Corey, D. R., 2002, "Telomerase Inhibition, Oligonucleotides, and Clinical Trials," *Oncogene*, Vol. 21, pp. 631–637.

Gimenez-Arnau, E. et al., 1998, "Antitumour Polycyclic Acridines, Part 2," *Anti-Cancer Drug Design*, Vol. 13, pp. 125–143.

Gimenez-Arnau, E., et al., 1998, "Antitumour Polycyclic Acridines, Part 4," *Anti-Cancer Drug Design*, Vol. 13, pp. 431–451.

Goldberg, A. A. and Kelly, W., 1946, "29. Synthesis of Diaminoacridines. Part I," *J. Chem. Soc.*, p. 102–111.

Goldstein, H., and de Simo, M., 1927, "Quelques derives de l'acide phenyl-anthranilique III," *Helv. Chim. Acta.*, Vol. 10, p. 603–606.

Gomez, D., et al., 2002, "Detection of Telomerase Inhibitors Based on G-Quadruplex Ligands by a Modified Telomeric Repeat Amplification Protocol Assay," *Cancer Research*, Vol. 62, pp. 3365–3368.

Gowan, S. M., et al., 2002, "A G-Quadruplex-Interactive Potent Small-Molecule Inhibitor of Telomerase Exhibiting in Vitro and in Vivo Antitumour Activity," *Molecular Pharmacology*, Vol. 61, No. 5, pp. 1154–1162.

Hagan, D. H., et al., 1997, "Antitumour Polycyclic Acridines, Part 1," *J. Chem. Soc., Perkin Trans.* 1, pp. 2739–2746.

Hagan, D. H., et al., 1998, "Antitumour Polycyclic Acridines, Part 3," *J. Chem. Soc., Perkin Trans.* 1, p. 915–923.

Harrison, R. J., et al., 1999, "Human Telomerase Inhibition by Substituted Acridine Derivatives," *Bioorganic & Medicinal Chemistry Letters*, Vol. 9, pp. 2463–2468.

Herbert, B.-S., et al., 2001, "Telomerase and Breast Cancer," *Breast Cancer Research*, Vol. 3, pp. 146–149.

I. G. Farbenindustrie Akt.-Ges in Frankfurt a.M., 1930, "Verfahren zur Darstellung von Aminoalkylaminosubstitutionprodukten der Acridinreihe," German Patent No. DE 488 890, published 23 Jan. 1930.

Julino, M., et al., 1998, "Antitumour Polycyclic Acridines, Part 5," *J. Chem. Soc., Perkin Trans.* 1, pp. 1677–1684.

Kern, J. T., et al., 2002, "The Relationship between Ligand Aggregation and G-Quadruplex DNA Selectivity in a Series of 3,4,9,10-Perylenetetracarboxylic Acid Diimides," *Biochemistry*, Vol. 41, pp. 11379–11389.

Kim, M.-Y., et al., 2002, "Telomestatin, a Potent Telomerase Inhibitor That Interacts Quite Specifically with the Human Telomeric Intramolecular G-Quadruplex," *J. Amer. Chem. Soc.*, Vol. 124, No. 10, pp. 2098–2099.

Korolev, B. A., et al., 1976, "Preparation of 2-Aminoacridan by the Reduction of 2-Amino-9-Acridanone with Biborane," *J. Gen. Chem. USSR (Engl. Trans.)*, Vol. 46, pp. 2250–2252.

Korolev, B. A., et al., 1977, "Acridines. II. Selective Reduction of Nitro Derivatives of 2-Amino-9-Acridanone with Diborane," *J. Gen. Chem. USSR (Engl. Trans.)*, Vol. 47, pp. 2118–2122.

Lorente, A., et al., 1996, "Syntheses of Imidazole-Acridine Conjugates as Ribonuclease A Mimics," *Tetrahedron Letters*, Vol. 37, No. 25, pp. 4417–4420.

Matsumura, K., 1929, "The Synthesis of Certain Acridine Compounds," *J. Amer. Chem. Soc.*, Vol. 51, pp. 816–820.

Mergny, J.-L., et al., 2002, "Natural and Pharmacological Regulation of Telomerase," *Nucleic Acids Research*, Vol. 30, No. 4, pp. 839–865.

Neidle, S., et al., 1999, "Telomerase as an Anti-Cancer Target: Current Status and Future Prospects," *Anti-Cancer Drug Design*, Vol. 14, pp. 341–347.

Neidle, S., et al., 2002, "Telomere Maintenance as a Target for Anticancer Drug Discovery," *Nature Reviews*, Vol. 1, May 2002, pp. 383–393.

Neidle, S., et al., 2002, International Patent Application No. PCT/GB01/03046, publication number WO 02/08193 published 17 Jan. 2002.

Parkinson, G. N., et al., 2002, "Crystal structure of parallel quadruplexes from human telomeric DNA," *Nature*, Vol. 417, 20 Jun. 2002, pp. 876–880.

Perry, P. J., et al., 1998a, "1,4- and 2,6-Disubstituted Amidoanthracene-9,10-dione Derivatives as Inhibitors of Human Telomerase," *J. Med. Chem.*, Vol. 41, No. 17, pp. 3253–3260.

Perry, P. J., et al., 1998b, "Human Telomerase Inhibition by Regioisomeric Disubstitued Amidoanthracene-9,10-diones," *J. Med. Chem.*, Vol. 41, No. 24, pp. 4873–4884.

Perry, P. J., et al., 1998c, "Telomeres and Telomerase: Targets for Cancer Chemotherapy?," *Exp. Opin. Ther. Patents*, Vol. 8, No. 12, pp. 1567–1586.

Perry, P. J., et al., 1999a, "Design, Synthesis and Evaluation of Human Telomerase Inhibitors Based Upon a Tetracyclic Structural Motif," *Anti-Cancer Drug Design*, Vol. 14, pp. 373–382.

Perry, P. J., et al., 1999b, "2,7-Disubstituted Amidofluorenone Derivatives as Inhibitors of Human Telomerase," *J. Med. Chem.*, Vol. 42, No. 14, pp. 2679–2684.

Read et al., 24 Apr. 2001, "Structure-based design of selective and potent G quadruplex-mediated telomerase inhibitors," *Proceedings of the National Academy of Science*, Vol. 98, No. 9, pp. 4844–4849.

Rezler, E. M., et al., 2002, "Telomeres and Telomerases as Drug Targets," *Current Opinion in Pharmacology*, Vol. 2, pp. 415–423.

Riou, J. F., et al., 2002, "Cell Senescence and Telomere Shortening Induced by a New Series of Specific G-Quadruplex DNA Ligands," *Proc. Nat. Acad. Sci.*, Vol. 99, No. 5, pp. 2672–2677.

Sharma, S., et al., 1997, "Preclinical and Clinical Strategies for Development of Telomerase and Telomere Inhibitors," *Annals of Oncology*, Vol. 8, pp. 1063–1074.

Shay, J. W., et al., 2002, "Telomerase: A Target for Cancer Therapeutics," *Cancer Cell*, Vol. 2, pp. 257–265.

Sun, D., et al., 1997, "Inhibition of Human Telomerase by a G-Quadruplex-Interactive Compound," *J. Med. Chem.*, Vol. 40, pp. 2113–2116.

Urquidi, V., et al., 1998, "Telomerase in Cancer: Clinical Applications," *Ann. Med.*, Vol. 30, pp. 419–430.

Yale, H. L., 1955, "3-Chloro-10-dialkylaminoalkylphenothiazines," *J. Amer. Chem. Soc.*, Vol. 77, pp. 2270–2272.

The invention claimed is:

1. A compound of the formula:

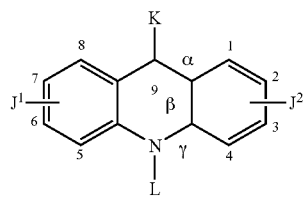

(1)

wherein either:

(a) K is =O, L is —H, α is a single bond, β is a double bond, γ is a single bond ("acridone"); or:
(b) K is a 9-substituent, L is absent, α is a double bond, β is a single bond, γ is a double bond ("acridine");

and wherein:

$J^1$ is a 2- or 3-substituent; and,
$J^2$ is a 6- or 7-substituent;

and wherein $J^1$ and $J^2$ are each independently a group of the formula:

wherein:

$R^{N1}$ is independently a nitrogen substituent and is hydrogen, $C_{1-7}$alkyl, $C_{3-20}$heterocyclyl, or $C_{5-20}$aryl, and is optionally substituted; and, W is independently $C_{3-20}$heterocyclyl, $C_{5-20}$aryl, and is optionally substituted, or W is independently a group of the formula:

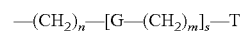

wherein:

n is independently an integer from 1 to 8;
each m is independently an integer from 1 to 8;
s is independently an integer from 0 to 3;
each G is independently —O— or —$NR^N$—;
each $R^N$ is independently a nitrogen substituent;
T is independently a terminal amino group, —$NR^1R^2$ or a terminal ether group, —$OR^5$ and wherein, when K is a 9-substituent, K is a group of the formula:

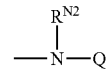

wherein:

$R^{N2}$ is independently a nitrogen substituent and is hydrogen, $C_{1-7}$alkyl, $C_{3-20}$heterocyclyl, or $C_{5-20}$aryl, and is optionally substituted; and, Q is independently $C_{1-7}$alkyl, $C_{3-20}$heterocyclyl, or $C_{5-20}$aryl, and is optionally substituted;

and pharmaceutically acceptable salts, esters, amides, solvates, and protected forms thereof.

2. An acridone compound according to claim 1, wherein K is =O, L is —H, α is a single bond, β is a double bond, γ is a single bond ("acridone"):

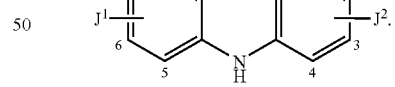

(2)

3. An acridine compound according to claim 1, wherein K is a 9-substituent, L is absent, α is a double bond, β is a single bond, γ is a double bond ("acridine"):

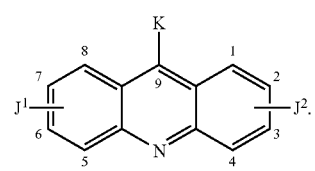

(3)

4. A compound according to claim 1, wherein $J^1$ is a 2-substituent and $J^2$ is a 7-substituent.

5. A compound according to claim 1, wherein $J^1$ is a 3-substituent and $J^2$ is a 6-substituent.

6. A compound according to claim 1, wherein $J^1$ is a 2-substituent and $J^2$ is a 6-substituent; or:
$J^1$ is a 3-substituent and $J^2$ is a 7-substituent.

7. A compound according to claim 1, wherein W is independently $C_{1-7}$alkyl, $C_{3-20}$heterocyclyl, or $C_{5-20}$aryl, and is optionally substituted with one or more groups selected from: amino; ether; amido; acylamino; carboxy; ester; acyloxy; and sulfonamido.

8. A compound according to claim 1, wherein W is independently $C_{1-7}$alkyl and is optionally substituted with one or more groups selected from: amino and ether.

9. A compound according to claim 1, wherein W is independently $C_{1-7}$alkyl substituted with one or more group selected from: amino; ether; polyamino; polyether; and polyether-polyamino.

10. A compound according to claim 1, wherein W is independently a group of the formula:

—$(CH_2)_n$—[G—$(CH_2)_m$]$_s$—T wherein:
n is independently an integer from 1 to 8;
each m is independently an integer from 1 to 8;
s is independently an integer from 0 to 3;
each G is independently —O— or —$NR^N$—;
each $R^N$ is independently a nitrogen substituent;
T is independently a terminal amino group, —$NR^1R^2$ or a terminal ether group, —$OR^5$,
wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

11. A compound according to claim 1, wherein W is independently $C_{1-7}$alkyl substituted with one or more group selected from: amino; ether; amino-$C_{1-7}$alkyl-amino; amino-$C_{1-7}$alkoxy; and ether-$C_{1-7}$alkoxy.

12. A compound according to claim 1, wherein W is independently selected from:
amino-$C_{1-7}$alkyl;
ether-$C_{1-7}$alkyl;
amino-$C_{1-7}$alkyl-amino-$C_{1-7}$alkyl;
amino-$C_{1-7}$alkoxy-$C_{1-7}$alkyl; and,
ether-$C_{1-7}$alkoxy-$C_{1-7}$alkyl.

13. A compound according to claim 1, wherein W is independently selected from the following, wherein —$NR^1R^2$ is a terminal amino group, —$OR^5$ is a terminal ether group, $R^N$ is a nitrogen substituent, and each of n and m is independently an integer from 1 to 8:
—$(CH_2)_n$—$NR^1R^2$;
—$(CH_2)_n$—$OR^5$;
—$(CH_2)_n$—$NR^N$—$(CH_2)_m$—$NR^1R^2$;
—$(CH_2)_n$—$NR^N$—$(CH_2)_m$—$OR^5$;
—$(CH_2)_n$—O—$(CH_2)_m$—$NR^1R^2$; and,
—$(CH_2)_n$—O—$(CH_2)_m$—$OR^5$.

14. A compound according to claim 1, wherein W is independently selected from the following, wherein —$NR^1R^2$ is a terminal amino group, —$OR^5$ is a terminal ether group, $R^N$ is a nitrogen substituent, and m is independently an integer from 1 to 8:
—$(CH_2)_2$—$NR^1R^2$;
—$(CH_2)_2$—$OR^5$;
—$(CH_2)_2$—$NR^N$—$(CH_2)_m$—$NR^1R^2$;
—$(CH_2)_2$—$NR^N$—$(CH_2)_m$—$OR^5$;
—$(CH_2)_2$—O—$(CH_2)_m$—$NR^1R^2$; and,
—$(CH_2)_2$—O—$(CH_2)_m$—$OR^5$;
—$(CH_2)_3$—$NR^1R^2$;
—$(CH_2)_3$—$OR^5$;
—$(CH_2)_3$—$NR^N$—$(CH_2)_m$—$NR^1R^2$;
—$(CH_2)_3$—$NR^N$—$(CH_2)_m$—$OR^5$;
—$(CH_2)_3$—O—$(CH_2)_m$—$NR^1R^2$; and,
—$(CH_2)_3$—O—$(CH_2)_m$—$OR^5$;
—$(CH_2)_4$—$NR^1R^2$;
—$(CH_2)_4$—$OR^5$;
—$(CH_2)_4$—$NR^N$—$(CH_2)_m$—$NR^1R^2$;
—$(CH_2)_4$—$NR^N$—$(CH_2)_m$—$OR^5$;
—$(CH_2)_4$—O—$(CH_2)_m$—$NR^1R^2$; and,
—$(CH_2)_4$—O—$(CH_2)_m$—$OR^5$.

15. A compound according to claim 1, wherein W is independently selected from the following, wherein —$NR^1R^2$ is a terminal amino group, —$OR^5$ is a terminal ether group, and n is independently an integer from 1 to 8:
—$(CH_2)_n$—$NR^1R^2$; and,
—$(CH_2)_n$—$OR^5$.

16. A compound according to claim 1, wherein W is independently selected from the following, wherein —$NR^1R^2$ is a terminal amino group, and —$OR^5$ is a terminal ether group:
—$(CH_2)_2$—$NR^1R^2$; and,
—$(CH_2)_2$—$OR^5$;
—$(CH_2)_3$—$NR^1R^2$; and,
—$(CH_2)_3$—$OR^5$;
—$(CH_2)_4$—$NR^1R^2$; and,
—$(CH_2)_4$—$OR^5$.

17. A compound according to claim 1, wherein W is independently selected from the following, wherein —$NR^1R^2$ is a terminal amino group:
—$(CH_2)_2$—$NR^1R^2$;
—$(CH_2)_3$—$NR^1R^2$; and,
—$(CH_2)_4$—$NR^1R^2$.

18. A compound according to claim 10, wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

19. A compound according to claim 18, wherein said terminal amino group is a secondary amino group, and one of $R^1$ and $R^2$ is —H.

20. A compound according to claim 18, wherein said terminal amino group is a tertiary amino group, and neither $R^1$ nor $R^2$ is —H.

21. A compound according to claim 18, wherein each of $R^1$ and $R^2$ is independently -Me, -Et, -nPr, -iPr, -nBu, or -tBu.

22. A compound according to claim 18, wherein —$NR^1R^2$ is independently —$N(Me)_2$, —$N(Et)_2$, —$N(nPr)_2$, —$N(iPr)_2$, —$N(nBu)_2$, or —$N(tBu)_2$.

23. A compound according to claim 18, wherein —$NR^1R^2$ is independently —NHMe, —NHEt, —NH(nPr), —NH(iPr), —NH(nBu), or —NH(tBu).

24. A compound according to claim 18, wherein $R^1$ and $R^2$, taken together with the nitrogen atom to which they are attached, form a heterocyclic ring having from 3 to 8 ring atoms, which heterocyclic ring is saturated, partially unsaturated, or fully unsaturated, and is optionally substituted.

25. A compound according to claim 18, wherein $R^1$ and $R^2$, taken together with the nitrogen atom to which they are attached form a cyclic amino group of the following formula, wherein q is independently an integer from 2 to 7, and wherein said group is optionally substituted:

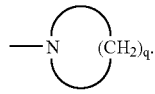

26. A compound according to claim 18, wherein the terminal amino group, —NR¹R², is independently one of the following cyclic amino groups, and is optionally substituted:

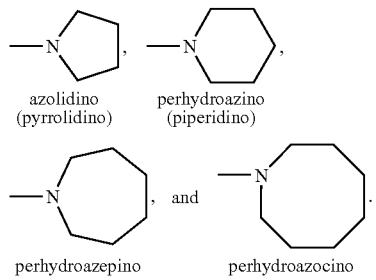

27. A compound according to claim 18, wherein the terminal amino group, —NR¹R², is one of the following groups, and is optionally substituted:

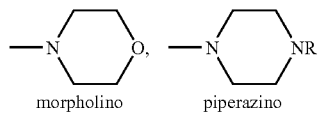

wherein R is an amino substituent, for example, hydrogen, $C_{1-7}$alkyl, $C_{3-20}$heterocyclyl, or $C_{5-20}$aryl.

28. A compound according to claim 18, wherein the terminal amino group, —NR¹R², is one of the following substituted cyclic amino groups:

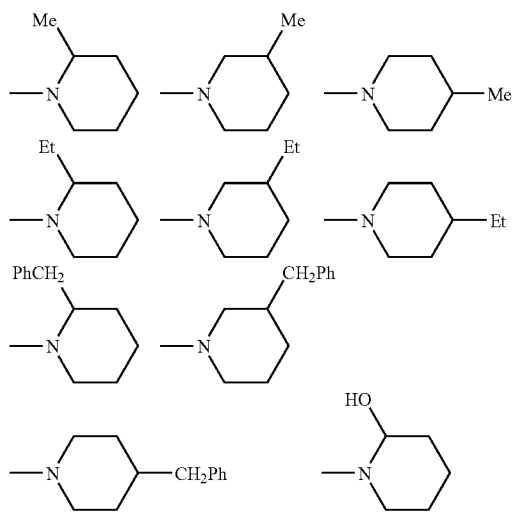

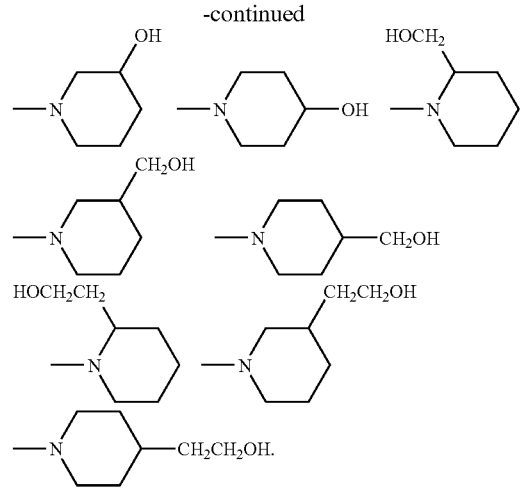

29. A compound according to claim 10, wherein $R^5$ is independently an ether substituent, and is selected from: hydrogen, $C_{1-7}$alkyl, $C_{3-20}$heterocyclyl, and $C_{5-20}$aryl; and is optionally substituted.

30. A compound according to claim 29, wherein $R^5$ is independently —H.

31. A compound according to claim 29, wherein $R^5$ is independently $C_{1-7}$alkyl, $C_{3-20}$heterocyclyl, and $C_{5-20}$aryl; and is optionally substituted.

32. A compound according to claim 29, wherein $R^5$ is independently -Me, -Et, -nPr, -iPr, -nBu, -tBu, optionally substituted -Ph, or optionally substituted -Bn.

33. A compound according to claim 3, wherein K is a 9-substituent, and is a group of the formula:

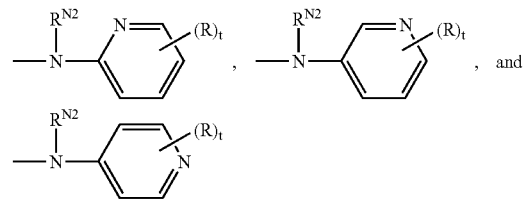

wherein t is independently an integer from 0 to 4, and each $(R)_t$ is independently a substituent selected from halo, amino, hydroxy, ether, thio, thioether, $C_{1-7}$alkyl, $C_{1-7}$haloalkyl, acyl, amido, carboxy, cyano, and aminoalkyl.

34. A compound according to claim 3, wherein K is a 9-substituent, and is a group having one of the following formulae:

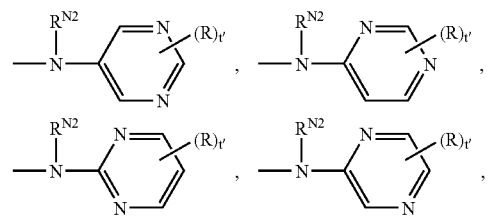

-continued

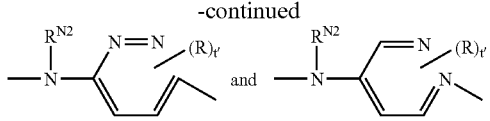

and wherein t' is independently an integer from 0 to 3, and each $(R)_{t'}$ is independently a substituent selected from halo, amino, hydroxy, ether, thio, thioether, $C_{1-7}$alkyl, $C_{1-7}$haloalkyl, acyl, amido, carboxy, cyano, and aminoalkyl.

35. A compound according to claim 3, wherein K is a 9-substituent, and is a group of the formula:

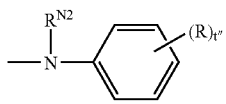

wherein t" is independently an integer from 0 to 5, and each $(R)_{t''}$ is independently a substituent selected from halo, amino, hydroxy, ether, thio, thioether, $C_{1-7}$alkyl, $C_{1-7}$haloalkyl, acyl, amido, carboxy, cyano, and aminoalkyl.

36. A compound according to claim 3, wherein K is a 9-substituent, and is a group of the formula:

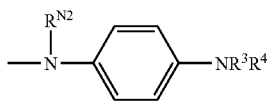

wherein —$NR^3R^4$ is as defined for —$NR^1R^2$,
wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

37. A compound according to claim 3, wherein K is a 9-substituent, and is a group of the formula:

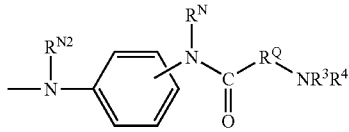

wherein $R^N$ is a nitrogen substituent as defined for $R^{N2}$, $R^Q$ is independently a $C_{1-10}$alkylene group, and —$NR^3R^4$ is as defined for —$NR^1R^2$,
wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

38. A compound according to claim 3, wherein K is a 9-substituent, and is a group of the formula:

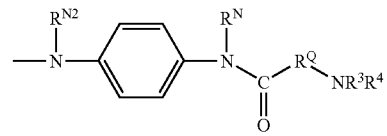

wherein $R^N$ is a nitrogen substituent as defined for $R^{N2}$, $R^Q$ is a $C_{1-10}$alkylene group, and —$NR^3R^4$ is as defined for —$NR^1R^2$,
wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

39. A compound according to claim 3, wherein K is a 9-substituent, and has the following formula:

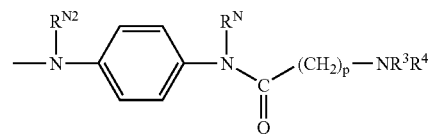

wherein $R^N$ is a nitrogen substituent, p is independently an integer from 1 to 8, and —$NR^3R^4$ is as defined for —$NR^1R^2$,
wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

40. A compound according to claim 3, wherein K is a 9-substituent, and is a group of the formula:

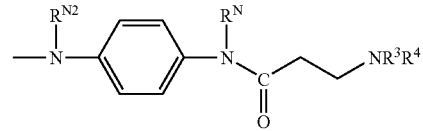

wherein $R^N$ is a nitrogen substituent as defined for $R^{N2}$, and —$NR^3R^4$ is as defined for —$NR^1R^2$,
wherein each of $R^1$ and $R^2$ of the terminal amino group, —$NR^1R^2$, is independently an amino substituent, and is hydrogen, $C_{1-7}$alkyl, $C_{3-20}$heterocyclyl, or $C_{5-20}$aryl, and is optionally substituted; or, $R^1$ and $R^2$, taken together with the nitrogen atom to which they are attached, form a heterocyclic ring having from 3 to 8 ring atoms, and is optionally substituted.

41. A compound according to claim 3, wherein K is a 9-substituent, and is a group of the formula:

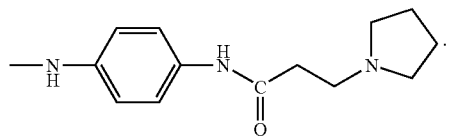

42. A compound according to claim 3, wherein K is a 9-substituent, and is a group of the formula:

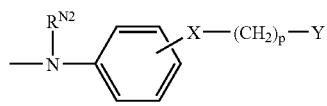

wherein:
X is —N(R$^N$)—, —CH$_2$—, —O—, or —S—;
R$^N$ is a nitrogen substituent as defined for R$^{N2}$;
Y is —OH, —OR$^Y$, or —NR$^3$R$^4$;
—OR$^Y$ is as defined for —OR$^5$;
—NR$^3$R$^4$ is as defined for NR$^1$R$^2$; and,
p is independently an integer from 1 to 8,
wherein each of R$^1$ and R$^2$ of the terminal amino group, —NR$^1$R$^2$, is independently an amino substituent, and is hydrogen, C$_{1-7}$alkyl, C$_{3-20}$heterocyclyl, or C$_{5-20}$aryl, and is optionally substituted; or, R$^1$ and R$^2$, taken together with the nitrogen atom to which they are attached, form a heterocyclic ring having from 3 to 8 ring atoms, and is optionally substituted.

43. A compound according to claim 3, wherein K is a 9-substituent, and Q is independently a C$_{1-7}$alkyl group optionally substituted with one or more amino groups, one or more hydroxy groups, one more ether groups, one or more carboxy groups, one or more C$_{3-20}$heterocyclyl groups, or one or more C$_{5-20}$aryl groups.

44. A compound according to claim 3, wherein K is a 9-substituent, and is a group of the formula:

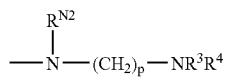

wherein p is independently an integer from 1 to 8, and the group —NR$^3$R$^4$ is as defined for —NR$^1$R$^2$,
wherein each of R$^1$ and R$^2$ of the terminal amino group, —NR$^1$R$^2$, is independently an amino substituent, and is hydrogen, C$_{1-7}$alkyl, C$_{3-20}$heterocyclyl, or C$_{5-20}$aryl, and is optionally substituted; or, R$^1$ and R$^2$, taken together with the nitrogen atom to which they are attached, form a heterocyclic ring having from 3 to 8 ring atoms, and is optionally substituted.

45. A compound according to claim 3, wherein K is a 9-substituent, and is a group of the formula:

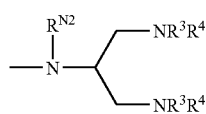

wherein each group —NR$^3$R$^4$ is as defined for —NR$^1$R$^2$,
wherein each of R$^1$ and R$^2$ of the terminal amino group, —NR$^1$R$^2$, is independently an amino substituent, and is hydrogen, C$_{1-7}$alkyl, C$_{3-20}$heterocyclyl, or C$_{5-20}$aryl, and is optionally substituted; or, R$^1$ and R$^2$, taken together with the nitrogen atom to which they are attached, form a heterocyclic ring having from 3 to 8 ring atoms, and is optionally substituted.

46. A compound according to claim 3, wherein K is a 9-substituent, and Q is, or comprises, an alicyclic saturated C$_{1-7}$alkyl group, and is optionally substituted.

47. A compound according to claim 3, wherein K is a 9-substituent, and is a group of the formula:

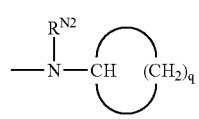

wherein q is independently an integer from 2 to 7, and wherein the cyclic group is optionally substituted.

48. A compound according to claim 3, wherein K is a 9-substituent, and is a group of one of the following formulae:

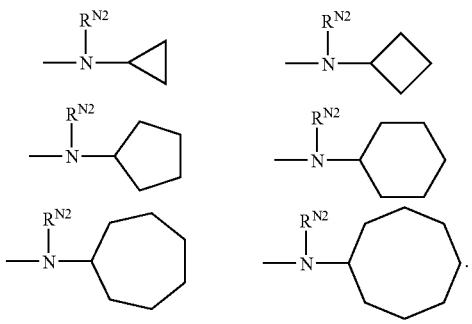

49. A compound according to claim 3, wherein K is a 9-substituent, and is a group of the formula:

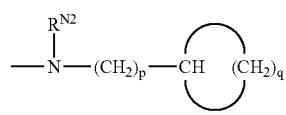

wherein p is independently an integer from 1 to 8 and q is independently an integer from 2 to 7, and wherein the cyclic group is optionally substituted.

50. A compound according to claim 3, wherein K is a 9-substituent, and is a group of one of the following formulae:

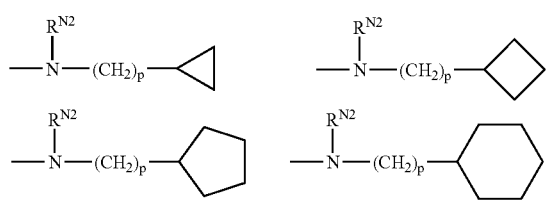

-continued

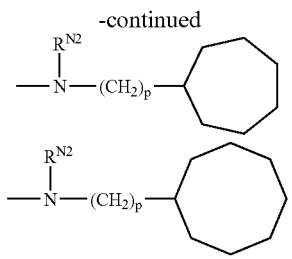

wherein p is independently an integer from 1 to 8, and wherein the cyclic group is optionally substituted.

51. A compound according to claim 3, wherein K is a 9-substituent, and is a group of the formula:

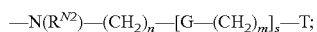

wherein:
n is independently an integer from 1 to 8;
each m is independently an integer from 1 to 8;
s is independently an integer from 0 to 3;
each G is independently —O— or —NR$^N$—;
each R$^N$ is independently a nitrogen substituent as defined for R$^{N2}$;

T is independently a terminal amino group, —NR$^1$R$^2$ or a terminal ether group, —OR$^5$,
wherein each of R$^1$ and R$^2$ of the terminal amino group, —NR$^1$R$^2$, is independently an amino substituent, and is hydrogen, C$_{1-7}$alkyl, C$_{3-20}$heterocyclyl, or C$_{5-20}$aryl, and is optionally substituted; or, R$^1$ and R$^2$, taken together with the nitrogen atom to which they are attached, form a heterocyclic ring having from 3 to 8 ring atoms, and is optionally substituted.

52. A compound according to claim 1, wherein each R$^{N1}$ is independently —H, -Me, -Et, -nPr, -iPr, -tBu, -Bn, or -Ph.

53. A compound according to claim 1, wherein each R$^{N1}$ is independently —H.

54. A compound according to claim 1, wherein each R$^{N2}$ is independently —H, -Me, -Et, -nPr, -iPr, -tBu, -Bn, or -Ph.

55. A compound according to claim 1, wherein each R$^{N2}$ is independently —H.

56. A compound according to claim 1, wherein each R$^{N1}$ and R$^{N2}$ is independently —H, -Me, -Et, -nPr, -iPr, -tBu, -Bn, or -Ph.

57. A compound according to claim 1, wherein each R$^{N1}$ and R$^{N2}$ is independently —H.

58. A compound selected from the following compounds, and pharmaceutically acceptable salts, esters, amides, solvates, and protected forms thereof:

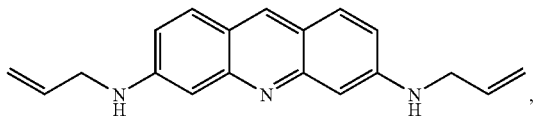

BSU-SB-36/102

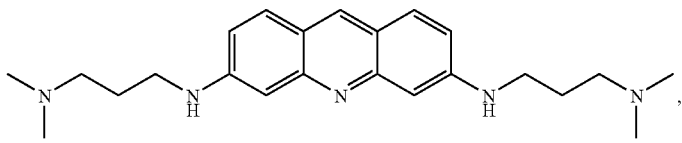

BSU-SB-36/100

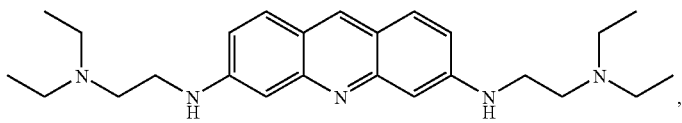

BSU-SB-36/104

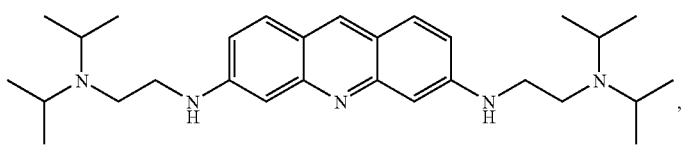

BSU-SB-36/108

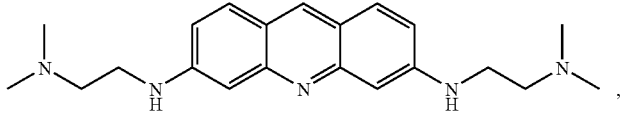

BSU-SB-36/106

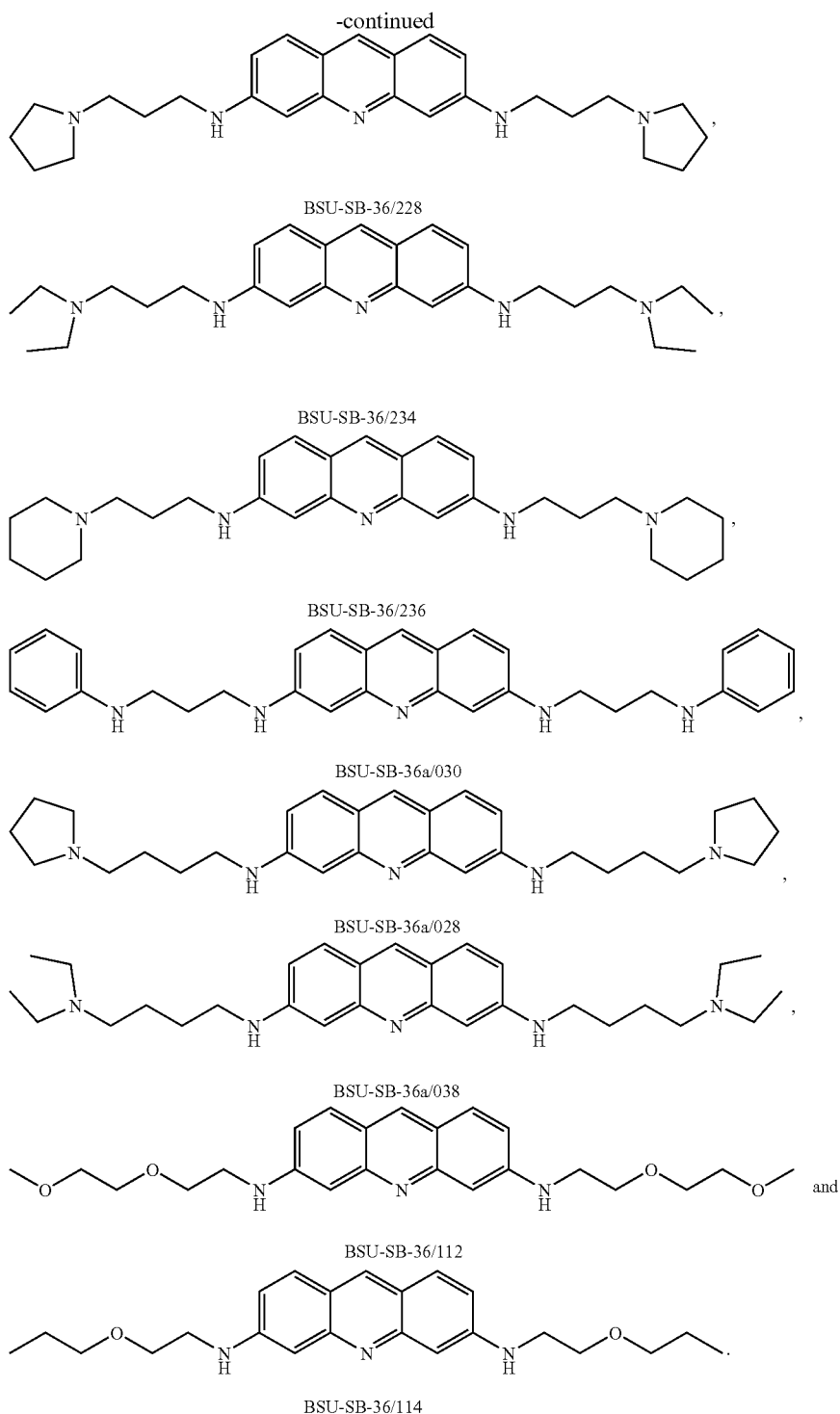
59. A pharmaceutical composition comprising a therapeutically effective amount of a compound according to claim 1 and a pharmaceutically acceptable carrier or diluent.
* * * * *